United States Patent [19]

Murphy et al.

[11] Patent Number: 4,997,950
[45] Date of Patent: Mar. 5, 1991

[54] C-TERMINAL GASTRIN ANTAGONISTS

[76] Inventors: Richard Finbar Murphy, Dept. of Biomedical Sciences, Creighton University School of Medicine, California & 24th Sts., Omaha, Nebr. 68178; Alistair J. Douglas, Dept. of Chemistry - Bldg. 43, University of California at San Diego, La Jolla, Calif. 92093; Brian Walker, Dept. of Biochemistry, Queen's University of Belfast - Medical Biology Center, Belfast, Northern Ireland, BT9 7BL

[21] Appl. No.: 341,084

[22] Filed: Apr. 20, 1989

[51] Int. Cl.$^5$ .................. C07D 473/00; C07D 209/20
[52] U.S. Cl. ...................... 548/303; 548/407/494/496
[58] Field of Search ............... 548/496, 494, 303, 407; 260/998.2

[56] References Cited

PUBLICATIONS

Douglas, A. et al., *Regulatory Peptides*, 18,367 (1987).

Primary Examiner—Mary C. Lee
Assistant Examiner—Joseph K. McKane

[57] ABSTRACT

A series of derivatives of the biologically active C-terminus of gastrin was synthesized to study the structural activity of the molecule and also to determine the smallest and highest affinity inhibitor of gastrin. Earlier work speculated that a peptide resistant to dipeptidase contained in a receptor would be an effective gastrin antagonist. Methods: Five dogs with both chronic gastric fistulae and Heidenhein pouches were used. After an 18 hour fast, gastric juice was collected both from the gastric fistula and pouch over 200 minutes at 10 minute intervals. MMC (Migrating Motor Complex) was monitored by a small balloon in the gastric antrum. Collections were initiated at the beginning of phase I of the MMC and were obtained under 3 conditions: Control, pentagastrin infusion (0.5 μg/Kg/h, i.v.) and pentagastrin+peptide infusion (Indole propionic acid [IPA]-Leu-Asp-Phenethyl amine [PEA], Boc-Trp-Leu-βAla, IPA-Leu-βAla, or Boc-Trp-Leu-Asp-methyl meta Aminobenzoic acid {mABAOMe] at 20 pmol/kg/h for 70 min.). Pentagastrin infusion was started immediately before the next peak of the MMC. Peptides were infused 60 minutes after starting pentagastrin infusion. Results: All four peptides inhibited the stimulated acid secretion causing it to approach the control level.

| Inhibition of the stimulated acid secretion ($\Delta$ meq/kg) | | |
|---|---|---|
| | Gastric Fistula | Heidenhein Pouch |
| IPA—Leu—Asp—PEA | ↓ 303 ± 120* | ↓ 18 ± 11* |
| Boc—Trp—Leu-βAla | ↓ 618 ± 168** | ↓ 35 ± 8** |
| IPA—Leu-βAla | ↓ 562 ± 249* | ↓ 34 ± 12* |
| Boc—Trp—Leu—Asp-mABAOMe | ↓ 446 ± 172** | ↓ 40 ± 16** |

(*$p < 0.05$ **$p < 0.01$, mean ± s.e.)

It is concluded that even small di-and tripeptide derivatives of the gastrin C-terminal fragment with varied resistance to hydrolysis can exhibit antagonist activity to pentagastrin stimulated gastric acid secretion.

1 Claim, No Drawings

C-TERMINAL GASTRIN ANTAGONISTS

BACKGROUND OF THE INVENTION

Field of the Invention

This invention relates to novel analogues of gastrin. In particular, this invention relates to a series of peptide analogues, modified at the N- and C- terminals, which act as potent and specific antagonists of gastrin-stimulated acid secretion.

Overproduction of gastrin has been identified as a significant, and often causative biological event in a variety of pathological disorders such as gastrinoma, antral G-cell hyperplasia, ulcer disease, pernicious anemia, and atrophic gastritis. Therefore, an effective gastrin antagonist, that is, a compound which inhibits the actions of endogenous gastrin, would be a useful therapeutic agent for the treatment of such gastrin-related conditions. Furthermore, such an antagonist, when modified to contain a physicochemically detectable group or moiety, would be useful for the detection of gastrin, quantitatively or qualitatively, for prognostic or diagnostic purposes where the binding of gastrin to receptors is biologically significant.

It is principal object of this invention to provide a novel class of potent gastrin antagonists. Another object is to provide novel probes for the detection of gastrin.

Discussion of the Prior Art

It has been shown that N-tBOC-Trp-Leu-Asp-NH$_2$ is the shortest C-terminal fragment of gastrin exhibiting antagonist properties, being active at a concentration of 100 μM. Joint infusion of the peptide (40 μg/kg) and pentagastrin (0.5 μg/kg) resulted in a 50 % reduction of acid secretion (see "Preparation and Biological Activity of N-BOC-Trp-Leu-β-Ala: A C-Terminal Gastrin Analogue", A. J. Douglas, et al., *Regulatory Peptides* (18) 1987, p. 367.

Summary of the Invention

In accordance with this invention, potent and specific antagonists of gastrin-stimulated acid secretion are provided. These compounds are peptides which contain an indole moiety and a β-carboxylic acid separated by a hydrophobic residue. Preferably, the compounds of this invention have the following general formula:

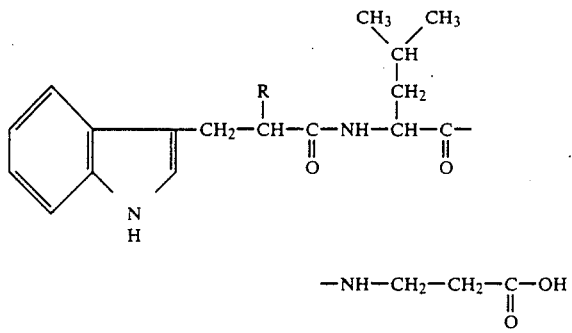

wherein R is
H—,
or NH$_2$—.

The biological activity of each of the analogues was determined in vivo by the modulation of acid secretion from the rat and dog stomach, and in vitro by the secretion of amylase from isolated pancreatic acini. The results of the biological studies indicated that analogues based on the sequence Trp-Leu-β-Ala were specific antagonists of pentagastrin-stimulated acid secretion in rats and dogs at a dose of 20 pmol.kg$^{-1}$.h$^{-1}$, however, none of the analogues had any effect on amylases secretion from rat pancreatic acini. The major determinant for receptor recognition of gastrin appears to be contained within the peptide Trp-Met-Asp and this sequence is not recognised by the cholecystokinin receptor. Derivatives of Trp-Leu-β-Ala were tested for their proteolytic stability and they were shown to be stable to several gastrointestinal proteinases over a period of 24 hours. The location of receptors for Trp-Leu-β-Ala within rat gastrointestinal mucosa was demonstrated using the biotin-streptavidin interaction. The receptors were located on non-parietal cells within fundic, duodenal and colonic mucosa. These results lend some weight to the hypothesis that gastrin-stimulated acid secretion is mediated by the release of cellular histamine. The conclusion is that these short peptides are potent and specific antagonists of gastrin, and they may be of use in the therapeutic control of acid secretion.

Such therapeutic control is achieved by the ability of the compounds of this invention to competitively inhibit the actions of endogenous gastrin. The following uses are illustrative:

Adjunctive therapy with drugs such as omeprazole which block the release of acid resulting in elevated levels of gastrin because of lack of suppression of gastrin release by acid;

control of gastronintestinal function;

control of direct or control of gastrin or histamine release;

control of colonic tumors, gastric tumors, or esophageal cancer due to reflux of duodenal and/or gastric contents to the esophagus;

competitive inhibition of mitogenic properties of gastrin be they direct or in concert with other growth promoting or carcinogenic agents; and protection against carcinogenic or pro-carcinogenic actions of gastrin in the promotion or development of colonic cancers or cancers originating in other tissues having gastrin receptors.

In general, the compounds of this invention can be used where gastrin levels are abnormally high due to any medical therapy or clinical condition.

These compounds are administered to a patient suffering from abnormally high gastrin levels in pharmaceutically effective dosage forms so as to inhibit gastric secretion and return the patient to normal levels. The compounds can be administered orally or parenterally. When in oral dosage form, a pharmaceutically acceptable salt of the compound is generally employed.

The diagnostic probes of this invention are compounds having the above general formula wherein R is any physicochemically detectable group capable of bonding to the —CH— located beta to the indole moiety, provided that such group does not alter the ability of the compound to bind specifically to the gastrin receptor. Examples of such groups are biotin-NH—, dansyl-NH—, and fluorescein-NH—.

These probes can be used to detect gastrin quantitatively or qualitatively for prognostic or diagnostic purposes and are particularly useful in such applications where the binding of gastrin to receptors is biologically significant.

EXPERIMENTAL SECTION

4.1 General Methods

4.1.1 Preparation of Solutions, Solvents and Reagents

All aqueous solutions were prepared using water with a resistivity of 18 MΩ cm$^{-1}$ prepared with a Millipore Milli-Q system. The following solvents and reagents were purified for use in peptide synthesis:

Acetic anhydride was left standing over phosphorous pentoxide overnight and then fractionally distilled.

Anhydrous ammonia was prepared by passage over potassium hydroxide pellets.

Diazomethane in diethyl ether was prepared by the method of de Boer (1953). In brief, ethanol (95%, 25 ml) was added to a solution of potassium hydroxide (5g) in water (8 ml). The mixture was contained in a three neck flask (100 ml) fitted with a pressure equalising dropping funnel and a condenser set downwards for distillation. The flask containing the alkali was maintained in a water bath at 65° C. N-Methyl-N-nitroso-toluene-p-sulphonamide (Diazald) (21.4 g, 100 mol) in diethyl ether (200 ml) was added slowly from the dropping funnel to the alkaline solution over a period of 25 minutes. The distillate containing diazomethane was collected at 0° C. and stored at −20° C. until required.

Dichloromethane was refluxed over phosphorous pentoxide for 4 hours and then fractionally distilled.

Dicyclohexylamine was refluxed over potassium hydroxide pellets for 1 hour and then fractionally distilled.

Diethyl ether was dried by standing over sodium wire.

Dimethylformamide was dried by standing over 4 Å molecular sieves for at least 48 hours.

A saturated solution of HCl in diethyl ether was prepared by bubbling anhydrous HCl(g), generated by the action of concentrated sulphuric acid on sodium chloride, into anhydrous diethyl ether at 0° C. for 3 hours.

Hydrogen fluoride was dried by condensing the gas into a teflon chamber containing cobalt trifluoride (100 mg).

N-Methylmorpholine was refluxed over potassium hydroxide pellets for 2 hours and then distilled. The distillate was stored over potassium hydroxide pellets.

Pyridine was dried over potassium hydroxide pellets and then distilled. The distillate was stored over 4 Å molecular sieves.

Tetrahydrofuran was left standing over sodium wire for 24 hours and then distilled from calcium hydride. The distillate was stored over calcium hydride.

Triethylamine was refluxed over potassium hydroxide pellets for 2 hours and then fractionally distilled.

Trifluoroacetic acid was refluxed over phosphorous pentoxide for 2 hours and then fractionally distilled.

4.2 Characterisation of the Synthetic Compounds

4.2.1 Thin Layer Chromatography

All the compounds synthesized were examined by thin layer chromatography (tlc) in one or more of the following solvent systems (proportions are by volume).
A chloroform-methanol (4:1)
B chloroform-methanol (1:1)
C methanol
D ethyl acetate-cyclohexane (1:1)
E 1-butanol-acetic acid-water (3:1:1)
F chloroform-methanol (95:5)

Spots were usually detected by their U.V. absorbance at 254 nm.

Sulphur containing compounds were detected by means of an azide/iodine spray (Chargaff et al., 1948) (1% sodium azide w/v/ 1% iodine w/v in 50% aqueous ethanol). Other compounds were detected by iodine vapour or ninhydrin. All tlc was carried out on thin layer chromatographic aluminium sheets, precoated with silica gel 60F$_{254}$ (0.2 mm) purchased from Merck, distributed through BDH Chemicals Ltd., Poole, England.

4.2.2 Spot Test for the Detection of Free Terminal Amino Groups

The method of Troll and Canon (1953), as modified by Kaiser et al. (1970), was utilised. Three solutions were prepared: (a) 500 mg ninhydrin in 10 ml ethanol, (b) 80 g phenol in 20 ml ethanol, and (c) 2 ml of 0.001M solution of potassium cyanide diluted to 100 ml with α-picoline. A small sample of peptide (1–2mg) was placed in a b 2 ml glass vial and 2–3 drops of each of the three reagents were added. The vial was heated at 100° C. for 5 minutes. Free terminal amino groups gave a positive colour reaction (blue for tryptophan, leucine and phenylalanine, and deep red for aspartic acid). Protected amino groups and deprotected secondary amines gave a yellow colour indicating a negative result.

4.2.3 High Performance Liquid Chromatography

All the compounds synthesised were examined by high performance liquid chromatography (h.p.l.c.). The analytical apparatus consisted of a Waters model 720 system controller, a Waters model 6000A solvent pump, a Waters model 45 solvent pump, a Waters U6K injector and a Water model 441 absorbance detector (214 nm). The separation was accomplished using either a Waters μBondapak C$_{18}$ column (3.9 mm × 30 cm) or a Waters radial compression module fitted with a μBondapak C$_{18}$ cartridge (8 mm × 10 cm). The peptides were dissolved in h.p.l.c. grade methanol and 10 μl aliquots were injected onto the column. The samples were eluted using a linear gradient of distilled water containing 0.05% (v/v) trifluoroacetic acid to acetonitrile containing 0.05% (v/v) trifluoroacetic acid.

Preparative reverse-phase h.p.l.c. was carried out on a Waters LC 3000 Deltaprep system. The separation was achieved with a Waters Deltapak C$_{18}$ column (19 mm × 30 cm) and the peptide was eluted at a flow rate of 47 ml.min$^{-1}$ using the same linear gradient as the analytic separation.

4.2.4 Melting Points

Melting points were determined on a Gallenkamp melting point apparatus, and are uncorrected.

4.2.5 Infra-red Spectra

Infra-red spectra of all the compounds were run on a Perkin-Elmer 257 grating spectrophotometer.

4.2.6 Elemental Analysis

Elemental analyses were carried out by Mr. J. Swindall, Department of Chemistry, Queen's University, Belfast.

4.2.7 Amino Acid Analysis

Amino acid analyses were carried out using a Waters Picotag amino acid analyser by Mrs. A Healy, Department of Biochemistry, Queen's University, Belfast.

4.2.8 Nuclear Magnetic Resonance Spectra $^1$H nuclear magnetic resonance (n.m.r.) spectra were recorded on a Brucker WM 250 spectrophotometer operating at 250 MHz.

4.3 Biological Studies

4.3.1 Acid Secretory Studies

The Acid secretory studies were carried out in vivo using three different animal models.

In brief fasted male Sprague-Dawley rats (200-250 g) were anaesthetised by the intravenous administration of Sagital (0.1 mg/100 g body weight). The abdominal cavity of each rat was exposed and the stomach was ligated at the pyloric and cardiac sphincters. The test solution (200 μl), containing either saline, pentagastrin (1 μg) or the synthetic peptide in conjunction with pentagastrin (1 μg), was applied directly to the exposed stomach surface, and left for 80 minutes. The stomach was then removed and the contents were washed out with distilled water (15 ml). The washings were titrated to neutrality by the addition of sodium hydroxide (10 mM).

In brief, stomachs from fasted male Wistar rats (240-270 g) were completely isolated and placed in organ baths filled with Krebs-Ringer buffer. The vascular bed was perfused at a rate of 2 ml.min$^{-1}$ with Krebs-Ringer buffer containing 5 mM glucose, 5 mM pyruvate, 40 mg.ml$^{-1}$ bovine serum albumin and 10% (v/v) fresh, washed ovine erythrocytes gassed with 96% $O_2$, 4% $CO_2$ by a membrane oxygenator. The gastric lumen was perfused with distilled water (pH 7.0) gassed with $O_2$ (100%). All perfusates and the organ bath were kept at 37° C. After an initial "wash-out" period of 20 minutes, isobutylmethylxanthine (50 μM) was added to the vascular perfusate. After a further 20 minutes, the peptide to be tested was added, giving a final peptide concentration of $10^{-9}$, $10^{-7}$ or $10^{-5}$M. Five other stomachs were given 520 pM gastrin which was known to produce maximal acid secretion. Furthermore, each peptide was given together with gastrin (520 pM) to evaluate the gastrin inhibitory properties of the peptide. The acid output was determined by titration of the lumenal perfusate to neutrality with dodium hydroxide (1 mM).

In brief, six beagle dogs were surgically prepared with Heidenhain pouches and gastric fistula. The dogs were fasted for 18 hours before the experiment. The secretions were collected from the fistula by simple gravity drainage, whereas the wash-out method of Magee and Nakajima (1968) was used for the pouch. Collections of gastric secretions were recovered at 10 minute intervals. Each dog received an intravenous infusion throughout the experiment consisting of 150 mM NaCl and 8 mM KCl at 2 ml.min$^{-1}$. Secretory stimulants and the synthetic peptides were added to this infusion at appropriate rates. The stimulants of gastric secretion used were pentagastrin and histamine phosphate. Pentagastrin (0.5 μg.Kg$^{-1}$.h$^{-1}$) was given for 1 hour and then the synthetic peptide was added to the infusion and continued for another hour at a dose of 20 pmol.kg$^{-1}$h$^{-1}$. The procedure was identical for histamine except that the dose of histamine was 25 mg.kg$^{-1}$.h$^{-1}$. The ten minute samples were titrated to pH 7.0 by the addition of sodium hydroxide (1 mM) and the acid secretion was expressed as μmol H$^+$ per 10 minutes. Pepsin secretion was estimated by the method of Anson (1938).

4.3.2 Pancreatic Secretory Studies

The effect of the synthetic peptides on amylase secretion from isolated pancreatic acini was determined by the method of Bruzzone et al. (1985).

In brief, pancreatic acini were isolated from male Wistar rats (180-200 g) by collagenase digestion. The acini were preincubated at 37° C. in Krebs-Ringer buffer for 30 minutes before the addition of any stimulants. The acini were allowed to settle under gravity and the buffer was decanted off. The acini were resuspended in fresh Krebs-Ringer buffer and samples of the supernatant were immediately removed for determination of the amylase content by the method of Bernfeld (1955). The value obtained represents the initial amylase secretion from which the percentage increase in secretion is calculated. The remaining acinar suspension was aliquoted (0.5 ml) into vials, to which were added the peptides dissolved in Krebs-Ringer buffer. The incubation was allowed to proceed for 30 minutes after which time the amylase content of each supernatant was determined. The results were expressed as a percentage increase of the initial amylase content.

4.4 Enzyme Degradation Studies

The proteolytic stability of a number of the synthetic peptides was determined in vitro. In the presence of pepsin, chymotrypsin and enkephalinase (E.C.3.4.24.11).

4.4.1 Assay of Pepsin Activity

The activity of the pepsin solution was determined by the method of Bayliss et al. (1969). In brief, haemoglobin (2 g) was dissolved in distilled water (50 ml). Hydrochloric acid (0.3M, 20 ml) was added and the solution was made up to 100 ml with distilled water. Samples (3 ml) of this solution were pipetted into glass test tubes which were placed in a thermostatically controlled water bath at 37° C. Pepsin (0.1 mg) was dissolved in hydrochloric acid (20 mM, 0.2 ml) and 100 μl of this solution was added to one of the test tubes. Water (100 μl) was added to another test tube as a blank. The two tubes were inverted twice and the reaction was allowed to proceed for 10 minutes at 37° C. Trichloroacetic acid The activation of the carboxyl group usually involves the replacement of the hydroxyl function by a moiety which is a good leaving group and which increases the electrophilicity of the carbonyl carbon atom. The earliest method of activation relied on the formation of an azide (—CON$_3$) which is capable of acylating a free amino function with the formation of a peptide bond (FIG. 5.4) (Curtius, 1902). Due to the high optical purity of the products, the azide method is still widely favoured. The use of acid chlorides as acylating agents became popular around the same time as the azide method. However, undesired side reactions such as the formation of N-carboxy-anhydrides and contamination of the peptides with phosphorous compounds, especially when phosphorous oxychloride was used to prepare the acid chloride, made the method unpopular for peptide synthesis.

Both the acid chloride method and the azide method were superceded as acylating agents by the introduction of anhydrides. The rate of formation of peptide bonds with anhydrides is extremely rapid while the degree of racemisation is very low. Both the mixed anhydride with carbonic acids (FIG. 5.5) and the symmetrical anhydride involving carbodiimides (FIG. 5.6) have been used extensively in peptide synthesis. The mixed anhydride method is particularly attractive for peptide synthesis since it has a high rate of reaction at low temperatures, a high purity of products, satisfactory yields and is the least expensive of the coupling procedures. There is a high tendency for racemisation with the mixed anhydride reaction due to the strong activation of the carboxyl carbonyl and therefore it has been limited to the activation of single amino acids with N-α-urethane protecting groups (Z or Boc) which suppress racemisation. Coupling by the mixed anhydride method involves two separate stages: (1) activation of the carboxyl component, and (2) coupling with the amino component.

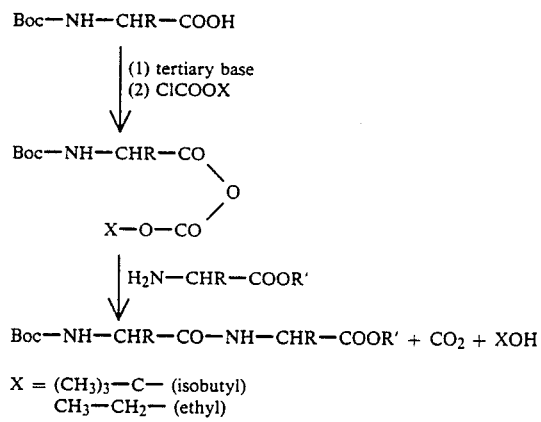

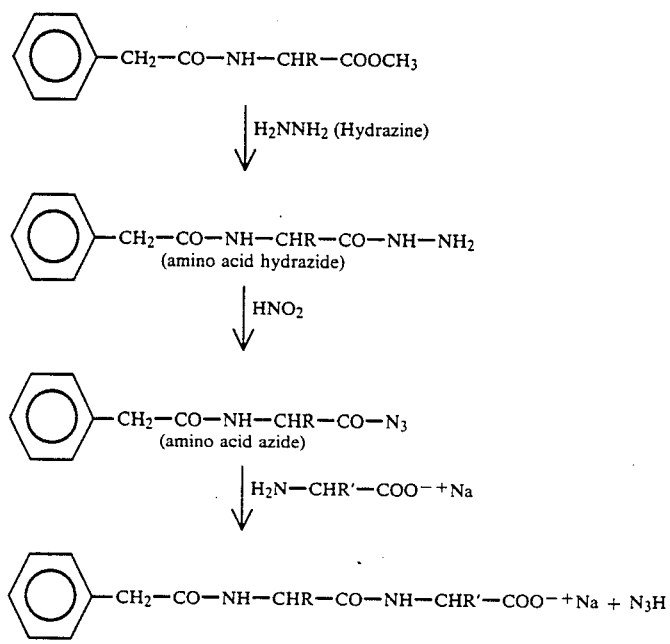

FIG. 5.4 Azide coupling procedure.

FIG. 5.5 The mixed anhydride coupling procedure.

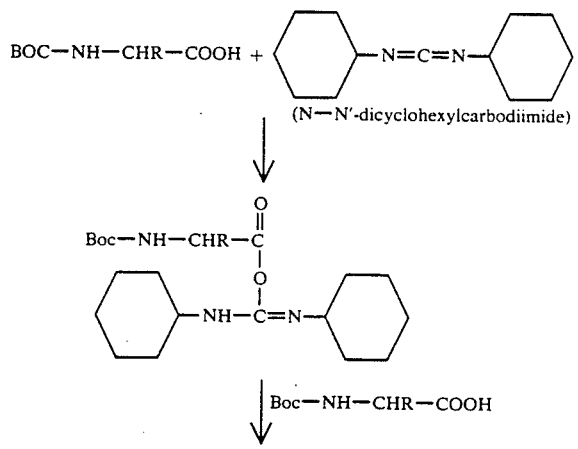

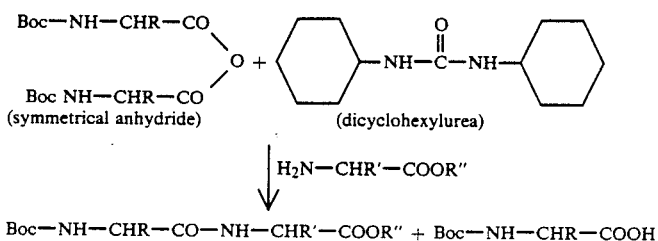

Boc—NH—CHR—CO—NH—CHR'—COOR" + Boc—NH—CHR—COOH

FIG. 5.6 The symmetrical anhydride coupling procedure.

The activation step involves the addition of a carbonic acid monoalkyl ester chloride (e.g. isobutyl chloroformate) to a cold solution of the carboxyl component anion in anhydrous organic solvent. Upon formation of the anhydride, the amine component is added to the reaction and coupling occurs with the release of carbon dioxide and a volatile alcohol.

The carbodiimide method of Khorana (1953), was introduced to peptide synthesis by Sheenan and Hess (1955) using dicylohexylcarbodiimide (DCC). There are a number of products which can be formed during the activation process and which are dependant on the conditions of the reaction (FIG. 5.7). The spontaneous rearrangement of the O-acyl urea to the N-acyl urea occurs in polar, aprotic solvents such as dimethylformamide and represents loss of the protected amino acid by the formation of unreactive byproducts. The symmetrical amino acid anhydride, formed during the carbodiimide mediated activation, has found widespread application for the coupling steps in solid phase peptide synthesis (Merrifield, 1962; Merrifield, 1963). The DCC method is also widely used for the preparation of N-protected amino acid active esters based on nitrophenol and N-hydroxysuccinimide (Rothe and Kunitz, 1957; Elliot and Russell, 1957; Bodanszky and Du Vigneaud, 1959).

Although the activation of the amino group is less frequently used, it can be accomplished by the formation of amides of phosphorous or other acids which render the nitrogen susceptible to nucleophilic attack by the carboxyl group (FIG. 5.8).

FIG. 5.7 The N-N'-dicyclohexylcarbodiimide coupling reaction.

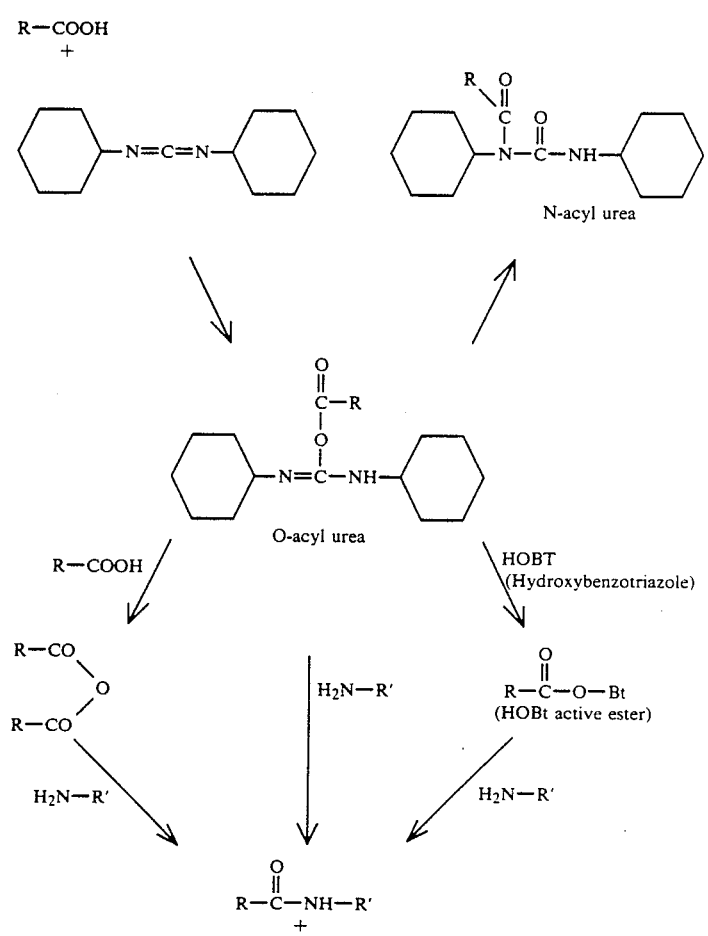

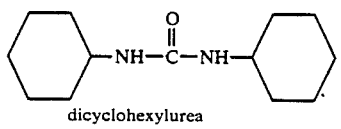

dicyclohexylurea

FIG. 5.7

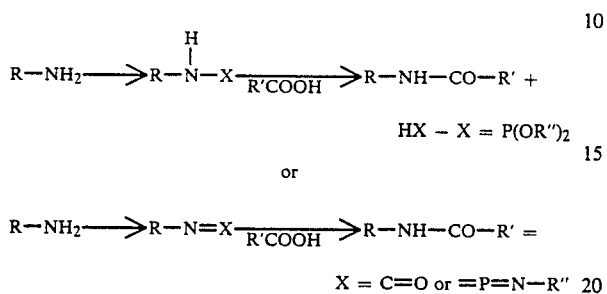

FIG. 5.8 Amino group activation.

5.2.3 Formation of Peptide Bond Isosteres

5.2.3.1 The N-alkyl Peptide Bond

A number of hormone analogues have been prepared with N-alkyl isosteres (Roemer et al., 1977; Rivier et al., 1976; Sandberg et al., 1981). There are two methods available for the formation of an N-alkyl isostere. Both are based on the replacement of the hydrogen ion by the alkyl group in the presence of alkali (FIG. 5.9). The method of Pachter and Kloetzel (1952) involves refluxing the protected amine in the presence of powdered potassium hydroxide and methyl iodide. The use of this procedure is limited to the N-alkylation of protected aromatic amines and is of little value in the preparation of N-alkylated amino acids. Cheung and Benoitin (1977) modified the N-alkylation reaction for both Boc and Z protected amino acids. The protected N-alkyl derivative is obtained in a quantitative yield after an overnight reaction in the presence of sodium hydride and methyl iodide. The extent of reaction is easily monitored by comparing the $^1$H n.m.r. signal of the N-alkyl protons and the protons associated with the protecting group. The alkylation of β-amino acids is particularly sluggish due to the increased acidity of the amino proton and the formation of these derivatives may require an extended reaction time or repetition of the alkylation procedure.

5.2.3.2 The Thionopeptide Bond

The formation of a thioamide linkage within a synthetic peptide can be achieved by a number of methods.

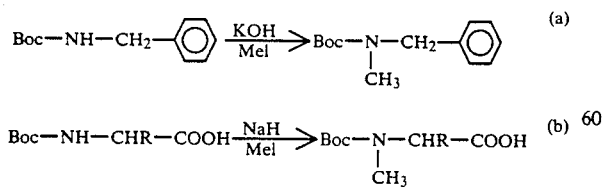

FIG. 5.9 N-Alkylation of amino groups.

Phosphorous pentasulphide has been proposed as a thionating reagent since it was first prepared by Henry (1869) and Wislicenus (1869). The reagent is, however, restricted in use to the formation of terminal thioamides and thionopeptide bonds within dipeptides with small sidechains (e.g. glycine, valine and leucine) due to the low reactivity of the compound (Bartlett et al., 1982).

Dithioesters are particularly attractive as thionating reagents since they have a very good leaving group (the thiol). The synthesis of a dithioester involves the conversion of a protected amino acid nitrile to the imino ester in the presence of anhydrous HCl and a thiol (Pinner and Klein, 1878) (FIG. 5.10). The dithioester is formed by thiolysis of the imino ester in the presence of $H_2S$ and pyridine. The synthesis has a number of disadvantages; namely, long periods of time may be required for the unstable iminoester formation, the yields are frequently poor, the only acceptable protecting group is the Z function and the final product is often contaminated with the thioamide which is the product of a competing reaction during thiolysis. Suydam et al. (1969) described an alternative route whereby the imidate hydrochloride is formed by the reaction of ethyl chloroformate with an amide or thioamide. Rezniak et al. (1973) modified the method to facilitate the synthesis of dithioesters from the corresponding thiochloroformate (FIG. 5.11). The applicability of this reaction for thionopeptide synthesis is limited due to a very low yield of the dithioester caused by steric hinderance of bulky sidechain constituents in the thioamide and thiochloroformate. Due to the extreme acidity of the Pinner reaction and the difficulty of Fmoc-amino acid nitrile preparation, the only suitable protecting group of use in the preparation of dithioesters is the carbobenzoxy (Z) group.

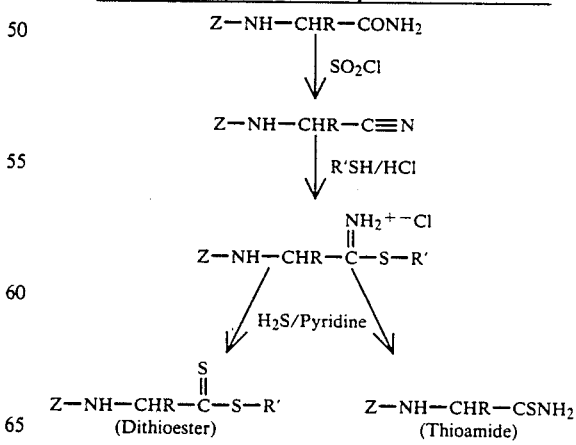

FIG. 5.10
The synthesis of dithioesters by the Pinner reaction.

FIG. 5.11 Synthesis of thioimidate hydrochlorides by the method of Razniak et al. (1973).

FIG. 5.11

X—NH—CHR—CSNH₂ + Cl—CO—SR'

(X = Fmoc,Boc,Z)

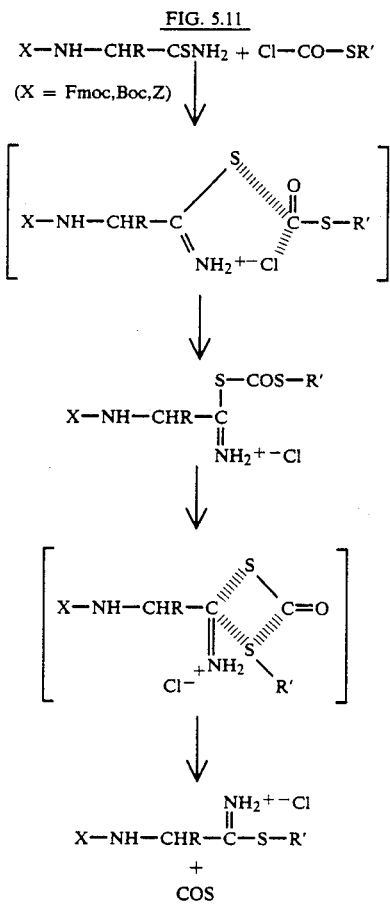

+
COS

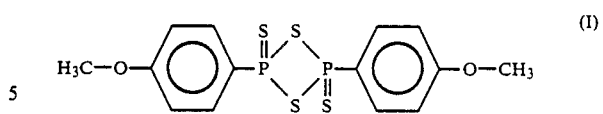

The advantages of this type of reagent are the ease of preparation and potential reactivity with a wide range of carbonyl compounds. The mechanism of thionation using Lawesson's regent was proposed by Perregaard et al. (1977) and Navech et al. (1983) (FIG. 5.12). Based on the proposed mechanism, it is possible that a highly reactive dithiophosphine ylide, rather than Lawesson's reagent, is the active thionating reagent. The formation of the dithiophosphine ylide has been confirmed by structural, kinetic and spectroscopic studies (Rauchfuss and Zank, 1986). The stoichiometry of the reaction was investigated by Scheibye et al. (1978). A ratio of 0.5:1.0 reagent-reactant resulted in near quantitative thionation. The reaction is carried out below 110° C. to minimise thermal decomposition or polymerisation (Lawesson et al., 1977) and thionation is accompanied by the quantitative formation of the trimer (II) which is isolated as a white powder of low solubility.

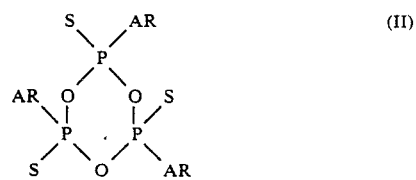

FIG. 5.12
Mechanism of the reaction of Lawesson's reagent with a carbonyl group.

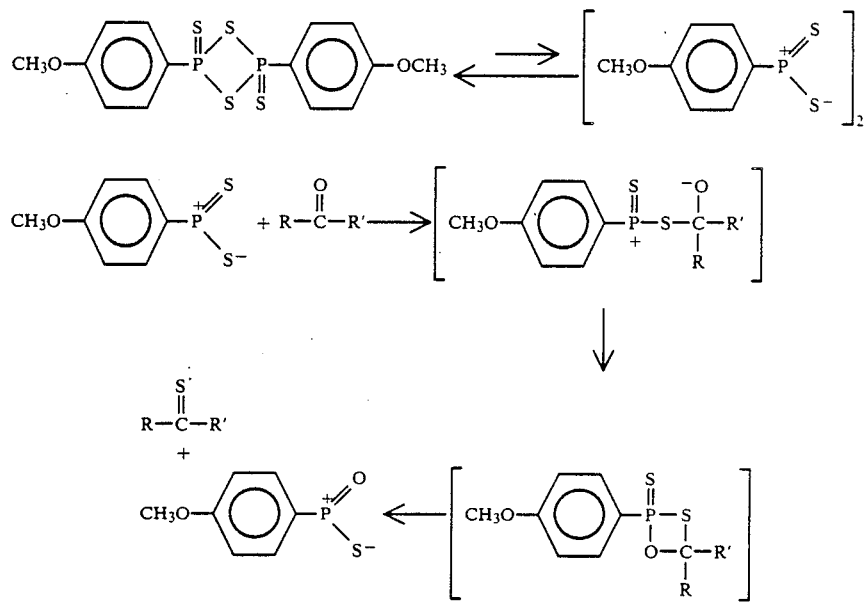

5.2.3.3 The Methyleneoxy Bond

The methyleneoxy derivative has a number of advantages over other peptide bond isosteres. Firstly, it is highly resistant to proteolytic and chemical attack. Secondly, it has unit dimensions ($C_\alpha^i$–$C_\alpha^{i+1}$) which are very similar to the amide bond and lastly, it has negligi- Thionation can also be brought about by the use of D/S exchange reagents such as Lawesson's reagent (2,4-bis-[P-methoxyphenyl]-1,2,3,4-dithia-diphosphetane-2,4-disulphide) (I).

ble nucleophilicity and increased polarity compared to the related thiomethylene (—$CH_2$—S—) linkage. The preparative methodology has been well documented (Ondetti et al., 1972; Tinney et al., 1985; Rubini et al., 1986) and is summarised in FIG. 5.13. The protected amino alcohol is deprotonated in the presence of sodium hydride and then undergoes attack by a bromoalkyl ester in the presence of 18-crown-6. The ester of the pseudodipeptide is removed by saponification and the dipeptide unit is purified by means of the carboxylic acid group. The reaction of the bromo ester with the alcohol proceeds with chiral inversion of the bromo derivative. The D-bromo derivative of chiral amino acids must be used in order to preserve the natural chirality (L-) of the peptide.

5.2.3.4 The Haloketone Analogue

The introduction of haloketone groups has mainly been confined to the design of short peptide-based enzyme inhibitors (Schoellman and Shaw, 1962; Ong et al., 1965; Shaw, 1967; Kettner and Shaw, 1978). The haloketone group has only been incorporated into one peptide hormone, namely bradykinin (Aplin et al., 1983) and the analogue was devoid of biological activity. The synthetic route to the haloketones is depicted in FIG. 5.14. The derivatives are potent alkylating agents of amino, hydroxyl and thiol groups.

FIG. 5.13
The synthesis of methyleneoxy pseudopeptide bonds.

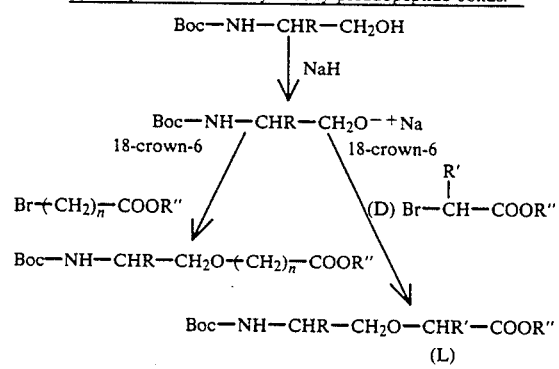

FIG. 5.14 The synthesis of haloketones.

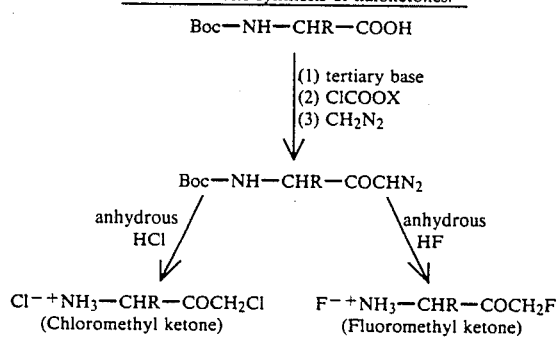

Due to their alkylating properties, the chloromethyl ketones are potent, irreversible inhibitors of both serine (Powers and Tuhy, 1973) and cysteine (Bender and Brubacher, 1966) proteinases. The use of chloromethyl ketones is restricted in vivo due to the extreme reactivity towards thiol groups. Rauber et al. (1986) developed the fluoromethyl ketone which has a reduced susceptibility to nucleophilic displacement, increased specificity and fewer problems with side reactions. The replacement of an essential carboxylic acid sidechain, which is involved in receptor binding, by a haloketone may produce a hormone analogue with irreversible binding characteristics.

5.2.3.5 The Ketomethyleneamino Bond

The first reported analogues containing the ketomethylene amino bond were based on substrates for angiotensin-converting enzyme (Natarajan et al., 1984; Gordon et al., 1984). The analogues were non-hydrolysable, reversible inhibitors ($IC_{50}$ 6 nM). An inhibitor of collagenase (Ki 60 $\mu$M) containing the ketomethylene amino isostere has also been prepared (Wallace et al., 1986). No peptide hormone analogues containing this pseudopeptide have been prepared. The synthesis of the analogue involves the alkylation of a primary amino function by a peptide chloromethyl ketone. In the presence of sodium iodide, the chloromethyl ketone is transiently converted to the iodomethyl ketone by halogen exchange and the more reactive iodomethylketone alkylates the free amino group with the subsequent formation of the ketomethylene amino bond.

5.2.3.6 Conformationally Restricted Dipeptide Lactams

The formation of a conformationally restrained $\beta$-turn can be induced in a synthetic sequence by the introduction of a $\gamma$-lactam dipeptide. The chemical synthesis of such a unit has been accomplished by Freidinger et al. (1982). The five membered pyrrolidine ring had the simplest preparation and facilitated the introduction of two asymmetric centres with little or no racemisation. The synthesis of the unit (FIG. 5.15) involves the intramolecular alkylation of a methionine sidechain followed by abstraction of the amide proton and ring closure. Conventional solid phase or solution peptide synthesis can then be carried out utilising the lactam unit. Freidinger (1981) demonstrated that the gamma lactam unit has a high degree of structural homology with a type II' $\beta$-turn (III).

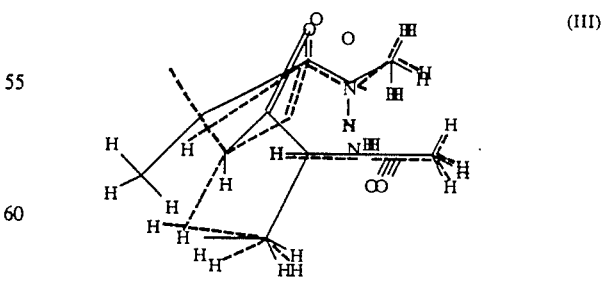

Fit of a $\gamma$-lactam conformational constraint (dashed) with a Type II' $\beta$-turn (solid)

FIG. 5.15 The synthesis of a conformationally restrained $\gamma$-lactam dipeptide unit.

FIG. 5.15

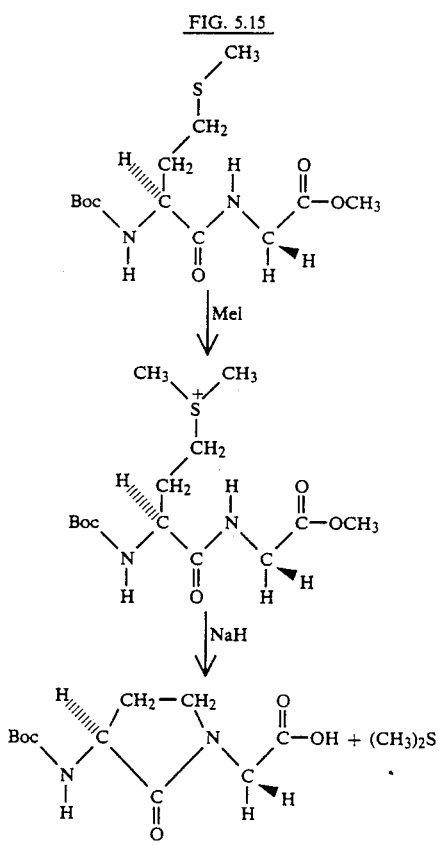

5.3 Peptide Synthesis

5.3.1 Preparation of t-Butyloxycarbonyl-L-Leucine (Boc-Leu)

Di-tert-butyldicarbonate (55 mmole) in tetrahydrofuran (30 ml) was added to a solution (200 ml) of L-leucine (50 mmol) in tetrahydrofuran/5% $NaHCO_3$ (1:1 v/v). The reaction was allowed to proceed overnight at room temperature. The organic solvent was removed under reduced pressure and the resulting aqueous solution was washed with diethyl ether (2×30 ml). On acidification with 5% $NaHSO_4$, the product precipitated and was extracted into ethyl acetate (250 ml). The organic layer was removed and reduced to dryness. The product was crystallised from ethanol/water. The method was derived from that described by Moroder et al. (1976). Yield 84%, m.p. 85°-87° C. (lit. 85°-87° C., Fletcher and Jones, 1972). The product was homogeneous as judged by tlc in chloroform/methanol (4:1) (Rf 0.500) or methanol (Rf 0.426).

5.3.2 Preparation of t-Butyloxycarbonyl-L-Tryptophan (Boc-Trp)

This was prepared by the method previously described (Section 5.3.1). Recrystallisation was from ethyl acetate/petrol ether (40°/60° C). Yield 72%, m.p. 136°-138° C. (lit. 137°-139° C., Nagasawa et al., 1973). The product was homogeneous as judged by tlc in chloroform/methanol (4:1) (Rf 0.211) or chloroform/methanol (1:1) (Rf 0.389).

5.3.3 Preparation of t-Butyloxycarbonyl-1-1-Amino Cyclohexane Carboxylic Acid This was prepared by the method previously described (Section 5.3.1). Recrystallisation was from ethyl acetate/petrol ether (40°/60° C.). Yield 5.7 g (72%), m.p. 178°-179° C. The product was homogeneous as judged by the tlc in chloroform/methanol (4:1) (Rf 0.688) or chloroform/methanol (1:1) (Rf 0.644). (Found: C, 58.94; H, 8.72; N, 5.68. $C_{12}H_{21}O_4N_1$ requires C, 59.26; H, 8.64; N, 5.76%).

5.3.4 Preparation of t-Butyloxycarbonyl-L-Leucyl N-Hydroxysuccinimide Ester (Boc-Leu-OSu)

Boc-L-Leu (5 g, 21.6 mmol) was dissolved in anhydrous dichloromethane (100 ml). N-N'-Dicyclohexylcarbodiimide (4.9 g, 23.8 mmol) and N-hydroxysuccinimide (2.74 g, 23.8 mmol) were added and the reaction mixture was stirred overnight at room temperature. The precipitate of dicyclohexylurea was removed by filtration, the resulting clear solution was reduced to dryness and the residue was dissolved in ethyl acetate (100 ml). The organic solution was washed quickly with 5% $NaHCO_3$, 5% $NaHSO_4$ and brine, and dried over magnesium sulphate. The solution was filtered and the solvent was removed in vacuo. The residue was recrystallised from hot isopropanol. Yield 6 g (91%), m.p. 109°-111° C. (lit. 111°-113° C., Mitchell et al., 1978). The product was homogeneous by tlc in chloroform/methanol (4:1) (Rf 0.664) or chloroform/methanol (1:1) (Rf 0.381). (Found: C, 54.62; H, 7.41; N, 8.51. $C_{15}H_{24}O_6N_2$ requires C, 54.88; H, 7.32; N, 8.53%).

5.3.5 Preparation of t-Butyloxycarbonyl-L-Tryptophyl N-Hydroxysuccinimide ester (Boc-Trp-OSu)

This was prepared by the method outlined in Section 5.3.4. The product was recrystallised from hot isopropanol/petrol ether (40°/60° C.). Yield 4.43 g (67%), m.p. 152°-153° C. (Lit. 153°-154° C., Anderson et al., 1964a). The product was homogeneous as judged by tlc in chloroform/methanol (4:1) (Rf 0.664) or chloroform/methanol (1:1) (Rf 0.531). (Found: C, 59.79; H, 5.62; N, 10.41. $C_{20}H_{23}O_6N_3$ requires C, 59.85; H, 5.73; N, 10.47%).

5.3.6 Preparation of Phenyl-3-propionyl N-Hydroxysuccinimide Ester (PPA-OSu)

This was prepared by the method outlined in Section 5.3.4. The product was crystallised from hot isopropanol/petrol ether (40°/60° C.). Yield 1483 g (89%), m.p. 120°-122° C. The product was homogeneous as judged by tlc in chloroform/methanol (4:1) (Rf 0.695) or chloroform/methanol (1:1) (Rf 0.772). (Found: C, 63.11; H, 4.99; N, 5.56. $C_{13}H_{13}O_4N$, requires C, 63.16; H, 5.26; N, 5.67%).

5.3.7 Preparation of β-alanyl-benzyl Ester

This was prepared by the Dean-Stark procedure.
In brief, β-alanine (10.1 g, 0.114 mmol) was dissolved in benzene (200 ml). Benzyl alcohol (50 ml, 0.456 mol) and toluene-4-sulphonic acid (24 g, 0.125 mol) were added and the solution was refluxed for 6 hours in a Dean-Stark apparatus. The water liberated by the formation of the ester was continuously removed. On cooling, the solution was reduced to one quarter volume and the tosyl salt of the product crystallised on addition of diethyl ether. Yield 38 g (96%), m.p. 128°-130° C. The product was homogeneous as judged by tlc in methanol (Rf 0.656) or 1-butanol/acetic acid/water (3:1:1) (Rf 0.454) (Found: C, 57.91; 6.06; N, 4.12. $C_{17}H_{21}O_5N_1S_1$ requires C, 58.12; H, 5.98; N, 3.99%).

5.3.8 Preparation of t-Butyloxycarbonyl-L-Leucyl-β-Alanine (Boc-Leu-β-Ala)

Boc-L-Leu-OSu (5 g, 15.24 mmol) was dissolved in a solution (200 ml) containing equal volumes of tetrahydrofuran and 5% $Na_2CO_3$. β-Alanine (2.71 g, 30.48 mmol) was added and the reaction mixture was stirred at room temperature for 4 hours. The organic solvent was removed in vacuo and the resulting aqueous solution was washed with diethyl ether (2×50 ml). On acidification with 5% $NaHSO_4$, the product precipitated and was extracted into ethyl acetate (150 ml). The organic layer was washed with brine and dried over magnesium sulphate. On reduction to dryness, Boc-Leu-β-Ala was initially obtained as a clear oil but on standing at −20° C., formed an amorphous solid. The product was judged homogeneous by tlc in chloroform/methanol (4:1) (Rf 0.514) or chloroform/methanol (1:1) (Rf 0.554). Yield 2.89 g (63%), m.p. 91°–92° C. (Found: C, 55.61; H, 8.61; N, 9.29. $C_{14}H_{26}O_5N_2$ requires C, 55.63; H, 8.61; N, 9.27%).

5.3.9 Preparation of t-Butyloxycarbonyl-L-Tryptophyl-L-Leucyl-β-Alanine (Boc-Trp-Leu-β-Ala) (Peptide I)

The previous compound was deprotected for 1 hour in a solution of HCl in diethyl ether. The hydrochloride salt was obtained as a hygroscopic foam on removal of the solvent.

Boc-L-Trp-OSu (0.84 g. 2.09 mmol) was dissolved in a solution (200 ml) containing equal volumes of tetrahydrofuran and 5% $NaHCO_3$. The dipeptide hydrochloride salt (0.5 g, 2.1 mmol) was dissolved in 5% $NaHCO_3$ (20 ml) and added to the reaction. After stirring at room temperature for 4 hours, the tetrahydrofuran was removed under reduced pressure. The aqueous solution was washed with diethyl ether (2×50 ml) and acidified by the addition of 5% $NaHSO_4$. The product was extracted into ethyl acetate (150 ml) and washed with brine. It was dried over magnesium sulphate and reduced to near dryness. The product precipitated on addition of petrol ether (40°/60° C. and was recrystallised from diethyl ether/petrol (40°/60° C.). Yield 0.82 g (80%), m.p. 103°–105° C. The product was homogeneous as judged by tlc in chloroform/methanol (4:1) (Rf 0.432) or chloroform/methanol (1:1) (Rf 0.597). (Found: C. 61.59; H, 7.47; N, 11.46. $C_{25}H_{36}O_6N_4$ requires C, 61.47; H, 7.38; N, 11.47%).

5.3.10 Preparation of Phenyl-3-Propionyl-Leucyl-β-Alanine (PPA-Leu-β-Ala) (Peptide II)

This was prepared by the method previously described (Section 5.3.9). The product was obtained as an intractable oil. On conversion to the dicylcohexylamine salt and addition of diethyl ether, a white crystalline product was obtained. Yield 1.08 g (63%), m.p. 111°–113° C. The product was homogeneous as judged by tlc in chloroform/methanol (1:1) (Rf 0.292) or methanol (0.201). (Found: C, 70.07; H, 9.52; N, 7.96 $C_{30}H_{49}O_4N_3$ requires C, 69.90; H, 9.51; N, 8.15%).

5.3.11 Preparation of t-Butyloxycarbonyl-L-Leucyl-β-alanyl benzyl ester (Boc-Leu-βAla-OBzl)

Boc-L-Leucine (1.5 g, 6.49 mmol) was dissolved in anhydrous tetrahydrofuran (30 ml) and chilled to −15° C. N-Methylmorpholine (0.72 ml, 6.49 mmol) was added followed by isobutyl chloroformate (0.88 ml, 6.82 mmol). The mixture was stirred for 10 minutes after which time β-alanyl benzyl ester (2.5 g, 7.14 mmol) was added in a solution (50 ml) containing equal volumes of anhydrous tetrahydrofuran and dimethylformamide, and N-methylmorpholine (0.79 ml, 7.14 mmol). The reaction was allowed to proceed overnight at room temperature after which time the solvents were removed in vacuo. The residue was dissolved in ethyl acetate (100 ml) and washed thoroughly with 5% $NaHSO_4$, 5% $NaHCO_3$ and brine. The organic layer was dried over magnesium sulphate and reduced to dryness. The product was obtained as an intractable oil. Yield 1.54 g (63%). It was judged homogeneous by tlc in chloroform/methanol (4:1) (Rf 0.492) or chloroform/methanol (1:1) (Rf 0.576). (Found: C, 64.23; H, 7.98; N, 7.27. $C_{21}H_{31}O_5N_2$ requires C, 64.28; H, 8.16; N, 7.14%).

5.3.12 Preparation of Indole-3-Propionyl-L-Leucyl-β-Alanine (IPA-Leu-β-Ala) (Peptide III)

The previous compound was deprotected for 1 hour in a solution of HCl dissolved in diethyl ether. On removal of the solvent, the hydrochloride salt was obtained as a white foam.

Indole-3-propionic acid was coupled to the deprotected dipeptide ester by the method previously described (5.3.11). The product was obtained as a clear oil. Yield 1.23 g (72%). It was homogeneous as judged by tlc in chloroform/methanol (4:1) (RF 0.810) or chloroform/methanol (1:1) (Rf 0.705).

The benzyl ester was removed by catalytic transfer hydrogenolysis (Anwer and Spatola, 1980). In brief, palladium on activated charcoal (200 mg) was added to ethanol (70 ml) under a nitrogen atmosphere. The peptide (1.0 g, 2.16 mmol) was dissolved in ethanol (20 ml) and added to the catalyst. Ammonium formate (0.58 g, 8.64 mmol) was added, followed by 4 drops of glacial acetic acid. The reaction was allowed to proceed overnight. The palladium charcoal was removed by filtration and the solvent was removed in vacuo. The residue was dissolved in ethyl and the product was precipitated by the formation of the dicyclohexylamine salt. Yield (62%), m.p. 171°–173° C. The product was homogeneous as judged by tlc in methanol (Rf 0.705) or 1-butanol/acetic acid/water (3:1:1) (Rf 0.797). (Found: C, 69.47; H, 9.04; N, 10.17. $C_{32}H_{50}O_4N_4$ requires C, 69.31; H, 9.02; N, 10.11%).

5.3.13 Preparation of t-Butyloxycarbonyl-1-1-aminocyclohexyl-N-hydroxysuccinimide ester This was prepared by the method previously described (5.3.4). The product was obtained as a crystalline solid from hot isopropanol/petrol ether (40°/60° C.). Yield 2.11 g (75%), m.p. 141°–143° C. The product was homogeneous as judged by tlc in chloroform/methanol (4:1) (Rf 0.541) or chloroform/methanol (0.603). (Found: C, 56.29; H, 7.08; N, 8.27. $C_{16}H_{24}O_6N_2$ requires C, 56.47; H, 7.06; N, 8.23%).

5.3.14 Preparation of t-Butyloxycarbonyl-1-1-aminocyclohexyl-β-Alanine

This was prepared by the method previously described (Section 5.3.8). The product was recrystallised from ethyl acetate/petrol ether (40°/60° C.). Yield 0.7 g (76%), m.p. 175°–177° C. The product was homogeneous as judged by tlc in chloroform/methanol (4:1) (Rf 0.278) or chloroform/methanol (1:1) (Rf 0.449). (Found: C, 57.47; H, 8.31; N, 8.91. $C_{15}H_{26}O_5N_2$ requires C, 57.32; H, 8.28; N 8.92%).

5.3.15 Preparation of Phenyl-3-Propionyl-1-1-Aminocyclohexyl-β-Alanine (Peptide IV)

The previous compound was deprotected for 1 hours in a solution of dichloromethane containing trifluoroacetic acid (20% v/v). The trifluoroacetate salt was obtained as a white powder on reduction to dryness and tituration with diethyl ether.

Phenyl-3-propionic acid was coupled to the deprotected dipeptide by the method previously described (Section 5.3.9). The product was obtained as an intractable oil and was converted to the dicyclohexylamine salt. Yield 0.41 g (52%), m.p. 173°–176° C. The product was homogeneous as judged by tlc in chloroform/methanol (4:1) (Rf 0.490) or chloroform/methanol (1:1) (Rf 0.174) (Found: C, 70.57; H, 9.37; N, 8.12. $C_{31}N_{49}O_4N_3$ requires C, 70.59; H, 9.29; N, 7.97%).

5.3.16 Preparation of t-Butyloxycarbonyl-L-Aspartyl(4-benzyl ester)phenethylamide (Boc-Asp(OBzl)-PEA)

This was prepared by the method previously described (Section 5.3.11). The product was crystallised from ethyl acetate by the addition of petrol ether (40°/60° C.). Yield 1.28 g (88%), m.p. 97°–98° C. The product was homogeneous as judged by tlc in chloroform/methanol (4:1) (Rf 0.803) or chloroform/methanol (1:1) (Rf 0.756). (Found: C, 67.35; H 6.83; N, 6.98. $C_{24}H_{30}O_5N_2$ requires C, 67.60; H, 7.04; N, 6.57%).

5.3.17 Preparation of t-Butyloxycarbonyl-L-Leucyl-L-Aspartyl (4 benzyl ester)-Phenethylamide (Boc-Leu-Asp(OBzl)-PEA)

The previous compound was deprotected for 1 hour in ether/HCl. The hydrochloride salt was obtained as a white powder on reduction to near dryness and addition of fresh diethyl ether.

Boc-L-leucine was coupled to the deprotected dipeptide by the method previously described (Section 5.3.11). The product was crystallised from ethyl acetate/petrol ether (40°/60° C.). Yield 1.31 g (84%), m.p. 87°–88° C. The product was homogeneous as judged by tlc in chloroform/methanol (4:1) (Rf 0.694) or choroform/methanol (1:1) (Rf 0.538). (Found: C, 66.75; H, 7.69; N, 8.01. $C_{30}H_{41}O_6N_3$ requires C, 66.79; H, 7.61; N, 7.79%).

5.3.18 Preparation of Indole-3-Propionyl-L-Leucyl-L-Aspartyl-Phenethylamide (IPA-Leu-Asp-PEA) (Peptide V)

The previous compound was deprotected for 1 hour in ether/HCl. The hydrochloride salt was obtained as a white powder on reduction to near dryness and addition of fresh diethyl ether.

Indole-3-propionic acid was coupled to the deprotected tripeptide by the method previously described (Section 5.3.11). The peptide crystallised on tituration with diethyl ether. Yield 1.02 g (79%), m.p. 174°–177° C. The product was homogeneous as judged by tlc in chloroform/methanol (4:1) (Rf 0.809) or chloroform/methanol (1:1) (Rf 0.754). The benzyl ester was removed by catalytic transfer hydrogenolysis (5.3.12). The fully deprotected peptide was obtained in quantitative yield on tituration with diethyl ether m.p. 198°–199° C. (dec.). The product was homogeneous as determined by tlc in chloroform/methanol (1:1) (Rf 0.639) or methanol (Rf 0.762). (Found: C, 67.01; H, 6.94; N, 10.62. $C_{29}H_{36}O_5N_4$ requires C, 66.92; H, 6.92; N, 10.77%).

5.3.19. Preparation of m-aminobenzoic acid methyl ester

To a chilled solution of methanol (100) was added thionyl chloride (21.25 ml, 0.29 mol). The solution was stirred for a further 30 minutes after which time m-aminobenzoic acid (10 g, 73 mmol) was added. The reaction was allowed to proceed overnight at room temperature and the solvents were then removed under reduced pressure. The product was obtained on tituration of the residue with diethyl ether. Yield 12.2 g (89%), m.p. 216°–218° C. The product was judged homogeneous by tlc in chloroform/methanol (4:1) (Rf 0.688) or chloroform/methanol (1:1) (Rf 0.597). (Found: C, 50.16; H, 5.27; N, 7.29. $C_8H_{10}O_2N_1Cl_1$ requires C, 50.26; H, 5.23; N, 7.33%).

5.3.20 Preparation of Carbobenzoxy-L-Aspartyl(4-t-butyl ester)m-aminobenzoic acid methyl ester Z-Asp(OBut) was coupled to the previous compound by the mixed anhydride method (Section 5.3.11). The product was obtained as an intractable oil. Yield 2.33 g (87%). It was judged homogeneous by tlc in chloroform/methanol (4:1) (Rf 0.761) or chloroform/methanol (1:1) (Rf 0.664). (Found C, 62.87; H, 6.27; N, 6.04. $C_{24}H_{28}O_7N_2$ Required C, 63.16; H, 6.14; N, 6.14%).

Both protecting groups were removed in the presence of HBr in acetic acid (33% v/v) at room temperature. On reduction to dryness and addition of HCl/ether, the fully deprotected peptide was obtained in near quantitative yield as a hygroscopic solid.

5.3.21 Preparation of t-Butyloxycarbonyl-L-Leucyl-L-Aspartyl-m-Aminobenzoic acid methyl ester This was prepared by the hydroxysuccinimide ester method of coupling (Section 5.3.9). The product was precipitated on acidification and extracted into ethyl acetate (150 ml). The organic layer was washed with brine, dried over magnesium sulphate and reduced to near dryness. The product precipitated as a white powder on addition of petrol ether 40°/60° C.). Yield 0.39 g (37%), m.p. 129°–133° C. The product was homogeneous as judged by tlc in methanol (Rf 0.625), or 1-butanol/acetic acid/water (3:1:1) (Rf 0.692). (Found: C, 57.59; H, 6.88; N, 8.66. $C_{23}H_{33}O_8N_3$ requires C, 57.62; H, 6.89; N, 8.77%).

5.3.22 Preparation of t-Butyloxycarbonyl-L-Tryptophyl-L-Leucyl-L-Aspartyl-m-Aminobenzoic acid methyl ester (Peptide VI)

The previous compound was deprotected for 1 hour in ether/HCl. The hydrochloride salt was obtained on reducing the volume of the solution and addition of fresh diethyl ether.

Boc-tryptophan was coupled to the deprotected tripeptide by the N-hydroxysuccinimide ester method (Section 5.3.9). The peptide was crystallised from diethyl ether/petrol ether (40°/60° C. Yield 0.16 g (50%), m.p. 152°–154° C. The product was homogeneous as judged by tlc in chloroform/methanol (4:1) (Rf 0.630) or chloroform/methanol (1:1) (Rf 0.705). (Found: C, 61.27; H, 6.48; N, 10.49. $C_{34}H_{43}O_9N_5$ requires C, 61.35; H, 6.46; N, 10.52%).

5.4 Synthesis of Thionopeptides

5.4.1 Preparation of t-Butyloxycarbonyl-L-Phenylalanine (Boc-Phe)

This was prepared by the method previously described (Section 5.3.1). The product was recrystallised from hot cyclohexane. Yield 70%, m.p. 87°–88° C. (Lit. 85°–87° C., Neubert et al., 1972). The product was homogeneous as judged by tlc in chloroform/methanol (4:1) (Rf 0.517) or chloroform/methanol (1:1) (Rf 0.642).

5.4.2 Preparation of t-Butyloxycarbonyl-L-Phenylalanyl amide (Boc-Phe-NH$_2$)

Boc-L-Phenylalanine (5 g, 18.8 mmol) was dissolved in anhydrous tetrahydrofuran (70 ml) and chilled to $-15°$ C. N-Methylmorpholine (2.1 ml, 18.8 mmol) and isobutyl chloroformate (2.56 ml, 19.8 mmol) were added and the resulting cloudy solution was stirred for 5 minutes. Dry ammonia gas was bubbled through the solution for a further 10 minutes. The flask was sealed and stirred for 4 hours at room temperature. The solvents were removed under reduced pressure and the product was precipitated directly by the addition of 5% NaHCO$_3$. The white solid was washed copiously and dried over phosphorous pentoxide. Yield 4.53 g (91%), m.p. 127°–129° C. The product was judged homogeneous by tlc in chloroform/methanol (4:1) (Rf 0.670) or chloroform/methanol (1:1) (Rf 0.744). (Found: C, 63.62; H, 7.41; N, 10.62. $C_{14}H_{20}O_3N_2$ requires C, 63.54; H, 7.59; N, 10.69%).

5.4.3 Preparation of t-Butyloxycarbonyl-L-Phenylalanyl methylamide (Boc-Phe-NHCH$_3$)

This was prepared by the method previously described (Section 5.4.2) using methylamine (33% in ethanol). On removal of the solvents and addition of 5% NaHCO$_3$, the product precipitated as a white powder. Yield 5.02 g (95%), m.p. 136°–138° C. The product was homogeneous as determined by tlc in chloroform/methanol (4:1) (Rf 0.748) or chloroform/methanol (1:1) (Rf 0.783). (Found: C, 64.58; H 7.88; N, 10.22. $C_{15}H_{22}O_3N_2$ requires C, 64.75; H, 7.91; N, 10.07%).

5.4.4 Preparation of t-Butyloxycarbonyl-L-Aspartyl-(4 benzyl ester)-amide (Boc-Asp(OBzl)-NH$_2$)

This was prepared by the method previously described (Section 5.4.2). Yield 1.86 g (93%), m.p. 135°–137° C. The product was homogeneous as judged by tlc in chloroform/methanol (4:1) (Rf 0.693) or chloroform/methanol (1:1) (Rf 0.772). (Found: C, 59.49; H, 672; N, 8.82. $C_{16}H_{22}O_5N_2$ requires C, 59.63; H, 6.93; N, 8.69%).

5.4.5 Preparation of L-Phenylalanyl thioamide (Phe(t)-NH$_2$)

Boc-L-Phenylalanyl amide (4.0 g, 15.1 mmol) was dissolved in anhydrous dichloromethane (50 ml) and phosphorous pentasulphide (6.7 g, 15.1 mmol) was added. Triethylamine (8.47 ml, 60.4 mmol) was added dropwise to the slurry to initiate the reaction. The solution was sealed and stirred at room temperature overnight. The solution was washed copiously with 5% NaHSO$_4$ until the washes were clear. The organic layer was then washed with water and dried over magnesium sulphate. On reduction to dryness, the product was obtained as a brown oil. Crystallisation was accomplished from diethyl ether/petrol ether (40°/60° C.). Yield 3.7 g (70%), m.p. 140°–142° C. The product was homogeneous as judged by tlc in chloroform/methanol (4:1) (Rf 0.767) or C, 59.95; H, 6.97; N, 9.88. $C_{14}H_{20}O_2N_2S_1$, requires C. 60.00; H 7.14; N, 10.00%). The product was deprotected for 1 hour in ether/HCl. Upon removal of the solvent and addition of fresh diethyl ether, the hydrochloride salt was obtained in quantitatives yield as a white powder (m.p. 185°–187° C.).

5.4.6 Preparation of L-Phenylalanyl-thiomethylamide (Phe(t)-NHCH$_3$)

This was prepared by the method previously described (Section 5.4.5). The product crystallised on addition of anhydrous diethyl ether. Yield 0.57 g (54%), m.p. 141°–143° C. The Boc protected product was homogeneous as determined by tlc in chloroform/methanol (4:1) (Rf 0.707) or chloroform/methanol (1:1) (Rf 0.716). (Found: C, 60.98; H, 7.45; N, 9.57. $C_{15}H_{22}O_2N_2S_1$ requires C, 61.22; H, 7.48; N, 9.52%). The product was deprotected for 1 hour in ether/HCl. Upon removal of the solvent and addition of fresh diethyl ether the hydrochloride salt precipitated in quantitative yield as a white powder (m.p. 176°–178° C.).

5.4.7 Preparation of L-Aspartyl(4 benzyl ester)-thioamide (Asp(OBzl)(t)-NH$_2$)

This was prepared by the method described previously (Section 5.4.5). On removal of the dichloromethane, the product crystallised. It was washed with diethyl ether and dried under vacuum. Yield 0.25 g (24%), m.p. 144°–145° C. The product was homogeneous as judged by tlc in chloroform/methanol (4:1) (Rf 0.777) or chloroform/methanol (1:1) (Rf0.775). (Found: C. 57.01; H, 6.55; N, 7.15. $C_{16}H_{22}O_4N_2S_1$ requires C, 56.80; H, 6.51; N, 7.10%).

The product was deprotected for 1 hour in ether/HCl. On reduction of the solvent to near dryness and addition of fresh diethyl ether, the hydrochloride salt precipitated in quantitative yield as a white powder (m.p. 148°–150° C.).

5.4.8 Preparation of Carbobenzoxy-L-Leucyl amide (Z-Leu-NH$_2$)

This was prepared by the method previously described (Section 5.4.2). On treatment of the residue with 5% NaHCO$_3$, the product precipitated as a white powder. Yield 8.96 g (90%), m.p. 122°–124° C. (Lit. 125°–126° C., Lloyd and Young, 1971). The product was homogeneous as judged by tlc in chloroform/methanol (4:1) (Rf 0.643) or chloroform/methanol (1:1) (Rf 0.734). (Found: C, 63.49; H, 7.34; N, 10.52. $C_{14}H_{20}O_3N_2$ requires C, 63.63; H, 7.57; N, 10.60%).

5.4.9 Preparation of 1-(Carbobenzoxy-amino-1-cyano-3-methyl-butane (Z-Leu-CN)

Z-L-leucyl amide (2 g, 7.57 mmol) was dissolved in anhydrous dimethylformamide and chilled to 0° C. thionyl chloride (1.65 ml, 22.7 mmol) was added slowly and the resulting solution was stirred to 30 minutes. On reduction to dryness and addition of iced water (200 ml), the product precipitated and was extracted into ethyl acetate (300 ml). The organic phase was washed thoroughly and dried over magnesium sulphate. On removal of the solvents, the nitrile was obtained as an intractable yellow oil. Yield 1.23 g (64%). The product was homogeneous as determined by tlc in chloroform/methanol (4:1) (Rf 0.787) or chloroform/methanol (1:1) (Rf 0.693). (Found: C, 68.39; H, 7.09; N, 11.39. $C_{14}H_{18}O_2N_2$ requires C, 68.29; H, 7.32; N, 11.38%).

5.4.10 Preparation of Carbobenzoxy-L-Leucyl dithiobenzyl ester

Z-L-leucyl nitrile (1.2 g, 4.88 mmol) and benzyl mercaptan (2.3 ml, 19.52 mmol) were dissolved in anhydrous tetrahydrofuran (70ml) and chilled to 0° C. Dry HCl gas was bubbled through the solution for 3 hours after which time the solvent was removed and the residue was washed copiously with anhydrous diethyl ether. The imino ester was dissolved in anhydrous tetrahydrofuran (50 ml) containing anhydrous pyridine (0.6 ml, 7.32 mmol) and $H_2S$ gas was bubbled through the solution for 10 minutes. The solvent was removed under reduced pressure and the residue was dissolved in ethyl acetate (150 ml). The organic phase was washed throughly with 5% $NaHCO_3$, 5% $NaHOS_4$ and water. After standing over magnesium sulphate and reduction to dryness, the product was obtained as a brown oil. Yield 0.7 g (37%). The product was judged homogeneous by tlc in chloroform/methanol (4:1) (Rf 0.783) or chloroform/methanol (1:1) (Rf 0.806). However, analysis by $^1H$ n.m.r. indicated that the alternative rearrangement to the thioamide had occurred with a ratio of 70:30 of the dithioester to the thioamide.

5.4.11 Preparation of Carbobenzoxy-L-Phenylalanine (Z-Phe)

L-Phenylalanine (5 g, 30 mmol) was dissolved in a solution (200 ml) containing equal proportions of tetrahydrofuran and 5% $NaHCO_3$, and chilled to 0° C. Benzyl chloroformate (4.7 ml, 33 mmol) was dissolved in tetrahydrofuran (10 ml) and added slowly to the amino acid solution over a period of 1 hour. The pH was continually adjusted to 8.5 by the addition of 5% $Na_2CO_3$ and the reaction was allowed to proceed at room temperature overnight. The organic solvent was removed under reduced pressure and the resulting aqueous solution was poured slowly into chilled, concentrated HCl (50 ml). The product precipitated and was extracted into ethyl acetate (200 ml). It was washed with 5% $NaHSO_4$ and dried over magnesium sulphate. Recrystallisation was from ethyl acetate/hexane. Yield 8.29 g (91%), m.p. 83°–83° C. (Lit. 82°–84° C., Berger et al., 1973). The product was homogeneous as judged by tlc in chloroform/methanol (4:1) (Rf 0.500) or chloroform/methanol (1:1) (Rf 0.364).

5.4.12 Preparation of Carbobenzoxy-L-Phenylalanyl amide (Z-Phe-NH$_2$)

This was prepared by the method previously described (Section 5.4.2).

The amide precipitated or removal of the solvents and was washed copiously with 5% $NaHCO_3$. Yield 7.9 g (99%), m.p. 162°–164° C. (Lit. 164°–165° C., Wünsch and Deimer, 1972). The product was homogeneous as judged by tlc in chloroform/methanol (4:1) (Rf 0.738) or chloroform/methanol (1:1) (Rf 0.652). (Found: C, 68.34; H, 5.92; N, 9.44. $C_{17}H_{18}O_3N_2$ requires C, 68.45; H, 6.04; N, 9.39%).

5.4.13 Preparation of 1-(Carbobenzoxy-amino)-1cyano-2-phenyl-ethane (Z-Phe-CN)

This was prepared by the method previously described (Section 5.4.9). The nitrile precipitated as a yellow solid on addition of ice-cold water. It was washed copiously with 5% $NaHSO_4$, 5% $NaHCO_3$ and water. Yield 0.66 g (58%), m.p. 120°–121° C. The product was homogeneous as determined by tlc in chloroform/methanol (4:1) (Rf 0.803) or chloroform/methanol (1:1) (Rf 0.728). (Found; C, 72.79; H, 5.77; N, 9.89. $C_{9.89}$. $C_{17}H_{16}O_2N_2$ requires C, 72.86; H, 5.71; N, 10.00%).

5.4.14 Preparation of Carbobenzoxy-L-Phenylalanyl-dithiobenzyl ester

This was prepared by the method previously described (Section 5.4.10).

The ester was obtained as an intractable brown oil. Yield 0.42 g (56%). The product was homogeneous as judged by tlc in chloroform/methanol (4:1) (Rf 0.828) or chloroform/methanol (1:1) (Rf 0.801). However, analysis by $^1H$ n.m.r. indicated that the alternative rearrangement to the thioamide had occurred with a ratio of 80:20 of the dithioester to the thiomide.

5.4.15 Preparation of L-Leucyl-Thiono-$\beta$-Alanine (Leu(t)-$\beta$-Ala)

Boc-L-leucyl-$\beta$-Alanyl benzyl ester (Section 5.3.11) (3.0 g, 7.65 mmol) was dissolved in benzene (200 ml) and Lawesson's reagent (1.85 g, 4.59 mmol) was added. On refluxing at 80° C., the Lawesson's reagent dissolved and heating was continued for a further 8 hours. The solution was allowed to cool to room temperature overnight. The conversion of the product was confirmed by tlc and the iodine-azide test. After the benzene was removed under reduced pressure, the residue was taken up in ether/HCl (100 ml ) and left at room temperature overnight. The solution was reduced to near dryness and fresh ether was added. The hydrochloride salt of the thionopeptide precipitated slowly over a period of 24 hours at 4° C. Yield 0.8 g (31%), m.p. 149°–150° C. The product was homogeneous as judged by tlc in methanol (Rf 0.00) or 1-butanol/acetic acid/water (3:1:1) (Rf 0.582). (Found: C, 54.82; H, 7.29; N, 8.06. $C_{16}H_{25}VO_2N_2S_1Cl_1$ requires C, 55.17; H, 7.18; N, 8.04%).

The benzyl ester was removed by treatment with HBr in acetic acid (33% v/v) containing anisole (0.2% v/v). On reduction to dryness and tituration with diethyl ether, the product was obtained in quantitative yield as a hygroscopic foam.

5.4.16 Preparation of Carbobenzoxy-L-Aspartyl (4 tert-butyl ester)-L-Phenylalanyl amide (Z-Asp(OBut)-Phe-NH$_2$)

This was prepared by the method previously described (Section 5.3.11). Crystallisation was from diethyl ether/petrol ether (40°/60° C.). Yield 2.78 g (65%), m.p. 158°–159° C. (Lit. 159°–160° C., Wünsch and Deimer, 1972). The product was homogeneous as judged by tlc in chloroform/methanol (4:10 (Rf 0.707) or chloroform/methanol (1:1) (Rf 0.696). (Found: C, 63.89; H, 6.59 N, 9.12. C$_{25}$H$_{31}$O$_6$N$_3$ requires C, 63.96; H, 6.61; N, 8.95%).

5.4.17 Preparation of tert-Butyloxycarbonyl-L-Leucyl-L-Aspartyl (4-tert-butyl-ester)-L-Phenylalanyl amide (Boc-Leu-Asp(OBut)-Phe-NH$_2$)

The Z group of the previous compound was removed by catalytic transfer hydrogenolysis (Section 5.3.12) in quantitative yield.

Boc-L-Leu was coupled to the dipeptide by the method previously described (Section 5.3.11). Crystallisation was from diethyl ether/petrol ether (40°/60° C.). Yield 0.39 g (69%), m.p. 142°–144° C. The product was homogeneous as judged by tlc in chloroform/methanol (4:1) (Rf 0.667) or chloroform/methanol (1:1) (Rf 0.441). (Found: C, 61.25; H, 8.11; N, 10.17. C$_{28}$H$_{44}$O$_7$N$_4$ requires C, 61.31; H, 8.03; N, 10.22%).

5.4.18 Preparation of tert-Butyloxycarbonyl-L-Leucyl-L-Aspartic acid (4 benzyl ester) (Boc-Leu-Asp(OBzl))

This was prepared by the N-hydroxysuccinimide ester coupling method (Section 5.3.9). The product was obtained as an intractable oil. Yield 0.7 g (53%). It was judged homogeneous by tlc in chloroform/methanol (1:1) (Rf 0.742) or methanol (0.714). (Found: C, 60.55; H, 7.49; N, 6.40. C$_{22}$H$_{32}$O$_7$N$_2$ requires C, 60.55; H, 7.34; N, 6.42%).

5.4.19 Preparation of tert-Butyloxycarbonyl-L-Trytophyl-L-Leucyl-L-Aspartic acid (4-benzyl ester) (Boc-Trp-Leu-Asp(OBzl))

The previous compound was deprotected for 1 hour in ether/HCl. On reduction of the solution to near dryness and addition of fresh diethyl ether, the hydrochloride salt precipitated as a white powder.

Boc-L-tryptophan was coupled to the dipeptide by the method previously described (Section 5.3.9). The product was obtained in the crystalline form by conversion to the dicyclohexylamine salt followed by precipitation from (5%) w/v, 5 ml) was added rapidly to each of the tubes which were then incubated for a further 5 minutes at 37° C. The solutions were centrifuged (1000 g, 10 minutes) and the supernatants were decanted into silica cuvettes. The absorbance of the test solution and the water blank was determined at 280 nm.

4.4.2 Degradation of Synthetic Peptides By Pepsin

The extent of the degradation of selected synthetic peptides by pepsin was followed over a period of 24 hours. Each peptide (5 mg) was dissolved in a solution (0.5 ml) containing methanol (100 µl) and hydrochloric acid (20 mM, 400 µl). Pepsin (0.1 mg) was dissolved in hydrochloric acid (20 mM, 0.5 ml) and added to each peptide solution. An aliquot (20 µl) was immediately removed from each incubation mixture and the reaction was terminated by the addition of sodium hydroxide (40 mM, 20 µl). Further aliquots (20 µl) were removed at times 10 minutes, 60 minutes, 2 hours, 6 hours, 12 hours, 18 hours and 24 hours, and the reactions were terminated by the addition of sodium hydroxide. Methanol (40 µl) was added to each of the aliquots to fully solubilise the peptides and 10 µl of each solution was analysed by reverse phase h.p.l.c.

4.4.3 Assay of Chymotrypsin Activity

The activity of the chymotrypsin solution was determined spectrophotometrically by following the hydrolysis of t-butyloxycarbonyl-L-phenylalanyl-aminomethylcoumarin (Boc-Phe-AMC). The procedure was based on the method of Zimmerman et al. (1976). In brief, an aliquot (50 µl) of Boc-Phe-AMC in methanol (0.1 mM) was added to Tris/HCl buffer (750 µl, 5 mM, pH 7.5). An aliquot (200 µl) of the chymotrypsin solution (10 mg chymotrypsin in 10 ml saline, adjusted to pH 7.5 with 0.1N sodium hydroxide) was added to the substrate and the rate of change of the absorbance at 350 nm was determined. The background hydrolysis of the substrate was measured by substituting the chymotrypsin solution for distilled water (200 µl).

4.4.4 Degradation of Synthetic Peptides by Chymotrypsin

The degradation of selected synthetic peptides was determined over a period of 24 hours. The synthetic peptides (5 mg) were each dissolved in distilled water (0.5 ml) containing methanol (10% v/v). Aliquots (200 µl) of the chymotrypsin solution prepared previously were added to each of the peptide solutions, a sample (70 µl) was immediately removed from each tube and the reaction was terminated by the addition of trifluoroacetic acid (40 µl). Further aliquots were removed at times 10 minutes, 60 minutes, 2 hours, 6 hours, 12 hours, 18 hours and 24 hours, and the reactions were terminated by the addition of trifluoroacetic acid. Methanol (40 µl) was added to each aliquot to fully solubilise the peptide and 10 µl of each solution was analysed by reverse-phase h.p.l.c.

4.4.5 Assay of Endopeptidase E.C.3.4.24.11. (Enkephalinase)

An aliquot 5 µl) of the enkephalinase stock solution was dissolved in a solution (1 ml, 0.1M Tris/HCl, pH 7.4, containing 0.1% Triton X-100 and 0.2% methanol) containing an aliquot (10 µl) of Leu-enkephalin stock solution (0.5 mM). The enzymatic degradation of the peptide was followed over a 6 hour period by h.p.l.c.

4.4.6 Degradation of Synthetic Peptides by Endopeptidase E.C.3.4.24.11 (Enkephalinase)

The degradation of selected peptides by enkephalinase was determined over a period of 24 hours. The enzyme was supplied in Tris/HCl buffer (10 mM, ph 7.4 containing 500 mM NaCl and 0.1% Triton X-100). The peptides (5 mg) were each dissolved in distilled water (0.5 ml) containing methanol (10% v/v). To an aliquot (200 µl) of each of the peptide solutions was added enkephalinase solution (60 µl). A sample (20 µl) was immediately removed from each tube and the reaction was terminated by the addition of trifluoroacetic acid (40 µl). Further aliquots were removed at times 10 minutes, 60 minutes, 2 hours, 6 hours, 12 hours, 18 hours and 24 hours, and the reactions were terminated by the addition of trifluoroacetic acid. Methanol (40 μl) was added to each aliquot before analysis by reverse-phase h.p.l.c.

4.5 Histological Studies

Male Sprague-Dawley rats (200–250 g, fasted or fed ad libitum.) were killed by cervical dislocation, the organs of interest were removed and immediately snap-frozen in liquid nitrogen. The tissue blocks were mounted on metal stubs using cryo-m-bed and sections (10 μm) were cut on a cryostat microtome (model 5030, Bright Instrument Co. Ltd., Huntingdon, U.K.). The tissue sections were mounted on coverslips precoated with chrome alum/gelatin (5% w/v gelatin, 0.5% w/v chromium potassium sulphate) and fixed for 30 minutes at room temperature using 0.04% (w/v) paraformaldehyde in phosphate buffer (0.2M, ph 7.2 containing 0.15M NaCl). The sections were washed thoroughly in water and phosphate buffer before the application of the peptide probes. The biotin labelled peptides were dissolved in phosphate buffer containing ethanol (10% v/v). Pentagastrin (1 mg) was supplied in solution (2 ml) and diluted to the required concentration with phosphate buffer. Gastrin-17 (1 mg) was suspended in water (1 ml) and solubilized by the addition of 2 drops of 1N sodium hydroxide. The solution was diluted to the required concentration with phosphate buffer. An equal volume of a solution containing enzyme inhibitors (FIG. 4.1) was added to each of the peptide solutions (100 μl). The peptide-inhibitor solutions were then applied directly to the tissue sections and the incubations were allowed to proceed for 30 minutes at room temperature. The solutions were then removed and the sections were washed thoroughly with phosphate buffer. An aliquot (200 μl) of streptavidin-fluorescein (25 μl of stock solution made up to 5 ml with phosphate buffer) was applied to each tissue section for 20 minutes at room temperature and then washed off with phosphate buffer. The coverslips with the adhered tissue sections were mounted on slides and viewed under a microscope fitted with a U.V. light source.

4.6 Materials

Materials were obtained from the following suppliers:

| | |
|---|---|
| 1% | Bacitracin |
| 10 uM | Phosphoramidon |
| 1 mM | 1-10 Phenanthroline |
| 100 uM | Phenylmethylsulphonyl fluoride (PMSF) |

The inhibitors were dissolved in Hepes buffer (10 mM, pH 7.4) containing mannitol (300 mM) and bovine serum albumin (1% w/v).

FIG. 4.1 Composition of the enzyme inhibitor solution.

Aldrich Chemical Company Ltd., Gillingham, Dorset SP8 4JL, U.K.
 m-aminobenzoic acid
 18-crown-6
 dimethyl sulphide
 N-methylmorpholine
 phosphorous pentasulphide
 sodium hydride
 trifluoroacetic acid
Argo International Ltd., Barking, Essex, U.K.
 hydrogen fluoride
Bachem AG, Hauptstrasse 144, CH-b 4416, Bubendorf, Switzerland.
 Gastrin 1-17 (human)
B.D.H. Chemicals Ltd., Poole, Dorset, U.K.
 benzyl alcohol
 L-leucine
 L-phenylalanine
 sodium iodide
 thionyl chloride
 toluene-4-sulphonic acid
 triethylamine
 L-tryptophan
East Anglia Chemicals, Hadleigh, Ipswich, Suffolk, U.K.
 acetic anhydride
Fluka AG, CH-9470, Buchs, Switzerland.
 1-aminocyclohexane carboxylic acid
 anisole
 benzyl chloroformate
 benzyl mercaptan
 Boc-L-alanine
 Boc-L-aspartic acid (4-benzyl ester)
 3-bromopropionic acid
 N-N'-dicyclohexylcarbodiimide
 di-tert-butyl dicarbonate
 HBr in acetic acid (33% v/v)
 hydroxybenzotriazole
 N-hydroxysuccinimide
 isobutyl chloroformate
 iodomethane
 L-leucinol
 methylamine (33% v/v in ethanol)
 palladium on activated charcoal (10%)
 phenylethylamine
 phenyl-3-propionic acid
 Z-L-aspartic acid (4-tert-butyl ester)
Hopkin and Williams Ltd., Chadwell Heath, Essex, U.K.
 ammonium formate
Imperial Chemical Industries Ltd., Alderley Park, Macclesfield, U.K.
 pentagastrin (Peptavlon)
Sigma Chemical Company, Poole, Dorset, U.K.
 β-alanine
 biotin p-nitrophenyl ester
 Boc-L-methionine
 chymotrypsin
 diazald (N-methyl-N-nitroso-p-toluene-sulphonamide)
 dicyclohexylamine
 haemoglobin
 indole-3-propionic acid
 Lawesson's reagent
 methyl acetate
 pepsin
 pyridine
 trifluoroacetic acid (h.p.l.c. ampoules)
Endopeptidase E.C.3.4.24.11 (enkephalinase) was a kind gift of Dr J. Nunn. Glycine ethyl ester hydrochloride was prepared by Mr S. Bates, Department of Biochemistry, Queen's University, Belfast and Boc-L-phenylalanyl-7-amino-4-methylcoumarin was prepared by Dr N. Blumsom, Department of Biochemistry, Queen's University, Belfast. Streptavidin-biotin-fluorescein was a kind gift of Dr D. Eady, Department of Medicine, Royal Victoria Hospital, Belfast.

All other chemicals were obtained from B.D.H. Chemicals Ltd., Poole, Dorset, U.K. and were of analytical grade were possible.

5.1 Synthetic Objectives

The objective of this synthetic study is to extend the structure function studies already carried out by other workers. The common C-terminal tetrapeptide, Trp-Met-Asp-Phe-NH$_2$, was used as the template for the analogues. The structure of the template was reduced to give a minimum structure which contained all the elements for receptor binding but none of the structural features which elicit the biological response. Peptide bond isosteres (thionopeptide, N-methyl and methyleneoxy) and unnatural amino acids were introduced into the shortened structure in order to confer upon it varying degrees of rotational freedom, altered hydrogen bonding properties and enzymatic resistance. The involvement of the β-carboxylic acid of aspartic acid in the binding process was investigated further by the introduction of a potent alkylating group (haloketone) of the same spatial dimensions as the carboxylic acid. The necessity of the β-bend structure for accurate receptor recognition was determined by introducing a synthetic gamma lactam unit, which is a good approximation for the β-turn, into the peptide sequence. A number of biological assays were used to assess the specificity and potency of each of the synthetic peptides.

5.2 Synthetic Considerations

5.2.1 Protecting Groups

In order to synthesize a peptide it is necessary to protect potentially reactive functional groups so as to achieve unambiguous reaction. The requirements of a protecting group are that it must be stable to the various conditions of peptide synthesis but it must be easily removed under mild conditions which do not disturb the peptide bonds.

5.2.1.1 Amino Protecting Group

Amino groups must be protected during coupling because of their vulnerability to acylation. A number of protecting groups have been developed which can be cleaved under different conditions. The three most common groups (Boc, Fmoc and Cbz) are based on urethane derivatives which are unreactive to further acylation, but can be removed under relatively mild conditions. The carbobenzoxy (Cbz or Z) group can be removed by catalytic transfer hydrogenolysis, using palladium on activated charcoal as the catalyst, or by cold HBr in acetic acid (FIG. 5.1). The t-butyloxycarbonyl (t-Boc) group is removed in the presence of anhydrous HCl or trifluoroacetic acid (FIG. 5.2). The fluorenylmethoxycarbonyl (Fmoc) group can be removed by treatment with a secondary amine, such as piperidine, in dimethylformamide (FIG. 5.3). Due to the chemical instability of the urethane protecting groups, several other protecting groups have been developed. These groups include the acetyl (CH$_3$CO—) and benzoyl (C$_6$H$_5$CO—) groups which are resistant to strong acids, hydrogenolysis (except under high temperature or pressure) and enzymatic degradation. The acetyl group is particularly useful as an N-terminal "cap" which can protect synthetic sequences from the action of N-terminal exopeptidases.

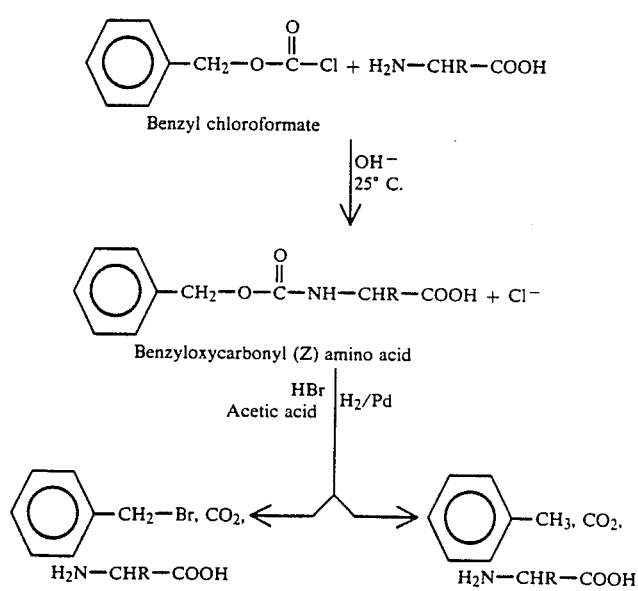

FIG. 5.1 Introduction and removal of the benzyloxycarbonyl (Z) group.

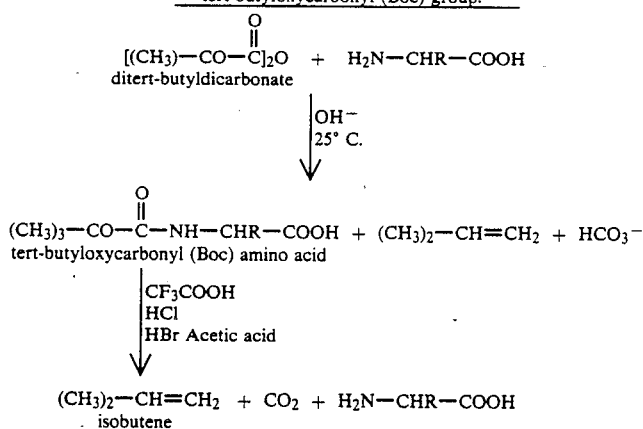

FIG. 5.2 Introduction and removal of the tert-butyloxycarbonyl (Boc) group.

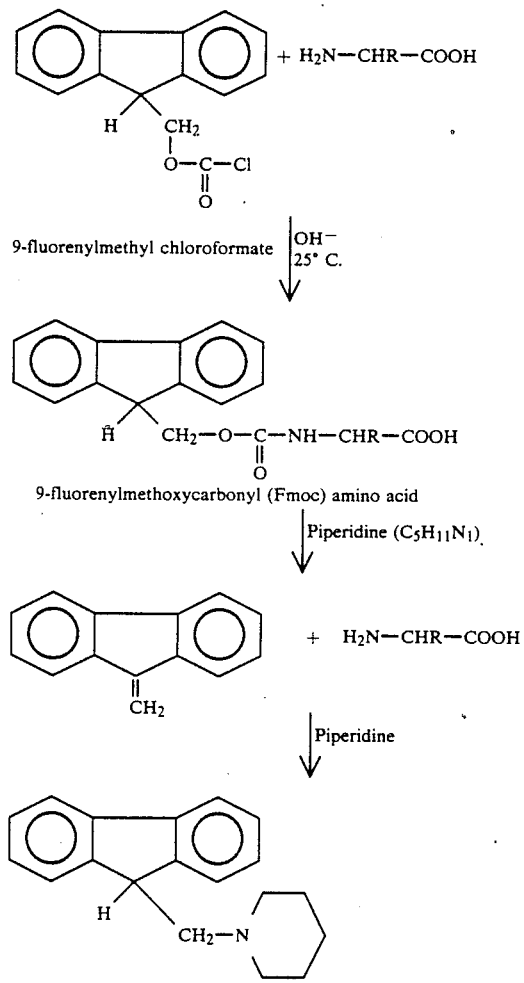

FIG. 5.3 Introduction and removal of the fluorenylmethoxycarbonyl (Fmoc) group.

5.2.1.2 Carboxyl Protecting Groups

The presence of unprotected reactive sidechain and C-terminal carboxyl groups is not desired during the formation of activated carboxyl species. These groups are invariably protected by a functional moiety which can be cleaved under specific chemical conditions. It is normal practice to utilise a carboxyl protecting group which is chemically resistant to the conditions required for the removal of the amino protecting group. The most common of the sidechain protecting groups are the tert-butyl ester, the benzyl ester and the methyl ester. The tert-butyl ester is removed in the presence of anhydrous HCl or trifluoroacetic acid although it requires a longer deprotection time than the Boc group. Benzyl esters can be removed by strong acids (HBr or HF) or catalytic transfer hydrogenolysis, although they too require a longer deprotection time. Methyl and ethyl esters are commonly removed by hydrazinolysis or mild alkali hydrolysis carried out below room temperature. Alkaline conditions may be undesirable since racemisation, hydolysis of sensitive amide bonds (e.g. elimination of ammonia from the carboxamide group of aspargine or glutamine) or cyclisation of aspartyl peptides to aspartimide derivatives can occur. The C-terminal ester may also be converted to the amide by ammonolysis (Chambers and Carpenter, 1955). Other sidechain protection methods are discussed in Bodanszky et al. (1976) and Stewart and Young (1984).

5.2.2 Formation of the Peptide Bond

All the methods of peptide formation involve activation of the carboxyl or amino groups without disturbance to the protecting groups. diethyl ether. Yield 0.53 g (64%), m.p. 79°–80° C. The product was homogeneous as judged by tlc in chloroform/methanol (4:1) (Rf 0.517) or chloroform/methanol (1:1) (Rf 0.660). (Found: C, 67.02; H, 7.82; N, 8.91. $C_{45}H_{65}O_8N_5$ requires C, 67.24; H, 8.09; N, 8.72%).

5.4.20 Preparation of tert-Butyloxycarbonyl-L-Tryptophyl-L-Leucine (Boc-Trp-Leu)

This was prepared by the method previously described (Section 5.3.9). Crystallisation was from diethyl ether/petrol ether (40°/60° C.). Yield 0.49 g (94%), m.p. 109°–111° C. The product was homogeneous as judged by tlc in chloroform/methanol (4:1) (Rf 0.315) or chloroform/methanol (1:1) (Rf 0.779). (Found: C, 63.26; H, 7.73; N, 10.21. $C_{22}H_{31}O_5N_3$ requires C, 63.31; H, 7.43; N, 10.07%).

5.4.21 (Preparation of Acetyl-L-Tryptophyl-L-Leucyl-Aspartyl-L-Phenylalanyl thioamide (AcoTrp-Leu-Asp-Phe-(t)-NH$_2$) (Peptide VII)

Boc-L-Trp-Leu-Asp(OBz) (Section 5.4.19), as the dicyclohexylamine salt (0.24 g, 3.36 mmol), was dissolved in anhydrous tetrahydrofuran (30 ml). Dicyclohexylcarbodiimide (0.07 g, 0.36 mmol), hydroxybenzotriazole (0.05 g, 0.036 mmol) and L-phenylalanyl thioamide hydrochloride (0.06 g, 0.27 mmol) were added directly to the solution. The reaction mixture was stirred overnight at room temperature. The precipitated dicyclohexylurea was removed by filtration and the solvent was removed under reduced pressure. The residue was dissolved in ethyl acetate (150 ml) and washed with 5% NaHSO$_4$, 5% NaHCO$_3$ and brine. The organic phase was dried over magnesium sulphate and reduced to near dryness. The fully protected peptide precipitated on addition of diethyl ether. Yield 0.147 g (64%).

The Boc protecting group was removed by treatment with ether/HCl (100 ml) containing anisole (0.2% v/v) for 1 hour. The hydrochloride salt was precipitated by reduction of the solution to near dryness and addition of fresh diethyl ether. The product was dissolved in a solution (10 ml) containing equal proportions of anhydrous dimethylformamide and anhydrous acetic anhydride, and left for 1 hour. On removal of the solvents in vacuo, the acetylated peptide was precipitated by the addition of diethyl ether. The benzyl ester was removed by treatment with HBr in acetic acid (33% v/v) containing anisole (0.2% v/v). On reduction to near dryness, the final product was precipitated by the addition of anhydrous diethyl ether. Yield 0.1 g (84%) m.p. 251°–252° C.

The product was homogeneous as judged by reverse phase h.p.l.c. (Found by amino acid analysis: Trp, 1; Leu, 1; Asp, 1.12; Phe, 1.)

5.4.22 Preparation of Acetyl-L-Tryptophyl-L-Leucyl-L-Aspartyl-L-Phenylalanyl thiomethylamide (Aco-Trp-Leu-Asp-Phe(t)NHCH$_3$) (Peptide VIII)

This was prepared by the method previously described (Section 5.4.21). Yield 0.215 g (62%). After full deprotection and acetylation the yield was 0.150 g (84%), m.p. 257°–258° C. (dec.). The peptide was homogeneous as judged by reverse phase h.p.l.c. (Found by amino acid analysis: Trp, 1; Leu, 1; Asp, 1; Phe, 0.9).

5.4.23 Preparation of Acetyl-L-Tryptophyl-L-Leucyl-L-Aspartylthioamide (Aco-Trp-Leo-Asp-(t)NH$_2$) (Peptide IX)

This was prepared as previously described (Section 5.4.21). Yield 0.097 g (43%). After full deprotection and acetylation the yield was 0.063 g (87%), m.p. 239°–240° C. The product was homogeneous as judged by reverse phase h.p.l.c. (Found by amino acid analysis: Trp, 1; Leu, 1; Asp, 1.05).

5.4.24 Preparation of Carbobenzoxy-L-Phenylalanyl-thiono-L-Leucyl-L-Aspartyl-L-Phenylalanylamide (Z-Phe(t)Leu-Asp-Phe-NH$_2$) (Peptide X)

Boc-L-leucyl-L-aspartyl(4 tert-butyl ester)-L-phenylalanylamide (Section 5.4.17) was fully deprotected by the addition of ether/HCl (50 ml) for 1 hour. The hydrochloride salt precipitated on removal of the solvent and the addition of fresh diethyl ether.

L-Leucyl-L-aspartyl-L-phenylalanyl-amide hydrochloride (0.1 g, 0.23 mmol) was dissolved in a solution (40 ml) containing equal proportions of tetrahydrofuran and 5% NaHCO$_3$. Z-L-phenylalanyl dithiobenzyl ester (0.26 g, 0.69 mmol) was dissolved in tetrahydrofuran (20 ml) and added to the reaction mixture. The solution was stirred for 48 hours at room temperature. The organic solvent was removed under reduced pressure and the aqueous solution was washed with diethyl ether (2×10 ml). The aqueous phase was acidified by the addition of 5% NaHSO$_4$ and the product was extracted into ethyl acetate (100 ml). The organic phase was washed with 5% NaHSO$_4$ and brine, and dried over magnesium sulphate. The solvent was reduced to near dryness and the product was precipitated by the addition of petrol ether (40°/60° C.). Yield 0.067 g (46%), m.p. 97°–99° C. The product was homogeneous as judged by tlc in chloroform/methanol (4:1) (Rf 0.752) or chloroform/methanol (1:1) (Rf 0.813). (Found by amino acid analysis: Phe, 1.9; Leu, 0.9; Asp, 1).

5.4.25 Preparation of Carbobenzoxy-L-Leucyl-thiono-L-Aspartyl-L-Phenylalanyl-amide (Z-Leu(t)Asp-Phe-NH$_2$) (Peptide XI)

This was prepared by the method previously described (Section 5.4.24). Crystallisation was from diethyl ether/petrol ether (40°/60° C.). Yield 0.05 g (17%), m.p. 282°–286° C. (dec.). The product was homogeneous as judged by tlc in chloroform/methanol (1:1) (Rf 0.847) or methanol (Rf 0.764). (Found by amino acid analysis: Leu, 1.18; Asp, 1; Phe, 1.06).

5.4.26 Preparation of Carbobenzoxy-L-Phenylalanyl-thiono-L-Leucyl-β-Alanine (Z-Phe(t)-Leu-β-Ala) (Peptide XII)

This was prepared by the method previously described (Section 5.4.24). Crystallisation was achieved by conversion to the dicylohexylamine salt and precipitation from diethyl ether/petrol ether (40°/60° C.). Yield 0.45 g (51%), m.p. 224°–227° C. (dec.). The product was homogeneous as judged by tlc in chloroform/methanol (4:1) (Rf 0.603) or chloroform/methanol (1:1) (Rf 0.726). (Found: C, 62.92; H, 8.47; N, 9.50. C$_{31}$H$_{49}$O$_5$N$_4$S$_1$ requires C, 63.16; H, 8.32; N, 9.51%).

5.4.27 Preparation of tert-Butyloxycarbonyl-L-Tryptophyl-L-Leucylthiono-β-Alanine (Boc-Trp-Leu(t)-β-Ala) (Peptide XIII)

This was prepared by the method previously described (Section 5.3.9). The product was obtained as an intractable oil but on conversion to the dicyclohexylamine salt, the peptide crystallised from diethyl ether at 4° C. Yield 0.17 g (47%), m.p. 222°–225° C. The product was homogeneous as judged by tlc in chloroform/methanol (4:1) (Rf 0.506) or chloroform/methanol (1:1) (Rf 0.738). (Found: C, 65.10; H, 8.63; N, 10.15. C$_{37}$H$_{59}$O$_5$N$_5$S$_1$ requires C, 64.82; H, 8.61; N, 10.22%).

5.5 Synthesis of N-Methyl Peptides

5.5.1 Preparation of t-Butyloxycarbonyl-N-Methyl-L-Leucine (Boc-N-Me-Leu)

This was prepared by the method of Cheung and Benoitin (1977). In brief, Boc-L-leucine (5 g, 21.6 mmol)

and methyl iodide (24.6 g, 172.8 mmol) were dissolved in anhydrous tetrahydrofuran (30 ml) and chilled to 0° C. Sodium hydride (0.26 g, 32.4 mmol) was added slowly with vigorous stirring to the solution over a period of 10 minutes. The reaction was allowed to proceed for a further 24 hours at room temperature. Ethyl acetate (50 ml) followed by water (20 ml) was added and the solution was reduced to dryness in vacuo. The residue was partitioned between diethyl (50 ml) and water (50 ml). The aqueous layer was removed and the organic layer was washed with 5% NaHCO$_3$ (50 ml). The aqueous extracts were combined and acidified by the addition of 5% NaHSO$_4$. The product was extracted into ethyl acetate (100 ml) and washed successively with water (2×50 ml), 10% Na$_2$S$_2$O$_3$ (2×50 ml) and water (100 ml). The organic layer was dried over magnesium sulphate and reduced to dryness. The product was obtained as a pale yellow oil which solidified at −20° C. Yield 4.69 g (88%), m.p. 53°-55° C. (lit. 56°-57° C., Cheung and Benoiton, 1977). The product was homogeneous as judged by tlc in chloroform/methanol (4:1) (Rf 0.375) or chloroform/methanol (1:1) (Rf 0.683). (Found: C, 58.47; H, 9.19; N, 5.71. C$_{12}$H$_{23}$O$_4$N$_1$ requires C, 59.77; H, 9.38; N, 5.71%). $^1$H n.m.r. (p.p.m) CDCl$_3$ δ 0.98 (6H, α, (CH$_3$)$_2$), 1.5 (9H, s, C(CH$_3$)$_3$), 1.82 (3H, m, CH$_2$CH), 2.84 (3H, s, N—CH$_3$), 9.94 (1H, s, COOH).

5.5.2 Preparation of t-Butyloxycarbonyl-β-Alanine (Boc-β-Ala)

This was prepared as previously described (Section 5.3.1). Crystallisation was from ethyl acetate/petrol ether (60°/80° C.). Yield 8.05 g (61%), m.p. 75°-77° C. (Lit. 76°-78° C., Fujino and Hatanaka, 1967). The product was homogeneous by tlc in chloroform/methanol (4:1) (Rf 0.587) or chloroform/methanol (1:1) (Rf 0.716). (Found: C, 51.02; H, 7.95; N, 7.37. C$_8$H$_{15}$O$_4$N$_1$ requires C, 50.79; H, 7.41; N, 7.41%).

5.5.3 Preparation of t-Butyloxycarbonyl-N-methyl-β-Alanine (Boc-N-Me-β-Ala)

This was prepared by the method previously described (Section 5.5.1). The product solidified as a wax at −20° C. Yield 1.36 g (42%). The product was homogeneous as judged by tlc in chloroform/methanol (4:1) (Rf 0.816) or chloroform/methanol (1:1) (Rf 0.768). (Found: C, 71.64; H, 8.41; N, 7.03. C$_9$H$_{17}$O$_4$N$_1$ requires C, 71.64; H, 8.46; N, 6.96%). $^1$H n.m.r. (p.p.m.) CDCl$_3$ δ 1.44 (9H, s, C(CH$_3$)$_3$), 2.56 (2H, t, C$_\alpha$H$_2$), 2.85 (3H, s, N—CH$_3$), 3.46 (2H, t, C$_\beta$H$_2$), 10.48 (1H, s, COOH).

5.5.4 Preparation of t-Butyloxycarbonyl-N-Methyl-L-Leucyl-β-Alanine benzyl ester (Boc-N-Me-Leu-β-Ala-OBzl)

This was prepared by the method previously described (Section 5.3.11). The product was obtained as a clear oil. Yield 1.02 g (88%). It was homogeneous as judged by tlc in chloroform/methanol (4:1) (Rf 0.658) or ethyl acetate/cyclohexane (1:1) (Rf 0.209). (Found: C, 64.79; H, 8.49; N, 6.88. C$_{22}$H$_{34}$O$_5$N$_2$ requires C, 65.02; H, 8.37; N, 6.89%).

5.5.5 Preparation of Phenyl-3-propionyl-N-methyl-L-Leucyl-β-Alanine (PPA-N-Me-Leu-β-Ala) Peptide XIV The previous compound was deprotected in ether/HCl for 1 hour. The hydrochloride salt was obtained as a hygroscopic foam on removal of the ether/HCl and the addition of fresh diethyl ether. Phenyl-3-propionic acid was coupled to the dipeptide by the mixed anhydride procedure (Section 5.3.11). The product was obtained as a pale yellow oil Yield 0.83 g (75%).

The benzyl ester was removed by catalytic transfer hydrogenolysis (Section 5.3.12). The peptide was crystallized by conversion to the dicyclohexylamine salt and the addition of diethyl ether. Yield 0.58 g (60%), m.p. 92°-94° C. The product was homogeneous as judged by tlc in chloroform/methanol (4:1) (0.536) or chloroform/methanol (1:1) (0.569). (Found: C, 70.35; H, 9.58; N, 7.95. C$_{31}$H$_{51}$O$_4$N$_3$ requires C, 70,32; H, 9.64; N, 7.94%).

5.5.6 Preparation of t-Butyloxycarbonyl-L-Leucyl-N-methyl-β-Alanine (Boc-Leu-N-Me-β-Ala)

Compound 5.5.3 was deprotected in ether/HCl for 2 hours. On removal of the solvent, the hydrochloride salt was obtained as a hygroscopic foam. Boc-L-leucine was coupled to the amino acid by the N-hydroxysuccinimide ester method (Section 5.3.9). The product was obtained as a clear oil. Yield 1.34 g (95%). The peptide was homogeneous as judged by tlc in chloroform/methanol (4:1) (Rf 0.617) or chloroform/methanol (1:1) (Rf 0.578). (Found: C, 56.91; H, 9.23; N, 8.86, C$_{15}$H$_{28}$O$_5$N$_2$ requires C, 56.96; H, 8.86; N, 8.86%).

5.5.7 Preparation of Phenyl-3-propionyl-L-Leucyl-N-Methyl-β-Alanine (PPA-Leu-N-Me-β-Ala) (Peptide XV)

The previous compound was deprotected for 1 hour in a saturated solution of HCl in diethyl ether. On removal of the solvent, the hydrochloride salt was obtained as a hygroscopic foam.

Phenyl-3-propionic acid was coupled to the peptide by the N-hydroxysuccinimide ester method (Section 5.3.9). The resulting oil was crystallised by conversion to the dicyclohexylamine salt and the addition of diethyl ether. Yield 1.02 g (63%), m.p. 194°-196° C. The product was homogeneous as judged by tlc in chloroform/methanol (4:1) (Rf 0.710) or chloroform/methanol (1:1) (Rf 0.488). (Found: C, 70.39; H, 9.85; N, 8.02. C$_{31}$H$_{51}$O$_4$N$_3$ requires C, 70.32; H, 9.64; N, 7.94%).

5.5.8 Preparation of t-Butyloxycarbonyl-N-Methyl-L-Leucine-N-Hydroxysuccinimide ester (Boc-N-Me-Leu-OSu)

This was prepared by the method previously described (Section 5.3.4). The ester was obtained as an intractable oil. Yield 2.68 g (67%). The product was homogeneous as judged by tlc in chloroform/methanol (4:1) (Rf 0.753) or chloroform/methanol (1:1) (Rf 0.371). Found: C, 55.92; H, 7.72; N, 8.31. C$_{16}$H$_{26}$O$_6$N$_2$ requires C, 56.14; H, 7.60; N, 8.19%).

5.5.9 Preparation of t-Butyloxycarbonyl-N-Methyl-L-Leucyl-N-Methyl-β-Alanine (Boc-N-Me-Leu-N-Me-β-Ala)

Boc-N-methyl-leucine was coupled to the hydrochloride salt of N-Me-β-alanine (Section 5.5.3) by the N-hydroxysuccinimide ester method (Section 5.3.8). The product was obtained as an intractable oil. Yield 1:1 g (57%). The dipeptide was homogeneous as judged by tlc in chloroform/methanol (4:1) (Rf 0.712) or chloroform/methanol (1:1) (Rf 0.610). (Found: C, 58.29; H, 8.29; N, 8.82. $C_{16}H_{30}O_5N_2$ requires C, 58.18; H, 8.48; N, 9.09%).

5.5.10 Preparation of Phenyl-3-propionyl-N-Methyl-L-Leucyl-N-Methyl-βAlanine (PPA-N-Me-Leu-N-Me-β-Ala) (Peptide XVI)

The previous compound was deprotected in ether/HCl for 2 hours. On removal of the solvents, the hydrochloride salt was obtained as a clear oil.

Phenyl-3-propionic acid was coupled to the dipeptide by the method previously described (Section 5.3.9). The resulting oil was crystallised by conversion to the dicyclohexylamine salt. Yield 0.3 g (18%), m.p. 107°–111° C. The product was homogeneous as judged by tlc in chloroform/methanol (4:1) (Rf 0.366) or chloroform/methanol (1:1) (Rf 0.609). (Found: C, 70.57; H, 9.72; N, 7.91. $C_{32}H_{53}O_4N_3$ requires C, 70.72; H, 9.76; N, 7.73%).

5.6 Synthesis of the Methyleneoxy Pseudopeptide

5.6.1 Preparation of t-Butyloxycarbonyl-L-Leucinol (Boc-LeuOL)

This was prepared by the method previously described (Section 5.3.1). The product was obtained as a clear oil. Yield 5.23 g (94%). The product was homogeneous as judged by tlc in chloroform/methanol (1:1) (Rf 0.431) or methanol (Rf 0.643). (Found: C, 60.83; H, 10.42; N, 6.39. $C_{11}H_{23}O_3N_1$ requires C, 60.83; H, 10.60; N, 6.45%).

5.6.2 Preparation of 3-Bromopropionyl methyl ester

Thionyl chloride (9.3 ml, 128 mmol) was dripped slowly into chilled anhydrous methanol (50 ml). After 15 minutes, 3-bromo-propionic acid (5 g, 32 mmol) was added and the solution was allowed to warm to room temperature overnight. The solvent was removed under reduced pressure and the residue was taken up in ethyl acetate (100 ml). The solution was washed with 5% NaHCO$_3$ and brine. The organic layer was dried over magnesium sulphate and evaporated to dryness. The product was obtained as an intractable yellow oil. Yield 4.79 g (88%). The derivatives was homogeneous as judged by tlc in chloroform/methanol (4:1) (Rf 0.842) or chloroform/methanol (1:1) (Rf 0.825). (Found: C, 28.72; H, 3,96; Br, 47.72. $C_4H_7O_2Br_1$ requires C, 28.74; H, 4.19; Br, 47.90%.)

5.6.3 Preparation of t-Butyloxycarbonyl-L-Leucylψ(CH$_2$O)-β-Alanine (Boc-Leuψ(CH$_2$O)-β-Ala)

This was prepared by the method of Rubini et al. (1986). In brief, to a stirred solution of Boc-leucinol (1 g, 4.6 mmol) under a nitrogen atmosphere in anhydrous tetrahydrofuran (50 ml) at 0° C., was added sodium hydride (0.55 g, 13.8 mmol). The reaction was stirred for 30 minutes after which time 18-crown-6 (1.22 g, 4.6 mmol) was added followed by 3-bromopropionyl methyl ester (3.07 g, 18.4 mmol). The reaction was stirred for 1 hour at 0° C. and then overnight at room temperature. Ethyl acetate (10 ml) was added followed by water (10 ml) and acetic acid to adjust the pH to 6.5–7.0. The solvent was removed in vacuo. and the residue was dissolved in ethyl acetate (100 ml). The organic solution was washed successively with 5% NaHSO$_4$, brine and water, and then dried over magnesium sulphate. On reduction to dryness a yellow oil was obtained. The dipeptide was deprotected for 1 hour in ether/HCl. The solvent was removed and the residue was dissolved in 1N HCl and washed with diethyl ether (2×50 ml). The aqueous phase was reduced in vacuo, and the hydrochloride salt was precipitated by the addition of diethyl ether. Yield 0.32 g (31%). The product was homogeneous as judged by tlc in chloroform/methanol (1:1) (Rf 0.552) or methanol (Rf 0.586). (Found: C, 48.21; H, 8.86; N, 6.23. $C_9H_{20}O_3N_1Cl_1$ requires C, 48.0; H, 8.88; N, 6.22%).

5.6.4 Preparation of Phenyl-3-Propionyl-L-Leucyl-ψ(CH$_2$O)-β-Alanine (PPA-Leuψ(CH$_2$O)-β-Ala) (Peptide XVII)

This was prepared by the method previously described (Section 5.3.9). The tripeptide was obtained as an intractable oil and crystallised by conversion to the dicylcohexylamine salt. Yield 0.29 g (44%), m.p. 84°–87° C. The product was homogeneous as judged by tlc in chloroform/methanol (4:1) (Rf 0.631) or chloroform/methanol (1:1) (Rf 0.629). Found: C, 71.45; H, 9.89; N, 5.42. $C_{30}H_{50}O_4N_2$ requires C, 71.71; H, 9.96; N, 5.57%).

5.7 Synthesis of Haloketone Containing Peptides

5.7.1 Preparation of t-Butyloxycarbonyl-L-Tryptophyl-L-Leucyl-β-Alanyldiazomethane (Boc-Trp-Leu-β-Ala-COCHN$_2$)

Diazomethane was prepared as an ethereal solution (Section 4.1.1). Boc-tryptophyl-leucyl-β-alanine (Section 5.3.9) was coupled to this by means of the mixed anhydride procedure (5.3.11). The peptide was obtained as a clear oil which solidified at 4° C. to yield a low melting point solid. Yield 0.24 g (96%). The product was homogeneous as judged by tlc in chloroform/methanol (4:1) (Rf 0.701) or chloroform/methanol (1:1) (Rf 0.725). (Found: C, 61.09; H, 7.21; N, 16.32. $C_{26}H_{36}O_5N_6$ requires C, 60.93; H, 7.03; N, 16.41%).

5.7.2 Preparation of Phenyl-3-propionyl-L-Leucyl-β-Alanyldiazomethane (PPA-Leu-β-Ala COCHN$_2$)

This was prepared by the method previously described (Section 5.7.1). The peptide was obtained as a clear oil which solidified at 4° C. to give a wax. Yield 0.57 g (82%). The product was homogeneous as determined by tlc in chloroform/methanol (4:1) (Rf 0.631) or chloroform/methanol (1:1) (Rf 0.587). (Found: C, 63.41; H, 7.20; N, 15.69. $C_{19}26O_3N_4$ requires C, 63.68; H, 7.26; N, 15.64%).

5.7.3 Preparation of t-Butyloxycarbonyl-L-Tryptophyl-L-Leucyl-β-Alanylchloromethane (Boc-Trp-Leu-β-Ala-COCH$_2$Cl) (Peptide XVIII)

Boc-tryptophyl-leucyl-β-alanyl-diazomethane (Section 5.7.1) (0.24 g, 0.47 mmol) was dissolved in ethyl acetate (50 ml). Ether/HCl (40 ml) was added followed by 5% NaHCO$_3$ (60 ml) 1 minute later. The mixture was agitated to neutralise the acid and the aqueous layer was removed. The organic phase was dried over magnesium sulphate and reduced to dryness. The peptide was recrystallised from ethyl acetate/petrol ether (40°/60° C.) and then diethyl ether/petrol ether (40°/60° C.). Yield 0.2 g (82%), m.p. 79°–81° C. The product was homogeneous as judged by tlc in chloroform/methanol (4:1) (Rf 0.770) or chloroform/methanol (1:1) (Rf 0.777). (Found: C, 59.83; H, 7.35; N, 10.81. $C_{26}H_{37}O_5N_4Cl_1$ requires C, 60.00; H, 7.11; N, 10.77%).

5.7.4 Preparation of Phenyl-3-propionyl-L-Leucyl-β-Alanylchloromethane (PPA-Leu-β-Ala-COCH$_2$Cl) (Peptide XIX)

This was prepared by the method previously described (Section 5.7.2). A white precipitate was obtained on removal of the solvents and this was purified by preparative hplc. Yield 0.09 g (54%), m.p. 105°–107° C. The product was homogeneous as judged by tlc in chloroform/methanol (4:1) (Rf 0.726) or chloroform/methanol (1:1) (Rf 0.695). (Found: C, 62.42; H, 7.35; N, 7.52. C$_{19}$H$_{27}$O$_3$N$_2$Cl$_1$ requires C, 62.29; H, 7.37; N, 7.65%).

5.7.5 Preparation of Phenyl-3-propionyl-L-Leucyl-β-Alanylfluoromethane (PPA-Leu-β-Ala-COCH$_2$F) (Peptide XX)

Phenyl-3-propionyl-leucyl-β-alanyl-diazomethane (5.9.2) (0.38 g, 1.06 mmol) was stirred with condensed, anhydrous HF (5 ml) for 10 minutes. The HF was removed under reduced pressure and the resulting waxy solid was dried over potassium hydroxide pellets. Yield 0.25 g (65%). The product was homogeneous as judged by tlc in chloroform/methanol (4:1) (Rf 0.734) or chloroform/methanol (1:1) (Rf 0.738), (Found: C, 64.83; H, 7.82; N, 8.19. C$_{19}$H$_{27}$O$_3$N$_2$F$_1$ requires C, 65.14; H, 7.71; N, 8.00%).

5.8 Synthesis of the Ketomethylene amino Pseudopeptide

5.8.1 Preparation of t-Butyloxycarbonyl-L-Leucyl-diazomethane (Boc-Leu-COCHN$_2$)

This was prepared by the method previously described (Section 5.7.1). The product crystallised at 4° C. and was obtained as pale yellow plates. Yield 2.6 g (86%), m.p. 72°–74° C. The product was homogeneous as judged by tlc in chloroform/methanol (1:1) (Rf 0.769) or chloroform/methanol (95:5) (Rf 0.540). (Found: C, 56.51; H, 8.25; N, 16.43. C$_{12}$H$_{21}$O$_3$N$_3$ requires C, 56,47; H, 8.23; N, 16.47%).

5.8.2 Preparation of L-Leucyl-chloromethane hydrochloride (Leu-COCH$_2$Cl)

The previous compound was deprotected and converted to the chloromethyl ketone by treatment with ether/HCl for 1 hour. When the solvent was removed under reduced pressure and fresh ether was added, the product was obtained as a white powder in quantitative yield. Yield 1.56 g (100%), m.p. 126°–128° C. The product was homogeneous as judged by tlc in chloroform/methanol (95:5) (Rf 0.00). (Found: C, 42.04; H, 7.53; N, 6.96. C$_7$H$_{15}$O$_1$N$_1$Cl$_1$ requires C, 42.21; H, 7.53; N, 7.03%).

5.8.3 Preparation of t-Butyloxycarbonyl-L-Tryptophyl-L-Leucyl-chloromethane (Boc-Trp-Leu-COCH$_2$Cl)

Boc-L-tryptophan (2.22 g, 7.3 mmol) was dissolved in anhydrous tetrahydrofuran (30 ml). The solution was chilled to −15° C. and N-methylmorpholine (1.62 ml, 14.6 mmol) was added followed by isobutyl chloroformate (0.99 ml, 7.66 mmol). The solution was stirred for 15 minutes after which time L-leucyl-chloromethyl ketone hydrochloride (1.32 g, 6.63 mmol) in anhydrous dimethylformamide (20 ml) was added. The reaction mixture was allowed to warm to room temperature over a period of 4 hours and the solvent was removed in vacuo. The residue was dissolved in ethyl acetate (150 ml) and washed quickly with 5% NaHSO$_4$, 5% NaHCO$_3$ and brine. The organic layer was dried over magnesium sulphate and then reduced to dryness. Crystallisation was from diethyl ether/petrol ether (40°/60° C.). Yield 1.87 g (60%), m.p. 140°–141° C. The product was homogeneous as judged by tlc in chloroform/methanol (4:1) (Rf 0.736) or chloroform/methanol (95.5) (Rf 0.490). (Found: C, 61.43; H, 7.10; N, 9.37. C$_{23}$H$_{32}$O$_4$N$_3$Cl$_1$ requires C, 61.47; H, 7.12; N, 9.35%).

5.8.4 Preparation of L-Tryptophyl-L-Leucyl-ψ(COCH$_2$NH)-L-Aspartyl-L-Phenylalanyl amide dihydrochloride (Trp-Leu-ψ(-COCH$_2$NH-)-Asp-Phe-NH$_2$) (Peptide XXI)

Boc-L-tryptophyl-L-leucyl-chloromethane (Section 5.7.3) (0.6 g, 1.34 mmol) was dissolved in a solution (50ml) containing equal volumes of tetrahydrofuran and 5% NaHCO$_3$. Sodium iodide (0.6 g, 4.02 mmol) was added and the reaction was allowed to proceed for 30 minutes. As the iodomethylketone was formed, the solution changed colour from yellow to white. The dipeptide, L-aspartyl(t-butyl ester)-L-phenylalanyl amide (Section 5.4.16) (0.15 g, 0.44 mmol) was added directly to the reaction and the solution was stirred overnight at room temperature. The organic solvent was removed under reduced pressure and ethyl acetate (150 ml) was added. The solution was agitated and the aqueous phase was removed. The organic layer was washed quickly with 5% NaHSO$_4$ and water, and dried over magnesium sulphate. The solvent was removed under reduced pressure and the precipitate was washed copiously with diethyl ether. Yield 0.139 g (42%), m.p. 124°–126° C. The fully protected peptide was homogeneous as judged by tlc in chloroform/methanol (4:1) (Rf 0.764) or chloroform/methanol (1:1) (Rf 0.793).

The protecting groups were removed by treatment with ether/HCl containing 0.2% (v/v) anisole for 1 hour. The dihydrochloride salt was obtained in quantitative yield. Yield 0.32 g (100%), m.p. 188°–190° C. The product was homogeneous as judged by reverse phase hplc. (Found: C, 55.82; H, 6.19; N, 12.49. C$_{31}$H$_{42}$O$_6$N$_6$Cl$_2$ requires C, 56.02; H, 6.32; N, 12.65%).

5.9 Synthesis of the γ-Lactam Containing Peptide

5.9.1 Preparation of t-Butyloxycarbonyl-L-Methionyl-Glycine ethyl ester (Boc-Met-Gly-OEt)

This was prepared by the method previously described (Section 5.3.11). The dipeptide was obtained as a clear oil which solidified to a wax at −20° C. Yield 2.82 g (70%). The product was homogeneous as judged by tlc in chloroform/methanol (4:1) (Rf 0.730) or chloroform/methanol (1:1) (Rf 0.648). (Found: C, 50.03; H, 7.67; N, 8.29. C$_{14}$H$_{26}$O$_5$N$_2$S$_1$ requires C, 50.29; H, 7.78; N, 8.38%).

5.9.2 Preparation of t-Butyloxycarbonyl-L-Methionyl-Glycine ethyl ester-methylsulphonium iodide The previous compound (5.8.1) (2.74 g, 8.2 mmol) was dissolved in methyl iodide (20 ml) and stirred overnight at room temperature. The solvent was removed under reduced pressure and the resulting yellow foam was washed with anhydrous diethyl ether. The methylsulphonium iodide salt was obtained as a hygroscopic yellow foam. Yield (3.48 g (89%). The produce was homogeneous as judged by tlc in chloroform/methanol (4:1) (Rf 0.246). $^1$H n.m.r. (p.p.m.) CDCl$_3$DMSO. δ 1.35 (9 H, S, C(CH$_3$)$_3$), 2.88 (6H, S, S(CH$_3$)$_2$).

5.9.3 Preparation of (S)-3[t-Butyloxycarbonyl-amino]-2-oxo-1-pyrrolidine acetic acid The previous compound (Section 5.8.4) (3.38 g, 7.1 mmol) was dissolved in a solution (30 ml) containing equal proportions of anhydrous dimethylformamide and dichloromethane, and chilled to 0° C. The solution was contained under a stream of nitrogen gas and sodium hydride (0.6 g, 14.2 mmol) was added slowly. The reaction was allowed to proceed for a further 3 hours after which time methyl acetate (100 ml) and water (30 ml) were added. The solution was stirred overnight at room temperature. The solvents were removed in vacuo, and the residue was partitioned between water (50 ml) and ethyl acetate (50 ml). The aqueous layer was removed and acidified by the addition of 5% NaHSO$_4$. The precipitate was extracted into ethyl acetate (200 ml) and washed with 5% NaHSO$_4$. The organic layer was dried over magnesium sulphate and the solvent was removed under reduced pressure. The residue was dissolved in diethyl ether and the product precipitated on addition of petrol ether (40°/60° C.). Yield 0.72 g (39%), m.p. 62°–64° C. The product was homogeneous as judged by tlc in chloroform/methanol (4:1) (Rf 0.049) or chloroform/methanol (1:1) (Rf 0.479). (Found: C, 50.87; H, 6.92; N, 10.61. C$_{11}$H$_{18}$O$_5$N$_2$ requires C, 51.16; H, 6.97; N, 10.85%).

5.9.4 Preparation of t-Butyloxycarbonyl-L-Aspartyl(4-benzyl ester)-L-Phenylalanyl amide (Boc-Asp(OBzl)-Phe-NH$_2$)

This was prepared by the method previously described (Section 5.3.11). Crystalliszation was from ethyl acetate/petrol ether (40°/60° C.). Yield 3.31 g (94%), m.p. 123°–125° C. The product was homogeneous as judged by tlc in chloroform/methanol (4:1) (Rf 0.720) or chloroform/methanol (1:1) (Rf 0.742). (Found: C, 64.02; H, 6.61; N, 8.90. C$_{25}$H$_{31}$O$_6$N$_3$ requires C, 63.96; H, 6.61; N, 8.95%).

5.9.5 Preparation of t-Butyloxycarbonyl-L-Leucyl-L-Aspartyl(4-benzyl ester)-L-Phenylalanyl amide (Boc-Leu-Asp(OBzl)-Phe-NH$_2$)

The previous compound (Section 5.8.4) was deprotected in ether/HCl for 1 hour. The hydrochloride salt precipitated on removal of the solvents and addition of fresh diethyl ether.

Boc-leucine was coupled to the dipeptide by the method previously described (Section 5.3.11). The tripeptide was recrystallised from diethyl ether/petrol ether (40°/60° C.). Yield 0.99 g (46%, m.p. 108°–111° C. The product was homogeneous as judged by tlc in chloroform/methanol (4:1) (Rf 0.686) or chloroform/methanol (1:1) (Rf 0.657). (Found: C, 63.89; H, 7.31; N, 9.62. C$_{31}$H$_{42}$O$_7$N$_4$ requires C, 63.92; H, 7.22; N, 9.62%).

5.9.6 Preparation of t-Butyloxycarbonyl-L-Tryptophyl-L-Leucyl-L-Aspartyl (4-benzyl ester)-L-Phenylalanyl amide (Boc-Trp-Leu-Asp(OBzl)-Phe-NH$_2$)

The previous compound was deprotected in ether/HCl for 1 hour. The hydrochloride salt was obtained on removal of the solvent and addition of fresh diethyl ether.

Boc-tryptophan was coupled to the tripeptide by the method previously described (5.3.11). The tetrapeptide was recrystallised from ethyl acetate/petrol ether (40°/60° C.). Yield 0.9 g (82%), m.p. 131°–134° C. The product was homogeneous as judged by tlc in chloroform/methanol (4:1) (Rf 0.806) or chloroform/methanol (1:1) (Rf 0.741). (Found: C, 65.77; H, 6.79; N, 10.89. C$_{42}$H$_{52}$O$_8$N$_6$ requires C, 65.62; H, 6.77; N, 10.93%).

5.9.7 Preparation of t-Butyloxycarbonyl-amino-2-oxo-1-pyrrolidineacetyl-L-Tryptophyl-L-Leucyl-L-Aspartyl (4-benzyl ester)-L-Phenylalanine amide The previous compound was deprotected in ether/HCl containing 0.2% (v/v) anisole for 1 hour. The hydrochloride salt precipitated on addition of diethyl ether.

The protected gamma-lactam (Section 5.8.3) was coupled to the deprotected tetrapeptide by the method previously described (Section 5.3.11). The peptide was precipitated from ethyl acetate by the addition of petrol ether (40°/60° C.). Yield 0.26 g (51%) m.p. 124°–126° C. The product was homogeneous as judged by tlc in chloroform/methanol (4:1) (Rf 0.650) or chloroform/methanol (1:1) (Rf 0.753).

5.9.8 Preparation of t-Butyloxycarbonyl-L-Alanyl-amino-2-oxo-1-pyrrolidineacetyl-L-Tryptophyl-L-Leucyl-L-Aspartyl-L-Phenylalanyl amide (Peptide XXII)

The previous compound was deprotected in ether/HCl containing 0.2% (v/v) anisole for 1 hour. The hydrochloride salt precipitated on addition of diethyl ether.

Boc-alanine was coupled to the deprotected peptide by the method previously described (Section 5.3.11). The protected product was precipitated from ethyl acetate by the addition of diethyl ether. Yield 0.1 g (52%). The product was homogeneous as judged by tlc in chloroform/methanol (4:1) (Rf 0.652) or chloroform/methanol (1:1) (Rf 0.782). The benzyl ester was removed by catalytic transfer hydrogenolysis (Section 5.3.12). The deprotected peptide was precipitated from ethanol by the addition of diethyl ether. Yield 0.07 g (80%), m.p. 191°–193° C. The deprotected product was homogeneous as judged by tlc in chloroform/methanol (4:1) (Rf 0.642) or chloroform/methanol (1:1) (Rf 0.793). (Found by amino acid analysis: Ala, 1; lactam:1; Trp;, 0.95; Leu, 1; Asp 1.05; Phe, 1).

5.10 Synthesis of Biotinylated Peptides

5.10.1 Preparation of Biotinyl-L-Tryptophyl-L-Leucyl-β-Alanine (Biotin-Trp-Leu-β-Ala) (Peptide XXIII)

Boc-L-trypotphyl-L-leucyl-β-Alanine (5.3.9) was deprotected by treatment with ether/HCl containing 0.2% (v/v) anisole for 1 hour. On removal of the solvent and addition of anhydrous diethyl ether, the hydrochloride salt precipitated in near quantitative yield (0.12 g, 96%).

The deprotected tripeptide (0.12 g, 0.3 mmol) was dissolved in anhydrous dimethylformamide (20 ml). Biotin-nitrophenyl ester (0.1 g, 0.28 mmol), hydroxybenzotriazole (4 mg, 0.03 mmol) and N-methylmorpholine (0.04 ml, 0.3 mmol) were added directly to the solution and the reaction was allowed to proceed overnight at room temperature. The solvent was removed in vacuo, and the residue was dissolved in 5% $NaHCO_3$ (30 ml). The aqueous phase was washed with ethyl acetate (2×15 ml) and acidified by the addition of 5% $NaHSO_4$. The precipitate was extracted into ethyl acetate (100 ml) and the organic layer was dried over magnesium sulphate. The solution was reduced to near dryness and the product was precipitated by the addition of petrol ether (40°/60° C.). Yield 0.04 g (21%), m.p. 130°–131° C. The product was homogeneous as judged by tlc in chloroform/methanol (4:1) (Rf 0.087) or chloroform/methanol (1:1) (Rf 0.573). (Found: C, 58.67; H, 6.62; N, 13.75. $C_{30}H_{42}O_6N_6S_1$ requires C, 58.63; H, 6.84; N, 13.68%).

5.10.2 Preparation of Biotinyl-L-tryptophyl-L-Leucyl-β-Alanylfluoromethane (Biotin-Trp-Leu-β-Ala-COCH₂F) (Peptide XXIV)

Boc-L-tryptophyl-L-leucyl-β-Alanyl-diazomethane (Section 5.9.1) (0.21 g, 0.41 mmol) was dissolved in dimethylsulphide (10ml) and anhydrous HF (5ml) was condensed into the solution. The reaction was allowed to proceed for 10 minutes after which time the solvents were removed under vacuum. The fluoromethyl ketone, as the hydrofluoride salt, was precipitated by the addition of diethyl ether. Yield 0.14 g (78%).

Biotin was coupled to the fluoromethyl ketone by the method previously described (Section 5.10.1). The biotinylated peptide was precipitated from ethyl acetate by the addition of petrol ether (40°/60° C.) Yield 0.04 g (20%), m.p. 95°–97° C. The product was homogeneous as judged by tlc in chloroform/methanol (4:1) (Rf 0.726) or methanol (Rf 0.715). (Found: C, 59.27; H, 6.97; N, 13.20. $C_{31}H_{44}O_5N_6S_1F_1$ requires C, 58.95; H, 6.97; N, 13.31%).

RESULTS AND DISCUSSION

6.1 Introduction

The biological activity of some of the analogues prepared in this synthetic study (Table 6.1) was assessed by means of several assays. The peptides were initially tested in vivo as modulators of gastrin or histamine stimulated acid secretion and gastrin-stimulated pepsin secretion. The most promising antagonists were then assessed in vitro for their cross-reactivity with cholecystokinin receptors by studying their effect on amylase secretion from isolated pancreatic acini. Preliminary stability studies were carried out in the presence of strong acid, pepsin, chymotrypsin and E.C.3.4.24.11 to assess the potential bioavailability of selected peptides when administered orally. Finally, the location of receptors for one of the analogues was determined within rat gastrointestinal mucosa utilising the biotin-streptavidin interaction.

6.2 Acid Secretory Studies

6.2.1 Introduction

Several of the analogues prepared in this synthetic study (Table 6.1) were tested in vivo as potential modulators of gastric acid secretion in the rat and the dog using three model systems (Section 4.3). Each analogue was administered in the presence or absence of a stimulant (pentagastrin, gastrin-17 or histamine) and the biological effect of the analogue was expressed in terms of the acid secretion during the period of administration of the analogue.

TABLE 6.1

The synthetic peptides prepared in this study

| PEPTIDE | SEQUENCE |
|---|---|
| I | Boc—Trp—Leu—B—Ala |
| II | PPA—Leu—B—Ala |
| III | IPA—Leu—B—Ala |
| IV | PPA—cHEX—B—Ala |
| V | IPA—Leu—Asp—PEA |
| VI | Boc—Trp—Leu—Asp—mABA—OMe |
| VII | AcO—Trp—Leu—Asp—Phe(t)NH₂ |
| VIII | AcO—Trp—Leu—Asp—Phe(t)NHCH₃ |
| IX | AcO—Trp—Leu—Asp(t)NH₂ |
| X | Z—Phe(t)—Leu—Asp—Phe—NH₂ |
| XI | Z—Leu(t)—Asp—Phe—NH₂ |
| XII | Z—Phe(t)—Leu—B—Ala |
| XIII | Boc—Trp—Leu(t)—B—Ala |
| XIV | PPA—N—Me—Leu—B—Ala |
| XV | PPA—Leu—N—Me—B—Ala |
| XVI | PPA—N—Me—Leu—N—Me—B—Ala |
| XVII | PPA—Leuψ(CH₂O)—B—Ala |
| XVIII | Boc—Trp—Leu—B—Ala—COCH₂Cl |
| XIX | PPA—Leu—B—Ala—COCH₂Cl |
| XX | PPA—Leu—B—Ala—COCH₂F |
| XXI | Trp—Leuψ(COCH₂NH)—Asp—Phe—NH₂ |

XXII

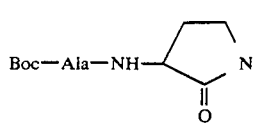

XXIII Biotinyl—Trp—Leu—B—Ala

TABLE 6.1-continued

The synthetic peptides prepared in this study

| PEPTIDE | SEQUENCE |
|---|---|
| XXIV | Biotinyl—Trp—Leu—B—Ala—COCH$_2$F |

6.2.2 The Response of the Rat Stomach to Analogues of the C-terminal Region of Gastrin Two rat models (Section 4.3) were used to test several of the synthetic analogues. The first study was carried out with peptides I (Boc-Trp-Leu-$\beta$-Ala) and XXII (Boc-Ala-amino-1-oxo-1-pyrrolidine-actyl-Trp-Leu-Asp-Phe-NH$_2$) using a simple ligated stomach model. The results for both peptides are summarised in Table 6.2. Peptide I is a potent antagonist of pentagastrin stimulated acid secretion when administered at a dose of 8.2 nmol.Kg$^{-1}$. The acid secretion in the presence of the analogue and pentagastrin is reduced to a value similar to the basal level. This result is consistent with the structure of the peptide which contains the indole ring and $\beta$-carboxylic acid involved in receptor binding but does not possess any of the essential structural elements for induction of the biological response. Peptide XXII, however, is an agonist when administered at 80 pmol.Kg$^{-1}$ or 4 pmol.Kg$^{-1}$. The introduction of a $\gamma$-lactam ring (which may lead to a $\beta$-bend conformation) into the sequence, enhances the activity of the analogue since it induces an acid secretion rate similar to that produced by pentagastrin at a dose of 13 nmol.Kg$^{-1}$.

The second rat model, utilising an isolated, perfused stomach, was used to assess the activity of the analogues depicted in Table 6.3. Each analogue was tested in the absence and in the presence of gastrin-17 (520 pM), and the total acid output was expressed in $\mu$mol.H$^+$.60 min$^{-1}$. The results for each analogue are summarised in table 6.4. Peptides VII and VIII (AcO-Trp-Leu-Asp-Phe(t)NH$_2$ and AcO-Trp-Leu-Asp-Phe(t)NHCH$_3$) are weak agonists of acid secretion which is consistent with their structure. The presence of the C-terminal thioamide appears to be tolerated by the

TABLE 6.2

The effect of synthetic gastrin analogues on acid secretion from the ligated rat stomach.

| PEPTIDE | CONCENTRATION | ACID SECRETION ($\mu$mol/80 min) |
|---|---|---|
| BASAL | — | 26.7 ± 3.21 |
| PENTAGASTRIN | 13 nmol/kg | 60.6 ± 8.63 |
| PEPTIDE I | 8.2 nmol/kg | 28.6 ± 4.21 |
| PEPTIDE I + PENTAGASTRIN | 8.2 nmol/kg 13 nmol/kg | 22.7 ± 7.27 |
| PEPTIDE XXII | 80 pmol/kg | 55.7 ± 12.6 |
| PEPTIDE XXII | 4 pmol/kg | 50.0 ± 7.71 |

TABLE 6.3

Analogues tested using the isolated, perfused rat stomach.

| PEPTIDE | STRUCTURE |
|---|---|
| VII | AcO-Trp-Leu-Asp-Phe(t)NH$_2$ |
| VIII | AcO-Trp-Leu-Asp-Phe(t)NHCH$_3$ |
| IX | AcO-Trp-Leu-Asp(t)NH$_2$ |
| XI | Z-Leu(t)-Asp-Phe-NH$_2$ |
| XXI | Trp-Leu$\psi$(COCH$_2$NH)-Asp-Phe-NH$_2$ |

TABLE 6.4

Acid output ($\mu$mol H$^+$/60 min) from the isolated, perfused rat stomach in the presence of synthetic gastrin analogues.

| | PEPTIDE CONCENTRATION (M) | | | | |
|---|---|---|---|---|---|
| | 0 | 10$^{-9}$ | 10$^{-7}$ | 10$^{-5}$ | 10$^{-5}$ G-17 |
| BASAL | 8.7 | — | — | — | — |
| GASTRIN | 58.7 | — | — | — | — |
| PEPTIDE VII (520 pM) | — | 7.9 | 28.9 | 74.7 | 92.7 |
| VIII | — | 7.4 | 25.5 | 71.7 | 88.4 |
| IX | — | 15.5 | 6.0 | 15.0 | 60.6 |
| XI | — | 7.2 | 6.9 | 1.8 | 39.2 |
| XXI | — | 2.2 | 1.6 | 22.4 | 68.5 | receptor although the potency of the analogues is much reduced. Analogue IX (Aco-Trp-Leu-Asp(t)NH$_2$) has no effect on acid secretion from the isolated rat stomach. This result is to be compared with that obtained with the parent oxy analogue, Boc-Trp-Leu-$\beta$-Ala (Lavezzo et al., 1986). The lack of biological activity associated with the synthetic peptide may be explained by the presence of the large sulphur atom which could be disrupting essential hydrogen-bonding with the receptor or increasing the steric hinderance of the peptide. Analogue XI (Z-Leu(t)-Asp-Phe-NH$_2$) is a weak antagonist of acid secretion and yet it contains structural features which would be consistent with a weak gastrin agonist (Lin, 1972; Debas and Grossman, 1974). The alteration in the biological nature of the synthetic peptide may be explained by a resistance to proteolytic cleavage between Leu and Asp or an altered hydrogen-bonding pattern to the receptor caused by the introduction of the thioamide moiety. This result does not substantiate the claim by Martinez that the proteolytic cleavage of the Met-Asp bond is part of the induction of acid secretion by gastrin.

Peptide XXI (Trp-Leu$\psi$(COCH$_2$NH)-Asp-Phe-NH$_2$) exhibits conflicting biological effects. At low concentrations it inhibits basal acid secretion although when administered at 10$^{-5}$M or in conjunction with gastrin-17, it acts as a weak agonist. Martinez et al., (1985) demonstrated that analogues containing a methyleneamino (—CH$_2$NH—) pseudopeptide bond between Met and Asp are potent antagonists of pentagastrin-stimulated acid secretion. The fact that peptide XXI is a partial agonist appears to contradict the cleavable bond theory for the induction of acid secretion.

6.2.3 The Response of the Dog Stomach to Analogues Based on the C-terminal Region of Gastrin The analogues depicted in Table 6.5 were tested as gastrin antagonists using dogs surgically prepared with gastric fistulae and Heidenhain pouches. The acid secretion was measured at 10 minute intervals during the administration of pentagastrin and each of the analogues. The results of the time course for Boc-Trp-Leu-$\beta$-Ala are typical for all of the analogues studied. Each analogue was infused for 90 minutes at a rate of 20 pmol.kg$^{-1}$.h$^{-1}$ and in each case the synthetic peptide significantly suppressed acid secretion from the innervated gastric fistula and denervated Heidenhain pouch.

The total amount of acid suppression by each analogue over the period 110–170 minutes is summarised in Table 6.6. All the analogues are inhibitors of pentagastrin-stimulated secretion when administered at 20 pmol.kg$^{-1}$.h$^{-1}$, although the potency of the analogues, as assessed by total acid suppression, varies considerably. The effect of replacement of phenylalanine by phenethylamine has already been studied by Martinez et al., (1986b). However, the effect of the replacement of phenylalanine by m-aminobenzoic acid has not been reported. The double replacement of Boc-tryptophan by indole-3-propionic acid and phenylalanine by phenethylamine (peptide V) has, likewise, not been reported previously. From the results of this study, it appears that all of these replacements are tolerated in the antagonist structure and may serve to stabilize it against proteolytic attack. Lavezzo et al., (1986) found that the shortest sequence still retaining antagonist activity was Boc-Trp-leu-Asp-NH$_2$. However, it now appears that this structure may be condensed to Boc-Trp-Leu-β-Ala while still retaining potent antagonistic properties.

TABLE 6.5

Gastrin analogues tested as antagonists using dogs surgically prepared with gastric fistulae and Heidenhain pouches.

| PEPTIDE | SEQUENCE |
| --- | --- |
| I | Boc-Trp-Leu-B-Ala |
| III | IPA-Leu-B-Ala |
| II | PPA-Leu-B-Ala |
| V | IPA-Leu-Asp-PEA |
| VI | Boc-Trp-Leu-Asp-mABA-OMe |
| XIV | PPA-N-Me-Leu-B-Ala |
| XV | PPA-Leu-N-Me-B-Ala |

TABLE 6.6

Inhibition of acid by the synthetic analogues from the gastric fistula (GF) and Heidenhain pouch (HP) during the period of administration of the analogue. The percentage inhibition for each analogue is given in brackets

| | ACID INHIBITION (mmol H$^+$/kg) | |
| --- | --- | --- |
| PEPTIDE | GF | HP |
| I | 617.58 (60%) | 35.70 (55.8%) |
| II | 562.22 (54.7%) | 32.59 (50.92%) |
| III | 125.51 (12.2%) | — |
| V | 303.25 (29.5%) | 11.00 (17.2%) |
| VI | 446.19 (43.4%) | 42.20 (65.9%) |
| XIV | 256.77 (25%) | — |
| XV | 185.32 (18%) | — |

This structure can be reduced further by replacing Boc-tryptophan by indole-3-propionic acid (peptide III) or phenyl-3-propionic acid (peptide II). Both of these peptides are gastrin antagonists although they are less potent than the parent peptide (Boc-Trp-Leu-β-Ala). This may be explained by a reduction in the receptor affinity for the peptides due to the alteration of the tryptophan residue. N-Alkylation of peptide II to give PPA-N-Me-Leu-β-Ala (peptide XIV) and PPA-Leu-N-Me-β-Ala (peptide XV) still yields antagonists with significant activity. The most potent antagonist of the series is Boc-Trp-leu-β-Ala and the activity decreases in the order I>III>XIV>XV>II. The introduction of N-alkylated peptide bonds may stabilise the antagonist to proteolytic attack and this may account for the higher potency of analogues XIV and XV in comparison to the parent peptide (II).

When histamine is used as the stimulant for acid secretion the synthetic analogues appear to have no effect. Only one peptide was tested as an antagonist of histamine-stimulated acid secretion and the results are summarised in Table 6.7. There was no inhibition caused by the analogue in either the gastric fistula or Heidenhain pouch systems. Thus, the analogue (peptide VI) appears to be specific for pentagastrin as a stimulant.

The effect of the analogues on pepsin secretion by the Chief cells was also studied. The total inhibition of pepsin secretion by each analogue is summarised in Table 6.8. Only in the case of

TABLE 6.7

Inhibition of histamine stimulated acid secretion from the gastric fistula (GF) and Heidenhain pouch (HP) during the period of administration of the analogue. The percentage inhibition is given in brackets.

| | Acid Inhibition (mmol H$^+$/kg) | |
| --- | --- | --- |
| PEPTIDE | GF | HP |
| I | — | — |
| II | — | — |
| III | — | — |
| V | — | — |
| VI | −83.04 | 0.90 (0.004%) |
| XIV | — | — |
| XV | — | — |

TABLE 6.8

The inhibition of pepsin secretion from the gastric fistula (GF) and Heidenhain pouch (HP) during the period of administration of the analogues. The percentage inhibition for each analogue is shown in brackets.

| | Inhibition of Pepsin Secretion (Units/kg) | |
| --- | --- | --- |
| PEPTIDE | GF | HP |
| I | 67.3 (59.2%) | 1.65 (NS) |
| III | 71.1 (62.5%) | 5.78 (NS) |
| V | −3.1 (0%) | 2.04 (NS) |
| VI | −5.8 (0%) | −1.33 (NS) |

Boc-Trp-Leu-β-Ala (peptide I) and IPA-Leu-β-Ala (peptide III) is there a significant decrease in pepsin secretion from the gastric fistula. Thus, the presence of a gastrin receptor on the Chief cell cannot be concluded from this result.

6.2.4 Discussion

Of the analogues tested as inhibitors of gastric acid secretion, Boc-Trp-Leu-β-Ala (peptide I) and its related compounds (peptides II, III, XIV and XV) appear to be the most promising. The testing of the thionopeptides (peptides VII, VIII, IX and XI) was not as successful, partly due to the chosen animal model. The rat system appears to be only suitable for the initial assessment of the analogues while the in vivo dog model is the system of choice for the accurate determination of acid inhibition.

The results of this study would suggest that the minimum structural determinants necessary for antagonism may reside within the sequence Boc-Trp-Leu-β-Ala. Of this structure, only the indole ring and β- carboxylic acid are essential, which confirms that these residues are very important for receptor binding. The tryptophan residue and the peptide bonds can be altered while still retaining the antagonistic effect, although the potency of the analogues drops correspondingly. This suggests that there is a decrease in receptor recognition due to the removal of the heterocyclic ring (in the case of peptide II) or the gross alteration of the conformation of the peptide (in the case of peptides II, III, XIV and XV). The removal of the N-terminal amino group and C-terminal carboxyl group will undoubtedly stabilise the peptide to proteolytic attack and hence increase its potency in vivo. This effect can be seen in the case of analogues II, XIV and XV.

The effect of conformation on biological activity was probed by peptide XXII. The introduction of a synthetic constraint ($\gamma$-lactam) appears to increase the affinity of the peptide for the gastrin receptor by approximately 120 fold (as compared to pentagastrin). This increased affinity may be explained by the induction of a more rigid conformation within the peptide which could result in a reduced loss of entropy on binding to the receptor and hence a higher association constant. Freidinger (1981) suggested that the $\gamma$-lactam has a close structural homology with a type II' $\beta$-turn. However, the formation of a $\beta$-bend within peptide XXII has not been demonstrated.

BIBLIOGRAPHY

A

Abernethy, R. J., Gillespie, I. E., Lawrie, J. M., Forrest, A. P. M., Payne, R. A., Barabas, A., Johnston, I. D. A., Burns, G. P., Hobbs, K. E. F., Clegg, R. T., Duthie, H. L. & Fitzgerald, J. D. (1967) *Lancet* i, 291–295

Adachi, H., Rajh, H. M., Tesser, G. I., De Pont, G. J. J., Jensen, R. T. & Gardner, J. D. (1981) *Biochim. Biophys. Acta* 678, 358–363

Alexandrova, M., Strbak, V., Herman, Z. S., Stachura, Z. & Kruszynski, M. (1987) *Endocrinol. Exper.* 21, 43–49

Almquist, R. G., Chao, W.-R., Ellis, M. E. & Johnson, H. L. (1980) *J. Med. Chem.* 23, 1392–1398

Alp, M. H., Ewart, J. H. & Grant, A. K. (1970) *Gut* 11, 773–777

Anderson, G. W., Zimmerman, J. E. & Callahan, F. M. (1964a) *J. Amer. Chem. Soc.* 86, 1839–1844

Anderson, J. C., Barton, M. A., Gregory, R. A., Hardy, P. M., Kenner, G. W., MacLeod, J. K., Preston, J., Sheppard, R. C. & Morley, J. S. (1964b) *Nature* 204, 933–934

Andersson, S. & Elwin, C. E. (1971) *Acta Physiol. Scand.* 83, 437–445

Anson, M. L. (1938) *J. Gen. Physiol.* 22, 79–89

Anwer, M. K. & Spatola, A. F. (1980) *Synthesis*, 929–932

Aplin, R. T., Christiansen, J. & Young, G. T. (1983) *Int. J. Peptide Protein Res.* 21, 555–561

Aures, D. & Hakånson, R. (1968) *Eur. J. Pharmacol.* 3, 316–321

B

Bacarese-Hamilton, A., Adrian, T. & Bloom, S. R. (1984) *Regul. Peptides* 9, 289–298

Bardi, R., Piazzesi, A. M. & Toniolo, C. (1988) *Tetrahedron* 44, 761–769

Baron, J. H. (1972) *Chronic Duodenal Ulcer* (Wastell, C., Ed.), pp. 82–114, Appleton-Century-Crofts, London Bartlett, P. A., Spear, K. L. & Jacobsen, N. E. (1982) *Biochemistry* 21, 1608–1611

Bayliss, R. S., Knowles, J. R. & Wybrandt, G. B. (1969) *Biochem. J.* 113, 377–386

Beattie, R. E., Elmore, D. T., Williams, C. H. & Guthrie, D. J. S. (1987) *Biochem. J.* 245, 285–288

Beaumont, W. (1833) *Experiments and Observations on the Gastric Juice and the Physiology of Digestion* (Osler, W., Ed.), pp. 1–280, Dover Publications, New York Beddell, C. R., Clark, R. B., Hardy, G., Lowe, L. A., Ubatuba, F. B., Vane, J. R., Wilkinson, S., Chang, K. J., Cuatrecasas, P. & Miller, R. J. (1977) *Proc. R. Soc. London, Ser. B.* 198, 249–265

Bedi, B. S., Govaerts, J.-P., Master, S. P. & Gillespie, I. E. (1967) *Scand. J. Gastroenterol.* 2, 68–76

Behar, J. & Biancani, P. (1980) *J. Clin. Invest.* 66, 1231–1239

Beinfeld, M. C. (1985) *Peptides* 6, 857–860

Bender, M. & Brubacher, L. J. (1966) *J. Amer. Chem. Soc.* 88, 5880–5889

Bentley, P. H., Kenner, G. W. & Sheppard, R. C. (1966) *Nature* 209, 583–585

Berger, A., Smolarsky, M., Kurn, N. & Bosshard, H. R. (1973) *J. Org. Chem.* 38, 457–460

Berglindh, T., Helander, H. F. & Obrink, K. J. (1976) *Acta Physiol. Scand.* 87, 21A–22A Berglindh, T. & Sachs, G. (1979) *Digestion and Nutrition* (Rosselin, G., Fromageot, P. & Bonfils, S., Eds.) pp. 327–336, Elsevier, New York Bernfeld, P. (1955) *Methods in Enzymology*, vol. 1 (Colowick, S. P. & Kaplan, N. O., Eds.), pp. 149–158, Academic Press, New York Berson, S. A. & Yalow, R. S. (1971) *Gastroenterology* 60, 215–222

Betton, G. R., Harleman, J. H. & Salmon, G. K. (1986) *Toxicologist* 6, 4

Bock, M. G., DiPardo, R. M., Rittle, K. E., Evans, B. E., Freidinger, R. M., Verber, D. F., Chang, R. S. L., Chen, T., Keegan, M. E. & Lotti, V. J. (1986) *J. Med. Chem.* 29, 1941–1945

Bodanszky, M. & du Vigneaud, V. (1959) *J. Amer. Chem. Soc.* 81, 5688–5690

Bodanszky, M., Klausner, Y. S. & Ondetti, M. A. (1976) *Peptide Synthesis* (2nd ed.), pp. 18–69, John Wiley & Sons, New York Bodanszky, M., Natarajan, S., Hahne, W. & Gardner, J. D. (1977) *J. Med. Chem.* 20, 1047–1050

Bodanszky, M., Martinez, J., Priestley, G. P., Gardner, J. D. & Mutt, V. (1978) *J. Med. Chem.* 21, 1030–1035

Bodanszky, M., Martinez, J., Walker, M., Gardner, J. D. & Mutt, V. (1980) *J. Med. Chem.* 23, 82–85

Boel, E., Vuust, J., Norris, K., Wind, A., Rehfeld, J. F. & Marcker, K. A. (1983) *Proc. Natl. Acad. Sci. U.S.A.* 80, 2866–2869

Bond, M. D., Holmquist, B. & Vallee, B. L. (1986) *J. Inorg. Biochem.* 28, 97–105

Bozkurt, T., Adler, G., Koop, I., Koop, H., Türmer, W. & Arnold, R. (1988) *Dig. Dis. Sci.* 33, 276–281

Brennan, D. P. & Levine, M. A. (1987) *J. Biol. Chem.* 262, 14795–14800

Briet, C., Aumelas, A. & Martinez, J. (1985) *Int. J. Peptide Protein Res.* 26, 294–298

Brimblecombe, R. W., Duncan, W. A. M., Durant, G. J., Emmett, J. C., Ganellin, C. R. & Parsons, M. E. (1975) *J. Int. Med. Res.* 3, 86–92

Brogden, R. N., Carmine, A. A., Heel, R. C., Speight, T. M. & Avery, G. S. (1982) *Drugs* 24, 267–303

Brooks, F. P. (1967) *Handbook of Physiology* (Code, C. F., Ed.), pp. 805–826, American Physiological Society, New York Brown, J. & Gallagher, N. D. (1978) *Biochem. Biophys. Acta* 538, 42–49

Bruzzone, R., Halban, P. A., Gjinovci, A. & Trimble, E. R. (1985) *Biochem. J.* 226, 621–624

Buchan, A. M. J., Polak, J. M., Solcia, E., Capella, C., Hudson, D. & Pearse, A. G. E. (1978) *Gut* 19, 403–407

Buffa, R., Solcia, E. & Go, V. L. W. (1976) *Gastroenterology* 70, 528–532

Bugat, R. & Grossman, M. I. (1975) *Gastroenterology* 68, 1055

Bussolati, G., Capella, C., Solcia, E., Vassallo, G. & Vezzadini, P. (1971) *Histochemie* 26, 218–229

Bussolati, G. & Canese, M. G. (1972) *Histochemie* 29, 198–209

C

Calam, J., Ellis, A. & Dockray, G. (1982) *J. Clin. Invest.* 69, 218–225

Capella, C., Solcia, E. & Vassallo, G. (1969) *Arch. Histol. Jap.* 30, 479–494

Capella, C., Solcia, E. & Vassallo, G. (1971) *Endocrinology 1971* (Taylor, S., Ed.), pp. 282–290, Heinemann, London Capella, C. & Solcia, E. (1972) *Arch. Histol. Jap.* 35, 1–37

Chambers, R. W. & Carpenter, F. H. (1955) *J. Amer. Chem. Soc.* 77, 1527–1531

Chance, R. E., Ciezkowski, M., Jaworek, J., Konturek, S. J., Swierczek, J. & Tasler, J. (1981) *J. Physiol.* 314, 1–9

Chang, R. S. L., Lotti, V. J., Monaghan, R. L., Birnbaum, J., Stapley, E. O., Goetz, M. A., Albers-Schönberg, G., Patchett, A. A., Liesch, J. M., Hensens, O. D. & Springer J. P. (1985) *Science* 230, 177–179

Chargaff, E., Levine, C. & Green, C. (1948) *J. Biol. Chem.* 175, 67–71

Charpentier, B., Durieux, C., Menant, I. & Roques, B. P. (1987) *J. Med. Chem.* 30, 962–968

Chaturvedi, N., Goodman, M. & Bowers, C. (1981) *Int. J. Peptide Protein Res.* 17, 72–78

Chaturvedi, D. N., Knittel, J. J., Hruby, V. J., Castrucci, A. M. de L. & Hadley, M. E. (1984) *J. Med. Chem.* 27, 1406–1410

Cheung, S. T. & Benoitin, N. L. (1977) *Can. J. Chem.* 55, 906–910

Childs, G. V., Naor, Z., Hazum, E., Tibolt, R., Westlund, K. N. & Hancock, M. B. (1983) *J. Histochem. Cytochem.* 31, 1422–1425

Chou, P. Y. & Fasman, G. D. (1977) *J. Mol. Biol.* 115, 135–175

Clark, C. R., Daum, P. & Hughes, J. (1986) *J. Neurochem.* 46, 1094–1101

Clausen, K. & Spatola, A. F. (1984) *Biochem. Biophys. Res. Commun.* 120, 305–310

Clausen, K., Thorsen, M. & Lawesson, S.-O. (1984) *J. Chem. Soc., Perkin Trans.* 1, 785–798

Cohen, S. L., Knight, M., Tamminga, C. A. & Chase, T. N. (1983) *Peptides* 4, 67–70

Cowan, W. K. (1973) *Clin. Gastroenterol.* 2, 539–546

Cox, M. T., Gormley, J. J., Hayward, C. F. & Petter, N. N. (1980) *J. Chem. Soc. Chem. Commun.*, 800–802

Coy, D. H., Heinz-Erian, P., Jiang, N.-Y., Sasaki, Y., Taylor, J., Moreau, J.-P., Wolfrey, W. T., Gardner, J. D. & Jensen, R. T. (1988) *J. Biol. Chem.* 263, 5056–5060

Crean, G. P., Marshall, M. W. & Rumsey, R. D. E. (1969) *Gastroenterology* 57, 147–155

Creutzfeld, W., Arnold, R. & Creutzfeld, C. (1974) *Endocrinology of the Gut* (Chey, W. Y. & Brooks, S. P., Eds.), pp. 35–62, Thorofare, N.J.

Curtius, T. (1902) *Chem. Ber.* 35, 3226–3228

D

Dajani, E. Z., Driskill, D. R., Bianchi, R. G., Collins, P. W. & Pappo, R. (1976) *Amer. J. Dig. Dis.* 21, 1049–1057

Dale, H. H. & Laidlaw, P. P. (1910) *J. Physiol.* 41, 318–344

De Aizpurua, H. J., Toh, B. H. & Ungar, B. (1983a) *Clin. Exp. Immunol.* 52, 341–349

De Aizpurua, H. J., Ungar, B. & Toh, B. H. (1983b) *Clin. Exp. Immunol.* 54, 405–410

De Aizpurua, H. J., Ungar, B. & Toh, B. H. (1985a) *New Engl. J. Med.* 313, 479–483

De Aizpurua, H. J., Ungar, B. & Toh, B. H. (1985b) *Clin. Exp. Immunol.* 61, 315–322

De Boer, T. J. (1953) Ph.D. Thesis, Groningen

De Graef, J., Keuppens, F. & Willems, G. (1979) *Gastroenterol. Clin. Biol.* 3, 3–6

Debas, H. T. & Grossman, M. I. (1974) *Gastroenterology* 66, 836

Deconinick, J. F., Potvliege, P. R. & Gepts, W. (1971) *Diabetologia* 7, 266–282

Della Ferra, M. & Baile, C. (1979) *Science* 206, 471–473

Deschenes, R., Lorenz, L., Hann, R., Roos, B., Collier, K. & Dixen, J. (1984) *Proc. Natl. Acad. Sci., U.S.A.* 81, 726–730

Deschodt-Lanckman, M., Bui, N., Noyer, M. & Christophe, J. (1981) *Regul. Peptides* 2, 15–30

Deschodt-Lanckman, M., Bui, N., Koulischer, D., Paoutaud, P. & Strosberg, P. W. (1983) *Peptides* 4, 71–78

Deschodt-Lanckman, M., Pauwels, S., Najdovski, T., Dimaline, R. & Dockray, G. J. (1988) *Gastroenterology* 94, 712–721

Dial, E., Thompson, W. J. & Rosenfeld, G. C. (1981) *J. Pharm. Exp. Ther.* 219, 585–590

Dietl, M. M., Probst, A. & Palacios, J. M. (1987) *Synapse* 1, 169–183

Dockray, G. J. & Walsh, J. H. (1975) *Gastroenterology* 68, 222–230

Dockray, G. J., Walsh, J. H. & Passaro, E. (1975) *Gut* 16, 353–358

Dockray, G. J. (1977) *Nature* 270, 357–361

Dockray, G. J. & Taylor, I. L. (1977) *Gastroenterology* 72, 814

Dockray, G. J., Gregory, R. A. & Hutchison, J. (1978) *Nature* 274, 711–713

Doyle, J., Wolfe, M. & McGuigan, J. (1984) *Gastroenterology* 87, 60–68

Du Vigneaud, V., Ressler, C., Swan, J. M., Roberts, C. W., Katsoyannis, P. G. & Gordon, S. (1953) *J. Amer. Chem. Soc.* 75, 4879–4880

Du Vigneaud, V., Winestock, G., Murti, V. V. S., Hope, D. B. & Kimbraugh, R. D. (1960) *J. Biol. Chem.* 235, 64–69

Dubreuil, P., Rodriguez, M., Magous, R., Lignon, M. F., Bali, J. P. & Martinez, J. (1987) *Gastroenterol. Clin. Biol.* 11, 740–741

Durieux, C., Belleney, J., Lallemand, J.-Y., Roques, B. P. & Fournie-Zaluski, M.-C. (1983) *Biochem. Biophys. Res. Commun.* 114, 705–712

Dutta, A. S. & Morley, J. S. (1976) *Peptides*, 517–522

Dutta, A. S., Gormley, J. J., Hayward, C. F., Morley, J. S., Shaw, J. S., Stacey, G. J. & Turnbull, M. T. (1977) *Brit. J. Pharmacol.* 61, 481–482

Dutta, A. S., Furr, B. J. A., Giles, M. B. & Valcaccia, B. (1978) *J. Med. Chem.* 21, 1018–1024

Dutta, A. S., Giles, M. B., Gormley, J. J., Williams, J. C. & Kusner, E. J. (1987) *J. Chem. Soc., Perkin Trans.* 1, 111–120

Duus, F. (1979) *Comprehensive Organic Chemistry* (Barton, D. H. R., Ed.), pp. 440–458, Pergamon Press, London

E

Eberlein, G. A., Eysselein, V., Hesse, W. H., Goebell, H., Schaefer, M. & Reeve, J. R. (1987) *Amer. J. Physiol.* 253, G477–482

Edkins, J. S. (1905) *Proc. Roy. Soc. London* 76, 376

Ehinger, B., Håkanson, R., Owman, C. & Sporrong, B. (1968) *Biochem. Pharmacol.* 17, 1997–1998

Ekman, L., Hansson, E., Havu, N., Carlsson, E. & Lungberg, D. (1985) *Scand. J. Gastroenterol.* 20, (suppl. 108), 53–69

Elder, J. R. (1985) *Gut* 26, 1279–1283

Elliot, D. F. & Russell, D. W. (1957) *Biochem. J.* 66, 49p

Eng, J., Shiina, Y., Pan, Y.-C., Blacher, R., Chang, M., Stein, S. & Yalow, R. S. (1983) *Proc. Natl. Acad. Sci., U.S.A.* 80, 6381–6385

Eng, J., Du, B.-H., Pan, Y.-C., Chang, M., Hulmes, J. & Yalow, R. S. (1984) *Peptides* 5, 1203–1206

Evans, B. E., Bock, M. G., Rittle, K. E., DiPardo, R. M., Whitter, W. L., Veber, D. F., Anderson, P. S. & Freidinger, R. M. (1986) *Proc. Natl. Acad. Sci., U.S.A.* 83, 4918–4922

Evans, J. C., Reeder, D. D., Becker, H. D. & Thompson, J. C. (1974) *Gut* 15, 112–115

Eysselein, V., Reeve, J., Shively, J., Hawke, D. & Walsh, J. (1982) *Peptides* 3, 687–691

Eysselein, V., Reeve, J., Shively, J., Miller, C. & Walsh, J. (1984a) *Proc. Natl. Acad. Sci., U.S.A.* 81, 6565–6568

Eysselein, V., Bottcher, W., Kauffman, G. & Walsh, J. (1984b) *Regul. Peptides* 9, 173–185

Eysselein, V., Eberlein, G. A., Hesse, W. H., Singer, M. V., Goebell, H. & Reeve, J. R. (1987) *J. Biol. Chem.* 262, 214–217

F

Farmer, P. S. (1980) *Drug Design, vol. 10* (Ariens, E. J., Ed.), pp. 121–141, Academic Press, New York Fellenius, E., Elander, B., Wallmark, B., Haglund, U., Helander, H. F. & Olbe, L. (1983) *Clin. Sci.* 64, 423–431

Finn, F. M., Titus, G. & Hofmann, K. (1984) *Biochemistry* 23, 2554–2558

Fletcher, G. A. & Jones, J. H. (1972) *Int. J. Peptide Protein Res.* 4, 347–371

Fok, K. F. & Yankeelov, J. A. (1977) *Biochem. Biophys. Res. Commun.* 74, 273–278

Folsch, U., Winckler, K. & Wormsley, K. (1978) *Scand. J. Gastroenterol.* 13, 663–671

Forssman, W. G. & Orci, L. (1969) *Cell Tissue Res.* 101, 419–432

Forte, T. M., Machen, T. E. & Forte, J. G. (1977) *Gastroenterology* 73, 941–955

Fourmy, D., Zahidi, A., Fabre, R., Guidet, M., Pradayrol, L. & Ribet, A. (1987) *Eur. J. Biochem.* 165, 683–692

Fournie-Zaluski, M. C., Durieux, D., Lux, B., Belleney, J., Pham, P., Gerard, D. & Roques, B. P. (1985) *Biopolymers* 24, 1663–1681

Fournie-Zaluski, M. C., Belleney, J., Lux, B., Durieux, C., Gerard, D., Gacel, G., Maigret, B. & Roques, B. P. (1986) *Biochemistry* 25, 3778–3787

Freidinger, R. M. (1981) *Peptides, Synthesis-Structure-Function* (Rich, D. H. & Gross, E., Eds.), pp. 673–683, Pierce Chemical Co., Illinois Freidinger, R. M., Perlow, D. S. & Veber, D. F. (1982) *J. Org. Chem.* 47, 104–109

Fujino, M. & Hatanaka, C. (1967) *Chem. Pharm. Bull.* 15, 2015–2018

G

Galas, M.-C., Lignon, M.-F., Rodriguez, M., Mendre, C., Fulcrand, P., Laur, J. & Martinez, J. (1988) *Amer. J. Physiol.* 254, G176–182

Gardner, J. D., Peskin, G. W., Cerda, J. J. & Brooks, F. P. (1967) *Amer. J. Surg.* 113, 57–64

Gardner, J. D., Walker, M. D., Martinez, J., Priestly, G. P., Natarajan, S. & Bodanszky, M. (1980) *Biochim. Biophys. Acta* 630, 323–329

Gesellchen, P. D., Frederickson, R. C. A., Tafur, S. & Smiley, D. (1981) *Peptides, Synthesis-Structure-Function* (Rich, D. H. & Gross, E., Eds.), pp. 621–624, Pierce Chemical Co., Illinois Gibbs, J. & Smith, G. (1977) *Amer. J. Clin. Nutr.* 30, 758–761

Gillessen, D., Trzeciak, A., Müller, R. K. M. & Studer, R. O. (1979) *Int. J. Peptide Protein Res.* 13, 130–136

Glass, G. B. (1980) *Gastrointestinal Hormones*, pp. 131–133, Raven Press, New York Go, V., Hofmann, A. & Summerskill, W. (1970) *J. Clin. Invest.* 49, 1558–1564

Göhring, W., Moroder, L., Borin, G., Lobbia, A., Bali, J.-P. & Wunsch, E. (1984) *Hoppe-Seyler's Z. Physiol. Chem.* 365, 83–94

Goldstein, A., Goldstein, J. S. & Cox, B. M. (1975) *Life Sci.* 17, 1643–1654

Gordon, A. J. & Ford, R. A. (1972) *A Chemist's Companion*, p. 107, Wiley-Interscience, New York Gordon, E. M., Natarajan, S., Pluscec, J., Weller, H. H., Godfrey, J. D., Rom, M. B., Sabo, E. F., Engebrecht, J. & Cushman, D. W. (1984) *Biochem. Biophys. Res. Commun.* 124, 148–155

Gregory, R. A., Tracy, H. J., French, J. M. & Sircus, W. (1960) *Lancet* i, 1045–1048

Gregory, R. A. & Tracy, H. J. (1961) *J. Physiol.* 156, 523–543

Gregory, R. A. & Tracy, H. J. (1964) *Gut* 5, 103–117

Gregory, R. A., Hardy, P. M., Jones, D. S., Kenner, G. W. & Sheppard, R. C. (1964) *Nature* 204, 931–934

Gregory, R. A. & Tracy, H. J. (1972) *Lancet* ii, 797–799

Gregory, R. A. (1974) *J. Physiol.* 241, 1–32

Gregory, R. A. & Tracy, H. J. (1974) *Gut* 15, 683–685

Greider, M. H. & McGuigan, J. E. (1971) *Diabetes* 20, 389–396

Grim, M. D., Chanhan, V., Shimohigashi, Y., Kolar, A. J. & Stammer, C. H. (1981) *J. Org. Chem.* 46, 2671-2673

Grossman, M. I., Robertson, C. R. & Ivy, A. C. (1948) *Amer. J. Physiol.* 153, 1-9

Grossman, M. I. (1970) *Gastroenterology* 58, 128

Grossman, M. I. (1978) *Gastrointestinal Disease* (Sleisenger, M. H. & Fordtran, J. S., Eds.), pp. 640-659, Saunders, Philadelphia Grossman, M. I. (1979) *Annu. Rev. Physiol.* 41, 27-33

Gubler, U., Chua, A., Hoffman, B., Collier, K. & Eng, J. (1984) *Proc. Natl. Acad. Sci., U.S.A.* 81, 4307-4310

Guthrie, D. J. S., Williams, C. H. & Elmore, D. T. (1986) *Int. J. Peptide Protein Res.* 28, 208-211

H

Håkanson, R., Lilja, B. & Owman, C. H. (1969) *Histochemie* 18, 74-86

Hall, M. M., Khosla, M. C., Khairallah, P. A. & Bumpus, F. M. (1974) *J. Pharmacol. Exp. Ther.* 188, 222-228

Harper, A. A. & Raper, H. S. (1943) *J. Physiol.* 102, 115-125

Harper, A. A. & Vass, C. C. N. (1941) *J. Physiol.* 99, 414-435

Harvey, R. F. & Read, A. E. (1973) *Lancet* i, 1-3

Hazum, E. (1986) *Methods in Enzymology* 124, 47-57

Helander, H. F. (1962) *J. Ultrastruct. Res. Suppl.* 4, 1-123

Henry, L. (1969) *Ann. Chem. Pharm.* 152, 148-149

Hochhaus, G., Gibson, B. W. & Sadée, W. (1988) *J. Biol. Chem.* 263, 92-97

Hoffman, K., Bohn, H. & Andretta, R. (1967) *J. Amer. Chem. Soc.* 89, 7126-7127

Hökfelt, T., Skirboll, L. & Rehfeld, J. F. (1980) *Neuroscience* 5, 2093-2124

Hotz, J. & Goebell, H. (1979) *Klin. Wochenschr.* 57, 1265-1271

Hsiao, S. & Wang, C. H. (1983) *Peptides* 4, 15-17

Hudson, D., Kenner, G. W., Sharp, R. & Szelke, M. (1979) *Int. J. Peptide Protein Res.* 14, 177-185

I

Irvine, W. T. & Code, C. F. (1958) *Amer. J. Physiol.* 195, 202-208

Ito, S. (1981) *Physiology of the Gastrointestinal Tract* (Johnson, L. R., Ed.), pp. 517-550, Raven Press, New York Ivarsson, L. E., Darle, N., Hulten, L., Lindhagen, J. & Lundgren, O. (1982) *Scand. J. Gastroenterol.* 17, 1037-1048

Ivey, K. J. (1975) *Gastroenterology* 68, 154-166

Ivy, A. C. & Oldberg, E. (1928) *Am. J. Physiol.* 86, 599-613

Iwai, K., Fukuoka, S.-I., Fushiki, T., Tsujikawa, M., Hirose, M., Tsunasawa, S. & Sakiyama, F. (1987) *J. Biol. Chem.* 262, 8956-8959

J

Jansen, J. & Lamers, C. (1983) *Life Sci.* 33, 2197-2205

Jensen, R. T., Moody, T., Pert, C., Rivier, J. E. & Gardner, J. D. (1978) *Proc. Natl. Acad. Sci., U.S.A.* 75, 6139-6143

Jensen, R. T., Lemp, G. F. & Gardner, J. D. (1982) *J. Biol. Chem.* 257, 5554-5559

Jensen, R. T., Collen, M. J., Pandol, S. J., Allende, H. D., Raufman, J. P., Bissonnette, B. M., Duncan, W. C., Durgin, P. L., Gillin, J. C. & Gardner, J. D. (1983a) *N. Engl. J. Med.* 308, 883-887

Jensen, R. T., Jones, S. W. & Gardner, J. D. (1983b) *Biochim. Biophys. Acta* 757, 250-258

Jensen, R. T., Murphy, R. B., Trampota, M., Schneider, L. H., Jones, S. W., Howard, J. M. & Gardner, J. D. (1985) *Amer. J. Physiol.* 249, G214-220

Joehl, R. J., Kelly, G. A. & Nahrwold, D. L. (1980) *Surg. Forum.* 31, 198-200

Johnson, L. R. (1973) *Amer. J. Physiol.* 225, 1411-1415

Johnson, L. R. (1976) *Gastroenterology* 70, 278-288

Johnson, L. R. (1977) *Gastroenterology* 72, 788-792

Johnson, L. R., Copeland, E. M. & Dubrick, S. J. (1978) *Scand. J. Gastroenterol.* 13 (Suppl. 49), 95

Johnson, L. R. & Guthrie, P. (1984) *Amer. J. Physiol.* 246, G62-66

Jones, R. S. & Grossman, M. I. (1970) *Amer. J. Physiol.* 219, 1014-1018

Jorpes, E. & Mutt, V. (1966) *Acta Physiol. Scand.* 66, 196-202

K

Kahlson, G., Rosengren, E., Svahn, D. & Thunberg, R. (1964) *J. Physiol.* 174, 400-416

Kaiser, E., Colescott, R. L., Bossinger, C. D. & Cook, P. I. (1970) *Anal. Biochem.* 34, 595-598

Katsoyannis, P. G., Tometsko, A. & Fukuda, F. (1963) *J. Amer. Chem. Soc.* 85, 2863-2865

Keeton, R. W. & Koch, F. C. (1915) *Amer. J. Physiol.* 37, 481-504

Kenner, G. W. & Sheppard, R. C. (1973) *Frontiers in Gastrointestinal Hormone Research* (Andersson, S., Ed.), pp. 137-142, Alquist and Wiksell, Stockholm Kettner, C. & Shaw, E. (1978) *Biochemistry* 22, 4778-4784

Khorana, H. G. (1953) *Chem. Rev.* 53, 145-166

Khosla, M. C., Stachowiak, K., Smeby, R. R., Bumpus, F. M., Piriou, F., Lintner, K. & Fermandjian (1981) *Proc. Natl. Acad. Sci., U.S.A.* 78, 757-760

Kier, L. B. & George, J. M. (1972) *J. Med. Chem.* 15, 384-386

Kisfaludy, L., Schön, I., Náfrádi, J., Varga, L. & Varró, V. (1978) *Hoppe-Seyler's 2. Physiol. Chem.* 359, 887-895

Knuhtsen, S., Holst, J. J., Jensen, S. L., Knigge, U. & Nielsen, O. V. (1985) *Amer. J. Physiol.* 248, G281-286

Komarov, S. A. (1938) *Proc. Soc. Exp. Biol. Med.* 58, 514-516

Korman, M. G., Scott, D. H., Hansky, J. & Wilson, H. (1972) *Aust. Nz. J. Med.* 3, 266-271

Kothary, P. C., Mahoney, W. C. & Vinik, A. I. (1987) *Regul. Peptides* 17, 71-84

L

La Cour, T. F. M., Hanson, H. A. S., Clausen, K. & Lawesson, S.-O. (1983) *Int. J. Peptide Protein Res.* 22, 509-512

Lajoie, G., Lépine, F., Lemaire, S., Jolicoeur, F., Aube, C., Turcotte, A. & Belleau, B. (1984) *Int. J. Peptide Protein Res.* 24, 316-327

Larose, L., Poirier, G. G., Dumont, Y., Fregeau, C., Blanchard, L. & Morisset, J. (1983) *Eur. J. Pharmacol.* 95, 215-223

Larsson, L. I. & Rehfeld, J. F. (1979) *Nature* 277, 575-578

Laur, J., Rodriguez, M., Aumélas, A., Bali, J.-P. & Martinez, J. (1986) *Int. J. Peptide Protein Res.* 27, 386-393

Lavezzo, A., Bali, J.-P., Magous, R., Lignon, M. F., Nisato, D., Laur, J., Castro, B. & Martinez, J. (1986) *Regul. Peptides* 15, 111-119

Lawesson, S.-O., Perregaard, J., Scheibye, S., Meyer, H. J. & Thomsen, I. (1977) *Bull. Soc. Chim. Belg.* 86, 679-687

Leopardi, C. P., Fabre, O., Zimmerman, D., Reisse, J., Cornea, F. & Fulea, C. (1977) *Can. J. Chem.* 55, 2649-2655

Levant, J., Kun, T., Jachna, J., Sturdevant, R. & Isenberg, J. (1974) *Dig. Dis.* 19, 207-209

Liakopoulou-Kyriakides, M. & Galardy, R. E. (1979) *Biochemistry* 18, 1952-1957

Liddle, R., Goldfine, I. & Williams, J. (1984) *Gastroenterology* 87, 542-549

Liddle, R., Goldfine, I., Rosen, M., Taplitz, R. & Williams, J. (1985) *J. Clin. Invest.* 75, 1144-1152

Lignon, M. -F., Galas, M. -C., Rodriguez, M., Laur, J., Auméelas, A. & Martinez, J. (1987) *J. biol. Chem.* 262, 7226-7231

Lin, T. -M. (1972) *Gastroenterology* 63, 922-923

Lloyd, K & Young, G. T. (1971) *J. Chem. Soc.*, cp 2890

Lonovics, J., Penke, G., Rayford, P. L. & Thompson, J. C. (1986) *Hepatogastroenterol.* 33, 27-33

Loomis, R. E., Lee, P. -C. & Tseng, C. -C. (1987) *Biochim. Biophys. Acta* 911, 168-179

Luckhardt, A. B., Keeton, R. W., Koch, F. C. & La Mer, V. 91920) *Amer. J. Physiol.* 50, 527-543

Lund, T., Geurts van Kessel, A. H. M., Haun, S & Dixon, J. E. (1986) *Hum. Genet.* 73, 77-80

Lundell, L. (1974) *J. Physiol.* 241, 437-451

Lundell, L., Forsell, H., Lönroth, H., Rosengren, E. & Wingren, U. (1986) *Acta Physiol. Scand.* 128, 587-595

M

Madsen, O. D., Larsson, L. I. & Rehfeld, J. F. (1986) *J. Cell. Biol.* 103, 2025-2034

Magee, D. F. (1986) *Digestion and the Structure and Function of the Gut*, p 310, Karger Press, New York Magee, D. F. & Nakajima, S. (1968) *J. Physiol.* 196, 713-721

Magous, R & Bali, J. -P. (1982) *Eur. J. Pharmacol.* 82, 47-54

Magous, R., Bali, J. -P., Moroder, L. & Previero, A. (1982) *Eur. J. Pharmacoil.* 77, 11-16

Majer, Z., Zewdu, M & Hollösi, M. (1988) *Biochem. Biophys. Res. Commun.* 150, 1017-1020

Major, J. S. & Scholes, P. (1978) *Agents Actions* 8, 324-331

Majumdar, A. P. N. & Johnson, L. R. (1982) *Amer. J. Physiol.* 242, G135-139

Makovec, F., Chisté, R., Bani, M., Revel, L., Setniker, I. 7 Rovati, a. L. (1986) *Eur. J. Med. Chem.-Chim. Ther.* 21, 9-20

Mammi, S., Goodman, M., Peggion, E., Foffani, M. T., Moroder, L. & Wüsch, E. (1986) *Int. J. Peptide Protein Res.* 27, 145-152

Mammi, S., Mammi, N. J., Foffani, M. T. Peggion, E., Moroder, L. & Wünsch, E. (1987) *Biopolymers* 26, S1-10

Martin, G. T., Dorine, J. P., Robiller, C. R. & Martin, M. L. (1977) *J. Amer. Chem. Soc.* 99, 1381-1384

Martinez, J., Winternitz, F., Bodanszky, M., Gardner, J. D., Walker, M. D. & Mutt, V. (1982) *J. Med. Chem.* 25, 589-593

Martinez, J. & Bali, J. -P. (1984) *Regul. Peptides* 9, 259-262

Martinez, J., Magous, R., Lignon, M. F., Laur, J., Castro, B. & Bali, J. -P. (1984) *J. Med. Chem.* 27, 1597-1601

Martinez, J., Bali, J. -P., Rodriguez, M., Castro, B., Magous, R., Laur, J. & Lignon, M. F. (1985) *J. Med. Chem.* 28, 1874-1879

Martinez, J., Rodriguez, M., Bali, J. -P. & Laur, J. (1986a) *J. Med. Chem.* 29, 2201-2206

Martinez, J., Rodriguez, M., Bali, J. -P. & Laur, J. (1986b) *Int. J. Peptide Protein Res.* 28, 529-535

Maton, P., Selden, A., Fitzpatrick, M. & Chadwick, V. (1985) *Gastroenterology* 88, 391-396

Matsumoto, M., Park, J. & Yamada, T. (1987) *Amer. J. Physiol.* 252, G143-147

Maziak, L., Lajoie, G. & Belleau, B. (1986) *J. Amer. Chem. Soc.* 108, 182-183

McGuigan, J. E. (1968) *Gastroenterology* 33, 315-319

McGuigan, J. E. & Trudeau, W. L. (1970) *N. Engl. J. Med.* 282, 358-368

McGuigan, J. E., Isaza, J. & Landor, J. (1971) *Gastroenterology* 61, 659-666

McGuigan, J. E. (1976) 1st International Symposium on Gastrointestinal Hormones, A096, Asilomar, California McGuigan, J. E., Harty, R. F. & Marco, D. G. (1980) *Am. Clin. Climatol. Assoc.* 92, 199-207

McGuigan, J. E. (1981) *Gastroenterology* 80, 181-182

Merrifield, R. B. (1962) *Federation Proc.* 21, 412

Merrifield, R. B. (1963) *Amer. Chem. Soc.* 85, 2149-2154

Merritt, J. E., Taylor, C. W., Rubin, R. P. & Putney, J. W. 91986) *Biochem. J.* 236, 337-343

Meyer, J. & Jones, R. (1974) *Amer. J. Physiol.* 226, 1178-1187

Meyer, J., Kelly, G., Spingola, L. & Jones, R. (1976) *Amer. J. Physiol.* 231, 669-677

Mitchell, A. R., Kent, S. B. H., Chu, I. C. & Merrifield, R. B. (1978) *Anal. Chem.* 50, 637-640

Mock, W. L., Chen, J. -T. & Tsang, J. W. (1981) *Biochem. Biophys. Res. Commun.* 102, 389-396

Moore, S., Felix, A. M., Meienhofer, J., Smith, C. W. 7 Walter, R. (1977) *J. Med. Chem.* 20, 495-500

Moran, T. H., Robinson, P. H., Goldrich, M. S. & McHugh, P. R. (1986) *Brain Res.* 362, 175-179

Morgan, K., Schmalz, P., Go, V. & Szurszewski, J. (1978) *Gastroenterology* 75, 405-412

Morley, J. S., Tracy, H. J. & Gregory, R. A. (1965) *Nature* 207, 1356-1359

Morley, J. S. (1967) *Peptides, Proceedings of the Eighth European Peptide Symposium* (Beyerman, H. C., Van De Linde, A. & Maasen van der Brink, W., Eds.), pp. 226-234

Morley, J. s. (1968) *Proc. Roy. Soc. London. Ser. B.* 170, 97-111

Moroder, L., Hallett, A., Wünsch, E.. Keller, O. & Wersin, G. (1976) *Hoppe-Seyler's . Physiol. Chem.* 357, 1651-1653

Moroder, L., Göhring, W., Nyfeler, R., Scharf, R., Thamm, P. & Wendelberger, G. (1983) *Hoppe-Seyler's Z. Physiol. Chem.* 364, 157-171

Mortensen, N. J. McC. & Morris, J. F. (1977) *Cell Tissue Res.* 176, 251-263

Muallem, S., Schoefield, M., Pandol., S. & Sachs, G. (1985) *Proc. Natl. Acad. Sci., U.S.A.* 82, 4433-4437

Mutt, V. & Jorpes, E. (1968) *Eur. J. Biochem.* 6, 156-162

Mutt, V. & Jorpes, E. (1971) *Biochem. J.* 125, 57-58

N

Nagain, C., Rodriguez, M., Martinez, J. & Rozé, C. (1987) *Peptides* 8, 1023-1028

Nagasawa, T., Kuriowa, K., Narita, K. & Isowa, Y. (1973) *Bull Chem. Soc. Japan* 46, 1269-1272

Nair, N. P. V., Lal, S. & Bloom, D. M. (1985) *Prog. Neuropsychopharmacol. Biol. Psychiat.* 9, 515-524

Najdovski, T., Collette, N. & Deschodt-Lanckman, M. (1985) *Life Sci.* 37, 827-834

Nakamura, M., Oda, M., Kaneko, K., Yonei, Y., Tsukada, N., Komatsu, H., Tsugu, M. & Tsuchiya, M. (1987) *Peptides* 8, 391-398

Nakayama, H., Shikano, H., Aoyama, T., Amano, T. & Kanaoka, Y. (1986) *FEBS Lett.* 208, 278-282

Natarajan, s., Gordon, E. M., Sabo, E. F., Godfrey, J. D., Weller, H. N., Pluscec, J., Rom, M. B. & Cushman, D. W. (1984) *Biochem. Biophys. Res. Commun.* 124, 141-147

Navech, J., Majoral, J. P. & Kraemer, R. (1983) *Tetrahedron Lett.* 24, 5885-5886

Neubert, K., Baláspiri, L. 7 Loss, G. (1972) *Monatsh. Chem.* 103, 1575-1581 Niederau, C., Niedereau, M. Williams, J. A. & Grendell, J. H. (1986) *Amer. J. Physiol.* 251, G856-860

Niendorf, A., Dietel, M., Arps, H., Lloyd, J. & Childs, G. V. 91986) *J. Histochem. Cytochem.* 34, 357-361

Nilsson, G., Simon, J., Yalow, R. S. & Berson, S. A. (1972) *Gastroenterology* 63, 51-59

Nilsson, G., Yalow, R. S. & Berson, S. A. (1973) *Frontiers in Gastrointestinal Hormone Research* (Anderson, S., Ed.), pp. 95-101, Almquist and Wiksell, Stockholm

O

Okada, S. (1914) J. Phyiol. 49, 457-482

Okuma, Y., Psumi, Y., Ishikawa, T. & Nagata, M. (1983) *Life Sci.* 32, 1363-1370 Olbe, L. (1964) *Acta Physiol. Scand.* 62, 169-175

Olbe, L., Berglindh, T., Elander, B., Helander, B., Helander, H., Fellenius, E., Sjastraud, S. E., Sundall, G. & Wallmark, b. (1979) *Scand. J. Gastroenterol.* 55 (Suppl.), 131-132

Ondetti, M. A., Pluscec, J., Sabo, E. F., Sheehan, J. T. & Williams, N. (1970) *J. Amer. Chem. Soc.* 92, 195-199

Ondetti, M. A., Pluscec, J., Weaver, E. R., Williams, N., Sabo, E. F. & Kocy, O. (1972) *Chemistry and Biology of Peptides* (Meienhofer, J., Ed.), pp. 525-531, Ann Arbor Science, Michigan Ong, E. B., Shaw, E. & Schoellmann, G. (1965) *J. Biol. Chem.* 240, 694-698

Orci, L., Pictet, R., Forssmann, W. G., Renold, A. E. & Rouiller, C. (1968) *Diabetologia* 4, 56-57

Owyang, C., Louie, D. S. & Tatum, D. (1986) *J. Clin. Invest.* 77, 2042-2047

P

Pachter, I. J. & Kloetzel, M. c. (1952) *J. Amer. Chem. Soc.* 74, 1321-1322

Pan, G. -Z., Martinez, J., Bodanszky, M., Jensenm, R. T. & Gardner, J. D. (1981) *Biochem. Biophys. Acta* 678, 352-357

Pappas, T. N., Debas, H. T. & Taylor, I. L. (1985) *Gastroenterology* 89, 1387-1392

Pauwels, S. & Dockray, G. J. (1982) *Gastroenterology* 82, 56-61

Pauwels, S., Dockray, G. J., Walker, R & Marcus, S. (1984) *Gastroenterology* 86, 86-92

Pauwels, S., Dockray, G. J., Walker, R & Marcus, S. (1985) *J. Clin. Invest.* 75, 2006-2013

Pauwels, S., Dockray, G. J. 7 Walker, R. (1987) *Gastroenterology* 92, 1220-1225 Pavlov, I. (1910) *The Work of the Digestive Glands,* Griffin Press, London Peggion, E., Foffani, M. T., Wünsch, E. Moroder, L. Borin, G., Goodman, M. & Mammi, S. (1985) *Biopolymers* 24, 647-666

Penke, B., Hajnal, F., Lonovics, J. Holzinger, G., Kadar, T., Telegdy, G. & Rivier, J. (1984) *J. Med. Chem.* 27, 845-849

Perregaard, J. Thomsen, I. & Lawesson, S. -O. (1977) *Bull. Soc. Chim. Belg.* 86, 321-328

Petersen, O. H. (1984) Bioscience Reports 4, 275-283

Pinner, A & Klein, F. (1878) *Chem. Ber.* 11, 1825

Piszkiewicz, D. (1974) *Nature* 248, 341-342

Pointer, J. P., Accary, J., Vatier, M., Dubrasquest, M. & Bonfils, S. (1973) *Horm. Metab. Res.* 5, 303-304

Polak, J. M., Stagge, B. & Pearse, A. G. E. (1972) *Gut* 13, 501-512

Polak, J. M., Bloom, S. R., Rayford, P. L., Pearse, A. G. E., Buchan, A. M. J. & Thompson, J. C. (1975a) *Lancet* ii, 1016-1018

Polak, J. M., Pearse, A. G. E., Grimleius, L., Bloom, S. R. & Arimura, A. (1975b) *Lancet* i, 1220-1222

Popielski, L. (1920) *Pflug. Arch. Physiol.* 178, 214-236

Power, D. M., Bunnett, N., Turner, A. J. & Dimaline, R. (1987) *Amer. J. Physiol.* 253, G33-39

Powers, J. C. & Tuhy, P. M. (1973) *Biochemistry* 12, 4767-4773

Praissman M., Fara, J. W., Praissman, L. A. & Berkowitz, J. M. (1982) *Biochim. Biophys. Acta* 716, 240-248

Praissman, M., Martinez, P. A., Saladino, C. F., Berkowitz, J. M. Steggles, A. W. & Finkelstein, J. A. (1983) *J. Neurochem.* 40, 1406-1413

R

Rajh, H. M. Mariman, E. C. M., Tesser, G. I. & Nivard, R. J. F. (1980) *Int. J. Peptide Protein Res.* 15, 200-210

Rakovska, A., Henklein, P., Milenov, K., Nieber, K. & Oehme, P. (1987) *Meth. Find. Exptl. Clin. Pharmacol.* 9, 429-435

Rauber, P., Angliker, H., Walker, B. & Shaw, E. (1986) *Biochem. J.* 239, 633-640

Rauchfuss, T. B. & Zank, G. A. (1968) *Tetrahedron Lett.* 27, 3445-3448

Ravdel, G. A., Filatova, M. P. Shchukina, L. A., Paskhina, T. S., Survoikina, M. S., Trapeznikova, S. S. & Egorova, T. P. (1967) *J. Med. Chem.* 10, 242-246

Razniak, S. L., Flagg, E. M. & Siebenthall, F. M. J. (1973) *J. Org. Chem.* 38,

Redeuilh, G., Secco, C. 7 Baulieu, E. -E. (1985) *J. Biol. Chem.* 260, 3996-4002

Reeder, D. D., Villar, H. V., Brandt, E. N., Rayford, P. L. & Thompson, J. C. (1974) *The Physiologist* 17, 319

Reeve, J., Eysselein, V., Walsh, J. Sankaran, J., Deveney, C., Tourtellotte, W., Miller, C. & Shively, J. (1984) *Peptides* 5, 959–966

Reggio, H., Cailla-Deckmyn, H. & Marchis-Mouren, G. (1971) *J. Cell. Biol.* 50, 333–343

Rehfeld, J. F. (1971) *Acta Endocrinol.* 66, 169–176

Rehfeld, J. F. & Iversen, J. (173) *Eighth Congress of the International Diabetes Federation* (Malaisse, W. J. & Pirart, J., Eds.), p. 119, Amsterdam International Congress, Brussels Rehfeld, J. F. & Stadil, F. (1973) *Gut* 14, 369–373

Rehfeld, J. F., Stadil, F. & Malmstrom, J. (1975) *Gastrointestinal Hormones* (Thompson, J. C., Ed.), pp. 43–59, University of Texas Press, U.S.A.

rehfeld, J. F. (1976) 1st International Symposium on Gastrointestinal Hormones, A126, Asilomer, Calif.

Rehfeld, J. F. (1978a) *J. Biol. Chem.* 253, 4016–4021

Rehfeld, J. F. (1978b) *J. Biol. Chem.* 253, 4022–4030

Rehfeld, J. F. & Larsson, L. I. (1979) *Gastrins and the Vagus* (Rehfeld, J. F. & Andrup, E., Eds.), pp. 85–94, Academic Press, London Rehfeld, J. F. (1980) *Biochem. Biophys. Res. Commun.* 92, 811–818

Rehfeld, J. F., Larsson, L. I., Goltermann, N. R., Schwartz, T. W., Holst, J. J., Jensen, S. L. & Morley, J. S. (1980) *Nature* 284, 33–38

Rehfeld, J. F., Lindholm, J., Andersen, B. N., Bardram, L., Cantor, P., Fenger, M. & Ludecke, D. K. (1987) *N. Engl. J. Med.* 316 1244–1247

Richardson, C. T., Walsh, J. H. & Hicks, M. I. (1976) *Gastroenterology* 71, 19–23

Rivier, J., Brown, M., Rivier, C., Ling, N. & Vale, W. (1976) *Peptides 1976* (Loffet, A., Ed.), pp. 427–451, Bruzelles, Belgium Robert, A. & Yankee, E. W. (1975) *Proc. Soc. Exp. Biol. Med.* 148, 1155–1158

Rodriguez, M., Bali, J. -P., Magous, R., Castro, B. 7 Martinez, J. (1986) *Int. J. Peptide Protein Res.* 27, 293–299

Rodriguez, M., Dubreuil, P., Bali, J. -P. & Martinez, J. (1987a) *J. Med. Chem.* 30, 758–763

Rodriguez, M., Lignon, M. -F., Galas, M. -C., Fulcrand, P., Mendre, C., Aumélas, A., Laur, J. & Martinez, J. (1987b) *J. Med. Chem.* 30, 1366–1373

Roemer, D., Buescher, H. H., Hill, R. C., Pless, J., Bauer, W., Cardinaux, F., Closse, A., Hauser, D. & Huguenin, R. (1977) *Nature* 268, 547–549

Rosefeld, M. G., Abrass, I. B. & Chang, B. (1976) *Endrinology* 99, 611–618 Rothe, M. & Kunitz, F. W. (1957) *Ann. Chem.* 609, 88

Rovati, A. L. (1968), *Brit. J. Pharmacol.* 34, 667P

Rovati, A. L. (1976) *Scand. J. Gastroenterol.* 42, (Suppl.) 113–118

Rubini, E., Gilon, c. Selinger, Z. & Chorev, M. (1986) *Tetrahedron* 42, 6039–6045

Ruiz-Gayo, M., Daugé, V., Menant, I., Bégûe, D., Gacel, G. & Rogues, B. P. (1985) *Peptides* 6, 415–420

S

Sacks, J., Ivy, A. C. Burgess, J. P. & Vandolah, J. E. (1932) *Amer. J. Physiol.* 101, 331–338

Sakamoto, C., Goldfine, I. D. & Williams, J. A. (1983) *J. Biol. Chem.* 258, 12707–12711

Sandberg, B. E. B., Lee, C., Hanley, M. R. & Iversen, L. L. (1981) *Eur. J. Biochem.* 114, 329–337

Sandvik, A. K., Waldum, H. L., Kleveland, P. M. & Schulze Sognen, B. (1987) *Scand. J. Gastroenterol.* 22, 803–808

Schafmeyer, A., Becker, H. D., Werner, M. Fölsch, U. R. Cruetzfeld W. (1985) Digestion 32, 136–139

Schally, A. V., Coy, D. H. & Meyers, C. A. (1978) *Ann. Rev. Biochem.* 47, 89–128

Scheibye, S., Pedersen, B. S. & Lawesson, S. -O. (1978) *Bull. Soc. Chim. Belg.* 87, 229–238

Schiller, P. W., Natarajan, S. 7 Bodanszky, M. (1978) *Int. J. Peptide Protein Res.* 12, 139–142

Schoellmann, G. & Shaw, E. (1962) *Biochem. Biophys. Res. Commun.* 7, 36–40

Schön, I. Kisfauludy, L., Náfradi, J., Varga, L. & Varró, V. (1978a) *Hoppe-Seyler's Z. Physiol. Chem* 359, 897–916

Schön, I., Kisfauludy, L., Náfraádi, J., Varga, L. & Varroó, V. (1978b) *Hoppe-Seyler's Z. Physiol. Chem.* 359, 917–922

Shaw, E. (1967) *Methods Enzymol.* 11, 677–686

Shaw, M. J., Hadac, E. M. & Miller, L. J. (1987) *J. Biol. Chem.* 262, 14313–14318

Sheenan, J. C. & Hess, G. P. (1955) *J. Amer. Chem. Soc.* 77, 1067–1068

Singh, P., Rae-Venter, B. & Townsend, C. M. (1985) *Amer. J. Physiol.* 249, G761–765

Smith, C. W. & Walter, R. (1978) *Science* 199, 297–299

Smith, G., Jerome, C., Cushin, B., Eterno, R. & Simansky, K. (1981) *Science* 213, 1036–1037

Solcia, E. & Sampletro, R. (1965) *z. Zellforsch. Mikrosk. Anat.* 68, 689–701

Solcia, E., Vassallo, G. & Sampietro, R. (1967) *Z. Zellforsch. Mikrosk. Anat.* 81, 474–487

Solcia, E., Vassallo, G. & Capella, C. (1968) *Stain Technol.* 43, 257–263

Solcia, E., Vassallo, G. & Capella, C. (1969) *Gut* 10, 379–388

Solcia, E., Capella, C., Vassallo, G. & Buffa, R. (1975) *Int. Rev. Cytol.* 42, 223–286 soll, A. H. (1978) *J. Clin. Invest.* 61, 381–389

Soll, A. H. & Grossman, M. I. (1978) *Ann. Rev. Med.* 29, 495–507

Soll, A. H., Lewin, K. J. & Beaven, M. A. (1979) *Gastroenterology* 77, 1283–1290

Soll, A. H. (1981) *Physiology of the Gastrointestinal Tract* (Johnson, L. R., Ed.), pp. 673–691, Raven Press, New York Soll, A. H., Amirian, D. A. Thomas, L. P. Park, J. Elashoff, J. D., Beaven, M. A. & Yamada, T. (1984a) *Amer. J. Physiol.* 247, G715–723

Soll, A. H., Amirian, D. A. & Thomas, L. P. (1984b) *Amer. J. Physiol.* 247, G715–723

Soumarmon, A., Cheret, a. M. & Lewin, M. J. M. (1977) *Gastroenterology* 73, 900–903

Spanarkel, M. Martinez, J. Briet, C., Jensen, R. T. & Gardner, J. D. (1983) *J. Biol. Chem.* 258, 6746–6749

Spatola, A. F. (1983) *Chemistry and Biochemistry of Amino Acids, Peptides and Proteins* (Weinstein, B., Ed.), pp. 267–357, Marcel Dekker Inc., New York Spatola, A. F. 7 Darlak, K. (1988) *Tetrahedron* 44, 821–833

Stanley, M., Coalson, R., Grossman, M. I. & Johnson, L. R. (1972) *Gastroenterology* 63, 264–269

Stave, R., Brandtzaeg, P., Nygaard, K. & Fausa, O. (1978) *Scand. J. Gastroenterol.* 13, 685–692

Steeigerwalt, R. W. & Williams, J. A. (1981) *Endocrinology* 109 1746-1753

Steigerwalt, R. W. & Williams, J. A. (1984) *Regul. Peptides* 8, 51-59

Steigerwalt, R. W. Goldfine, I. D. & Williams, J. A. 91984) *Amer. J. Physiol.* 247, G709-714

Stening, G. F. & Grossman, M. I. (1969a) *Amer. J. Physiol.* 217, 262-266

Stening, G. F. & Grossman, M. I. (1969b) *Gastroenterology* 56, 1047-1052

Stewart, F. H. C. (1981) *Aust. J. Chem.* 34, 2431-2438

Stewart, J. M. & Young, J. D. (1984) *Solid Phase Peptide Synthesis* (2nd ed.) pp. 18-27, Pierce Chemical Co., U.S.A.

Storer, A. C., Angus, R. H. 7 Carey, P. R. (1988) *Biochemistyr* 27, 264-268

Straus, E. 7 Yalow, R. S. (1974) *Gastroeneterology* 66, 936-943

Strickland, R. g. & MacKay, I. R. 91973) *Am. J. Dig. Dis.* 18, 426-440

Strunz, U., Thompson, M., Elashoff, J. & Grossman, M. I. (1978) *Gastroenterology* 74, 550-553

Sullivan, M., Cohen, S. & Snape, W. J. (1978) *N. Engl. J. Med.* 298, 878-883

Suydam, F. H., Greth, W. E. & Langerman, N. R. (1969) *J. Org. Chem* 34, 292-296

Szurszewski, J. (1975) *J. Physiol.* 252, 335-361

T

Takahashi, Y., Kato, K., Hayashizaki, Y., Wakabayashi, T., Ohtsuka, E., Matsuki, S., Ikehara, M. & Matsubara, K. (1985) *Proc. Natl. Acad. Sci., U.S.A.* 82, 1931-1935

Takeuchi, K., Speir, G. R. & Johnson, L. R. (1979a) *Amer. J. Physiol.* 237, E284-294

Takeuchi, K., Speir, G. R. & Johnson, L. R. (1979b) *Amer. J. Physiol.* 237, E295-300

Takeuchi, K. Speir, G. R. 7 Johnson, L. R. (1980) *Amer. J. Physiol.* 238, G135-140

Tamminga, C. A., LIttman, R. L., Alpha, L. D., Chase, T. N., Thaker, G. K. & Wagman, A. M. (1986) *Psychopharmacol.* 88, 3987-391

Takemoto, K., Jornvall, H., Siimesmaa, S., Hallden, G. & Mutt, V. (1984) *FEBS Lett.* 174, 289-293

Tenbrink, R. E. (1987), *J. Org. Chem.* 52, 418-422

Tepperman, B. & Evered, M. (1980) *Science* 209, 1142-1143

Thorsen, M., Yde, B., Pedersen, U., Clausen, K. & Lawesson, S. -O. (1983) *Tetrahedron* 39, 3429-3435

Thunberg, R. (1967) ]*Exper. Cell. Res.* 47, 108-115

Tinney, F. J. Roark, w. H. Nicolaides, E. D., Davis, R. E., Voigtman, R. E. & Marriot, J. G. (1985) *Peptides-Structure and Function* (Deber, C. M., Hruby, V. J. & Kopple, K. D., Eds.), p. 172, Peirce Chemical Co., Illinois Tracy, H. J. & Gregory, R. A. (1964) *Nature* 204, 935-938

Tritsch, G. L., Sachatello, C. R., Grahl-Nielsen, O. Moriarty, C. L. & Sedwick, J. (1971) *J. Med.* 2, 82-85

Troll, W. & Cannon, R. K. (1953) *J. Biol. Chem,* 200, 803-811

U

Urushidani, T., Hanzel, D. K. & Forte, J. G. (1987) *Biochim. Biophys. Acta* 930, 209-219

V

Vagne, M. & Grossman, M. I. (1968) *Amer. J. Physiol.* 215, 881-884

Vanderhaegen, J. J., Signeau, J. c. & Gepts, W. (1975) *Nature* 257, 604-605

Vinik, A. I., Heldsinger, A. & skoglund, M. L. (1981) *Gastroenterology* 80,

W

Wallace, D. A., Bates, S. R. E., Walker, B., Kay, G., White, J., Guthrie, D. J. S., Blumson, N. L. & Elmore, D. T. (1986) *Biochem. J.* 239, 797-799

Wallmark, B., Sachs, G., Mardh, S. & Fellenius, E. (1983) *Biochem. Biophys. Acta* 728, 31-38

Walsh, J. H. & Laster, Z. (1973) *Biochem. Med.* 8, 432-449

Welsh, J. H., Debas, H. T. 7 Grossman, M. I. (1974) *J. Clin. Invest.* 54, 477-485

Walsh, J. H. & Grossman, M. I. (1975) *N. Engl. J. Med.* 292, 1324-1332

Walsh, J. H., Richardson, C. T. & Fordtrane, S. S. (1975), *J. Clin. Invest.* 55, 462-468

Walsh, J. H., Reeve, J. R., Vigna, S. R., Chew, P., Wong, H. C. 7 Dockray, G. J. (1978) *Scand. J. Gastroenterol.* 13 (Suppl. 49), 191

Walsh, J. H., Lamers, C. B. & valenzuela, J. E. (1982) *Gastroenterology* 3, 438-444

Wang, C. C. & Grossman, M. I. (1951) *Amer. J. Physiol.* 164, 527-545

Westlund, K. N., Wynn, P. C., Chmielowiec, S., Collins, T. J. and Childs, G. V. (1984) *Peptides* 5, 627-634

Williams, J. A. (1985) *Folia Endrocrinol.* 61, 553-540

Williams, J. A. & Hootman, S. R. (1986) *The Exocrine Pancrease: Biology, Pathobiology and Diseases* (Go, V. L. W., Gardner, J. D. & Brooks, F. P., Eds.), pp. 123-139, Raven Press, New York Williams, J. A. & McChesney, D. J. (1987) *Regul. Peptides* 18, 108-117

Wilson, R. M., Boiden, G., Shore, L. S. & Essa-Khoumar, N. (1977) *Diabetes* 26, 7-10

Wislicenus, J. (1869) *Z. Chem.*, 324-326

Wissman, H., Schleybach, R., Schoelkens, B. & Geiger, R. (1973) *Hoppe-Seyler's Z. Physiol. Chem.* 354, 1591-1598

Wolosin, J. M. & Forte, J. G. (1981), *J. Biol. Chem.* 256, 3149-3152

Woodward, E. R., Lyon, E. S., Landor, J. & Dragstedt, L. R. (1954) *Gastroenterology* 27, 766-785

Wünsch, E. (1967) *Z. Naturforsch.* 22b, 1269-1276

Wünsch, E. 7 Deimer, K. H. (1972) *Hoppe-Seyler's Z. Physiol. Chem.* 353, 1246-1254

Wünsch, E., Jaeger, E., Deffner, M. & Scharf, R. (1972) *Hoppe-Seyler's Z. Physiol. Chem.* 1716-1720

Wünsch, E., Scharf, R., Peggion, E., Foffani, M. & Bali, J. -P. (1986) *Biopolymers* 25, 229-234

Yalow, R. S.+Berson, S. A. (1970) *Gastroenterology* 58, 1-14

Yalow, R. S. & Berson, S. A. (1972) *Biochem. Biophys. Res. Commun.* 48, 391-395

Yamada, T., Wako, H., Saitô, N., Isogai, Y. & Watari, H. (1976) *Int. J. Peptide Protein Res.* 8, 607-614

Yoo, O. J., Powell, C. T. & Agarwal, K. L. (1982) *Proc. Natl. Acad. Sci., U.S.A.* 79, 1049-1053

Zarbin, M. A., Innis, R. B., Wamsley, J. K. Snyder, S. H. & Kuhar, M. J. (1983) *J. Neurosci.* 3, 877–906
Zimmerman, M., Yurewicz, E., & Patel, G. (1976) *Anal. biochem.* 70, 258–262
Zollinger, R. M. & Ellison, E. M. (1955) *Ann. Surg.* 142, 709–728
Zollinger, R. M. & Colemann, D. V. (174) *Influence of Pancreatic Tumours in the Stomach* (Thomas, C. C. Ed.), Springfiled, Ill.
I claim:
1. A compound having the following formula:
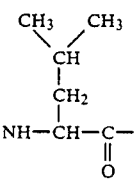
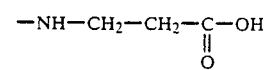
where R is biotin-NH, dansyl-NH, and fluorescein-NH, H—, or Nh$_2$—.